(12) United States Patent
Chapuis et al.

(10) Patent No.: US 11,034,748 B2
(45) Date of Patent: Jun. 15, 2021

(54) HIGH AFFINITY MAGE-A1-SPECIFIC TCRS AND USES THEREOF

(71) Applicant: FRED HUTCHINSON CANCER RESEARCH CENTER, Seattle, WA (US)

(72) Inventors: Aude Chapuis, Seattle, WA (US); Thomas Schmitt, Seattle, WA (US); Megan McAfee, Seattle, WA (US)

(73) Assignee: FRED HUTCHINSON CANCER RESEARCH CENTER, Seattle, WA (US)

(*) Notice: Subject to any disclaimer, the term of this patent is extended or adjusted under 35 U.S.C. 154(b) by 0 days.

(21) Appl. No.: 16/571,013

(22) Filed: Sep. 13, 2019

(65) Prior Publication Data
US 2020/0017568 A1    Jan. 16, 2020

Related U.S. Application Data

(63) Continuation of application No. PCT/US2018/022759, filed on Mar. 15, 2018.

(60) Provisional application No. 62/471,956, filed on Mar. 15, 2017.

(51) Int. Cl.
| | |
|---|---|
| *A61K 35/17* | (2015.01) |
| *A61K 39/00* | (2006.01) |
| *A61P 35/00* | (2006.01) |
| *A61P 35/02* | (2006.01) |
| *C07K 14/00* | (2006.01) |
| *C07K 14/705* | (2006.01) |
| *C07K 14/725* | (2006.01) |
| *C12N 5/0783* | (2010.01) |

(52) U.S. Cl.
CPC .......... *C07K 14/7051* (2013.01); *A61K 35/17* (2013.01); *A61P 35/00* (2018.01); *C07K 14/70517* (2013.01); *C12N 5/0638* (2013.01); *C12N 2510/00* (2013.01)

(58) Field of Classification Search
CPC .. A61K 35/17; A61K 39/00; A61K 2039/515; A61K 2039/5158; A61P 35/00; A61P 35/02; C07K 14/00; C07K 14/4748; C07K 14/705; C07K 14/7051; C07K 14/70517; C12N 5/0634; C12N 5/0636; C12N 2510/00
See application file for complete search history.

(56) References Cited

U.S. PATENT DOCUMENTS

| | | | |
|---|---|---|---|
| 5,420,032 A | 5/1995 | Marshall et al. | |
| 6,410,319 B1 | 6/2002 | Raubitschek et al. | |
| 6,596,536 B1 * | 7/2003 | Hercend | C07K 14/7051 424/133.1 |
| 6,833,252 B1 | 12/2004 | Dujon et al. | |
| 7,446,191 B2 | 11/2008 | Jensen | |
| 7,514,537 B2 | 4/2009 | Jensen | |
| 8,217,144 B2 * | 7/2012 | Jakobsen | A61P 31/00 530/350 |
| 8,519,100 B2 | 8/2013 | Jakobsen et al. | |
| 8,697,359 B1 | 4/2014 | Zhang | |
| 8,785,601 B2 * | 7/2014 | Rosenberg | C07K 14/7051 530/387.3 |
| 8,822,647 B2 | 9/2014 | Jensen | |
| 9,228,007 B1 * | 1/2016 | Kitchen | C07K 14/7051 |
| 9,574,000 B2 | 2/2017 | Langermann et al. | |
| 9,586,997 B2 * | 3/2017 | Sahin | C12N 15/85 |
| 10,000,546 B2 * | 6/2018 | Odunsi | A61K 39/0011 |
| 10,023,625 B2 * | 7/2018 | Smith | A61P 35/00 |
| 10,093,977 B2 * | 10/2018 | Sugiyama | C12Q 1/6881 |
| 10,202,640 B2 * | 2/2019 | Davis | C12Q 1/686 |
| 10,370,423 B2 * | 8/2019 | Sahin | A61P 37/04 |
| 10,377,808 B2 * | 8/2019 | Blankenstein | C07K 14/7051 |
| 10,544,392 B2 * | 1/2020 | Gros | C12N 5/0636 |
| 10,550,182 B2 * | 2/2020 | Alten | C07K 14/78 |
| 10,648,036 B2 * | 5/2020 | Sugiyama | C12Q 1/6881 |
| 2003/0148973 A1 * | 8/2003 | Emtage | C07K 14/4748 514/44 R |
| 2004/0002092 A1 | 1/2004 | Arnould et al. | |
| 2004/0087025 A1 | 5/2004 | June et al. | |
| 2006/0078552 A1 | 4/2006 | Arnould et al. | |
| 2006/0153826 A1 | 7/2006 | Arnould et al. | |
| 2006/0206949 A1 | 9/2006 | Arnould et al. | |
| 2007/0117128 A1 | 5/2007 | Smith et al. | |
| 2008/0064631 A1 * | 3/2008 | Molldrem | C07K 14/7051 530/350 |
| 2008/0311142 A1 * | 12/2008 | Yu | A61K 39/0011 424/185.1 |

(Continued)

FOREIGN PATENT DOCUMENTS

| | | |
|---|---|---|
| CN | 102295702 A | 12/2011 |
| CN | 105316362 A | 2/2016 |

(Continued)

OTHER PUBLICATIONS

Leiden et al, GenBank E27552, 1999.*

(Continued)

*Primary Examiner* — Kevin K Hill
(74) *Attorney, Agent, or Firm* — Seed IP Law Group LLP

(57) ABSTRACT

The present disclosure provides TCRs with high or enhanced affinity against various tumor associated antigens (including human MAGE-A1 epitopes), T cells expressing such high affinity antigen-specific TCRs, nucleic acids encoding the same, and compositions for use in treating diseases or disorders in which cells overexpress one or more of these antigens, such as in cancer.

30 Claims, 15 Drawing Sheets

Specification includes a Sequence Listing.

(56) References Cited

U.S. PATENT DOCUMENTS

| | | |
|---|---|---|
| 2009/0304679 A1 | 12/2009 | Weidanz |
| 2010/0065818 A1 | 3/2010 | Kim et al. |
| 2010/0190163 A1* | 7/2010 | Sugiyama .......... C07K 14/7051 435/6.16 |
| 2011/0189141 A1 | 8/2011 | Kieback et al. |
| 2011/0243972 A1 | 10/2011 | Jaffee |
| 2011/0301073 A1 | 12/2011 | Gregory et al. |
| 2014/0068797 A1 | 3/2014 | Doudna et al. |
| 2014/0186843 A1 | 7/2014 | Zhang et al. |
| 2015/0292034 A1 | 10/2015 | Sugiyama |
| 2015/0337369 A1 | 11/2015 | Davis et al. |
| 2015/0353622 A1 | 12/2015 | Blankenstein et al. |
| 2016/0083449 A1* | 3/2016 | Schmitt ............ A61K 38/2086 424/93.21 |
| 2016/0280755 A1* | 9/2016 | Smith ................ C07K 14/4747 |
| 2018/0161396 A1* | 6/2018 | Alten ................ A61K 38/1764 |
| 2018/0245242 A1* | 8/2018 | Schendel ............. C40B 40/10 |
| 2019/0169261 A1* | 6/2019 | Ellinger .......... C07K 14/70539 |

FOREIGN PATENT DOCUMENTS

| | | |
|---|---|---|
| CN | 106749620 A | 5/2017 |
| WO | 97/09433 A1 | 3/1997 |
| WO | 2010/084158 A1 | 7/2010 |
| WO | 2012/054825 A1 | 4/2012 |
| WO | 2013/025779 A1 | 2/2013 |
| WO | 2013/074916 A1 | 5/2013 |
| WO | 2014/031687 A1 | 2/2014 |
| WO | 2014/059173 A2 | 4/2014 |
| WO | 2015/066262 A1 | 5/2015 |
| WO | 2015/071474 A9 | 5/2015 |
| WO | WO 15/173112 * | 11/2015 |
| WO | 2016/040724 A1 | 3/2016 |
| WO | WO 16/040900 * | 3/2016 |
| WO | 2016/054638 A1 | 4/2016 |
| WO | 2016/134333 A1 | 8/2016 |
| WO | WO 16/177195 * | 10/2016 |
| WO | 2017/021526 A1 | 2/2017 |

OTHER PUBLICATIONS

Charmley et al, GenBank PH1573, 1993.*
Poosarla et al, Biotech. & Bioengin. 114(6): 1331-1342, 2017.*
Borg et al, Nature Immunol. 6(2): 171-180, 2005.*
Goyarts et al, Mol. Immunol. 35: 593-607, 1998.*
Goel et al, J. Immunol. 173: 7358-7367, 2004.*
MacCallum et al, J. Mol. Biol. 262:732-745, 1996.*
Casset et al, Biochem. Biophys. Res. Comm. 307:198-205, 2003.*
Bartok et al, Mol. Immunol. 47: 1613-1618, 2010.*
Edwards et al, J. Mol. Biol. 334: 103-118, 2003.*
Ademuyiwa et al., "NY-ESO-1 Cancer Testis Antigen Demonstrates High Immunogenicity in Triple Negative Breast Cancer," *PLoS ONE* 7(6):e38783, 2012. (9 pages).
Argast et al., "I-PpoI and I-CreI Homing Site Sequence Degeneracy Determined by Random Mutagenesis and Sequential in Vitro Enrichment," *J. Mol. Biol.* 280:345-353, 1998.
Ashworth et al., "Computational redesign of endonuclease DNA binding and cleavage specificity," *Nature* 441(7093):656-659, 2006. (11 pages).
Barrow et al., "Tumor Antigen Expression in Melanoma Varies According to Antigen and Stage," *Clin Cancer Res* 12(3):764-771, 2006. (9 pages).
Belfort et al., "Homing endonucleases: keeping the house in order," *Nucleic Acids Research* 25(17):3379-3388, 1997.
Bowerman et al., "Engineering the Binding Properties of the T Cell Receptor:Peptide:Mhc Ternary Complex that Governs T Cell Activity," *Mol Immunol.* 46(15):3000-3008, 2009. (23 pages).
Brentjens et al., "Genetically Targeted T Cells Eradicate Systemic Acute Lymphoblastic Leukemia Xenografts," *Clin Cancer Res* 13(18):5426-5435, 2007. (11 pages).

Cavallo et al., "2011: the immune hallmarks of cancer," *Cancer Immunol Immunother* 60:319-326, 2011.
Chapuis et al., "Abstract LB-136:IL-21-derived melanoma-reactive CTL combined with anti-CTLA4 persist, acquire central memory characteristics, and mediate tumor regression in patients with metastatic melanoma," AACR 103rd Annual meeting, Chicago, Illinois, Mar. 31-Apr. 4, 2012, 4 pages.
Chapuis et al., "Transferred melanoma-specific CD8+ T cells persist, mediate tumor regression, and acquire central memory phenotype," *PNAS* 109(12):4592-4597, 2012.
Chapuis et al., "Transferred WT1-reactive CD8+ T cells can mediate antileukemic activity and persist in post-transplant patients," *Sci Transl Med.* 5(174):174ra27, 2013. (25 pages).
Chevalier et al., "Design, Activity, and Structure of a Highly Specific Artificial Endonuclease," *Molecular Cell* 10:895-905, 2002.
Chothia et al., "The outline structure of the T-cell $\alpha\beta$ receptor," *The EMBO Journal* 7(12):3745-3755, 1988.
Cole et al., "CD8: Adhesion Molecule, Co-Receptor and Immuno-Modulator," *Cellular & Molecular Immunology* 1(2):81-88, 2004.
Črnjević Tanja et al., "High expression of MAGE-A10 cancer-testis antigen in triple-negative breast cancer," *Med Oncol* 29:1586-1591, 2012.
Curigliano et al., "Cancer—testis antigen expression in triple-negative breast cancer," *Annals of Oncology* 22:98-103, 2011.
Dangaj et al., "Novel recombinant human B7-H4 antibodies overcome tumoral immune escape to potentiate T cell anti-tumor responses," *Cancer Res.* 73(15):4820-4829, 2013. (19 pages).
Desjarlais et al., "Use of a zinc-finger consensus sequence framework and specificity rules to design specific DNA binding proteins," *Proc. Natl. Acad. Sci.* 90:2256-2260, 1993.
Dossett et al., "Adoptive Immunotherapy of Disseminated Leukemia With TCR-transduced, CD8+ T Cells Expressing a Known Endogenous TCR," *Molecular Therapy* 17(4):742-749, 2009.
Dujon et al., "Mobile introns: definition of terms and recommended nomenclature," *Gene.* 82:115-118, 1989.
Dunbar et al., "ANARCI: antigen receptor numbering and receptor classification," *Bioinformatics* 32(2):298-300, 2016.
Epinat et al., "A novel engineered meganuclease induces homologous recombination in yeast and mammalian cells," *Nucleic Acids Research* 31(11):2952-2962, 2003.
Floros et al., "Anticancer Cytokines: Biology and Clinical Effects of IFN-$\alpha$2, IL-2, IL-15, IL-21, and IL-12," *Semin Oncol.* 42(4):539-548, 2015. (17 pages).
Gao et al., "Molecular interactions of coreceptor CD8 and MHC class I: the molecular basis for functional coordination with the T-cell receptor," *Immunology Today* 21(12):630-636, 2000.
GenBank Accession No. CP001841, "Treponema azotonutricium ZAS-9, complete genome," retrieved from https://www.ncbi.nlm.nih.gov/nuccore/CP001841, 2020. (258 pages).
GenBank Accession No. HF380962, "*Hordeum vulgare* subsp. *vulgare* cv. Morex GSS, clone HVVMRXALLMA0066A09_f, genomic survey sequence," retrieved from https://www.ncbi.nlm.nih.gov/nucgss/HF380962, 2020. (1 page).
Gimble et al., "Substrate Recognition and Induced DNA Distortion by the PI-SceI Endonuclease, an Enzyme Generated by Protein Splicing," *J. Mol. Biol.* 263:163-180, 1996.
Gure et al., "Cancer-Testis Genes Are Coordinately Expressed and Are Markers of Poor Outcome in Non-Small Cell Lung Cancer," *Clin Cancer Res* 11(22):8055-8062, 2005. (9 pages).
Hanahan et al., "Hallmarks of Cancer: The Next Generation," *Cell* 144:646-674, 2011.
Hanahan et al., "The Hallmarks of Cancer," *Cell* 100:57-70, 2000.
Ho et al., "In vitro methods for generating CD8+ T-cell clones for immunotherapy from the naïve repertoire," *Journal of Immunological Methods* 310:40-52, 2006.
International Search Report and Written Opinion dated Aug. 13, 2018, for International Application No. PCT/US18/22759, 12 pages.
Jasin, "Genetic manipulation of genomes with rare-cutting endonucleases," *TIG* 12(6):224-228, 1996.
Jinek et al., "A programmable dual RNA-guided DNA endonuclease in adaptive bacterial immunity," *Science* 337(6096):816-821, 2012. (14 pages).

(56) References Cited

OTHER PUBLICATIONS

Jores et al., "Resolution of hypervariable regions in T-cell receptor β chains by a modified Wu-Kabat index of amino acid diversity," *Proc. Natl. Acad. Sci.* 87:9138-9142, 1990.
Kerkar et al., "MAGE-A is more highly expressed than NY-ESO-1 in a systematic immunohistochemical analysis of 3668 cases," *J Immunother.* 39(4):181-187, 2016. (13 pages).
Kuball et al., "Facilitating matched pairing and expression of TCR chains introduced into human T cells," *Blood* 109(6):2331-2338, 2007.
Kyrgidis et al., "Melanoma: Stem cells, sun exposure and hallmarks for carcinogenesis, molecular concepts and future clinical implications," *J Carcinog* 9:3-29, 2010. (26 pages).
Leen et al., "Improving T Cell Therapy for Cancer," *Annu. Rev. Immunol.* 25:243-265, 2007. (26 pages).
Lefranc et al., "IMGT unique numbering for immunoglobulin and T cell receptor variable domains and Ig superfamily V-like domains," *Developmental and Comparative Immunology* 27:55-77, 2003.
Li et al., "Evaluation of melanoma antigen (MAGE) gene expression in human cancers using The Cancer Genome Atlas," *Cancer Genetics* 208:25-34, 2015.
Liu et al., "Selective inhibition of IDO1 effectively regulates mediators of antitumor immunity," *Blood* 115(17):3520-3530, 2010. (12 pages).
Mautino et al., "Abstract 491:NLG919, a novel indoleamine-2,3-dioxygenase (IDO)-pathway inhibitor drug candidate for cancer therapy," *Proceedings of the 104th Annual Meeting of the American Association for Cancer Research*, Washington DC., Philadelphia, PA, Apr. 6-10, 2013, 2 pages. (Abstract).
Mrklić et al., "Co-expression of cancer testis antigens and topoisomerase 2-alpha in triple negative breast carcinomas," *Acta Histochemica* 116:740-746, 2014.
Pâques et al., "Meganucleases and DNA Double-Strand Break-Induced Recombination: Perspectives for Gene Therapy," *Current Gene Therapy* 7:49-66, 2007. (19 pages).
Park et al., "Cancer Stem Cell-Directed Therapies: Recent Data From the Laboratory and Clinic," *Molecular Therapy* 17(2):2019-230, 2009.
Park et al., "Expression of MAGE-A and NY-ESO-1 in Primary and Metastatic Cancers," *J Immunother.* 39(1):1-7, 2016. (17 pages).
Perler et al., "Protein splicing elements: inteins and exteins—a definition of terms and recommended nomenclature," *Nucleic Acids Research*, 22(7):1125-1127, 1994.
Porteus et al., "Gene targeting using zinc finger nucleases," *Nature Biotechnology* 23(8):967-973, 2005.
Robbins et al., "Tumor Regression in Patients With Metastatic Synovial Cell Sarcoma and Melanoma Using Genetically Engineered Lymphocytes Reactive With NY-ESO-1," *Journal of Clinical Oncology* 29(7):917-924, 2011.
Robins et al., "Comprehensive assessment of T-cell receptor β-chain diversity in αβ T cells," *Blood* 114(19):4099-4107, 2009. (20 pages).
Robins et al., "Overlap and effective size of the human CD8+ T-cell receptor repertoire," *Sci Transl Med.* 2(47):47ra64, 2010. (9 pages).
Schmitt et al., "T Cell Receptor Gene Therapy for Cancer," *Human Gene Therapy* 20:1240-1248, 2009.
Scholten et al., "Codon modification of T cell receptors allows enhanced functional expression in transgenic human T cells," *Clinical Immunology* 119:135-145, 2006.
Simpson et al., "Cancer/Testis Antigens, Gametogenesis and Cancer," *Nature Reviews* 5:615-625, 2005.
Stone et al., "Role of T cell receptor affinity in the efficacy and specificity of adoptive T cell therapies," *Frontiers in Immunology* 4(244), 2013. (16 pages).
Stromnes et al., "Re-adapting T cells for cancer therapy: from mouse models to clinical trials," *Immunol Rev.* 257(1):145-164, 2014. (34 pages).

Sussman et al., "Isolation and Characterization of New Homing Endonuclease Specificities at Individual Target Site Positions," *J. Mol. Biol.* 342:31-41, 2004.
Terentis et al., "The Selenazal Drug Ebselen Potently Inhibits Indoleamine 2,3-Dioxygenase by Targeting Enzyme Cysteine Residues," *Biochemistry* 49:591-600, 2010.
Till et al., "Adoptive immunotherapy for indolent non-Hodgkin lymphoma and mantle cell lymphoma using genetically modified autologous CD20-specific T cells," *Blood* 112(6):2261-2271, 2008. (25 pages).
Torikai et al., "A foundation for universal T-cell based immunotherapy: T cells engineered to express a CD19-specific chimeric-antigen-receptor and eliminate expression of endogenous TCR," *Blood* 119(24):5697-5705, 2012. (18 pages).
Torikai et al., "Genetic editing of Hla expression in hematopoietic stem cells to broaden their human application," *Scientific Reports* 6:21757, 2016. (11 pages).
Torikai et al., "Toward eliminating HLA class I expression to generate universal cells from allogeneic donors," *Blood* 122(8):1341-1349, 2013. (26 pages).
Velazquez et al., "Expression of the cancer/testis antigen NY-ESO-1 in primary and metastatic malignant melanoma (MM)-correlation with prognostic factors," *Cancer Immunity* 7:11, 2007. (7 pages).
Walseng et al., "A TCR-based Chimeric Antigen Receptor," *Scientific Reports* 7:10713, 2017. (10 pages).
Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, 2007. (16 pages).
Warren et al., "Exhaustive T-cell repertoire sequencing of human peripheral blood samples reveals signatures of antigen selection and a directly measured repertoire size of at least 1 million clonotypes," *Genome Research* 21:790-797, 2011. (9 pages).
Weon et al., "The MAGE protein family and cancer," *Curr Opin Cell Biol.* 37:1-8, 2015. (15 pages).
Wolfe et al., "Analysis of Zinc Fingers Optimized via Phage Display: Evaluating the Utility of a Recognition Code," *J. Mol. Biol.* 285:1917-1934, 1999.
Xie et al., "sgRNAcas9: A Software Package for Designing CRISPR sgRNA and Evaluating Potential Off-Target Cleavage Sites," *PLoS ONE* 9(6):e100448, 2014. (9 pages).
Zoete et al., "Structure-based, rational design of T cell receptors," *Frontiers in Immunology* 4:268, 2013. (19 pages).
Chapuis, "Harnessing the therapeutic potential of native and TCR gene-modified T cells," *Illumina Immuno-Oncology Symposium*, Mar. 14, 2017. (68 pages; pp. 57-68).
McAfee, "Identification of MAGE-A1 TCRs that confer function to CD8+ and CD4+ T cells for the advancement of T cell immunotherapy," *Keystone Symposia—Cancer Immunology and Immunotherapy: Taking a Place in Mainstream Oncology*, Mar. 19, 2017. (15 pages).
Extended European Search Report, dated Nov. 12, 2020, for European Patent Application No. 18767104, 9 pages.
Linnemann et al., "High-throughput identification of antigen-specific TCRs by TCR gene capture," *Nature Medicine* 19(11):1534-1541, 2013. (10 pages).
McAfee et al., "Abstract 3569: Humanized mouse model of MAGE-A 1-targeted anti-melanoma T cell therapy," Mar. 14, 2018. (4 pages).
Dossa et al., "Development of T-cell immunotherapy for hematopoietic stem cell transplantation recipients at risk of leukemia relapse," *Blood.* 131(1):108-120, 2018. (25 pages).
McAfee et al., "3569: Humanized mouse model of MAGE-A1 targeted anti-melanoma T cell therapy," [abstract]. In: Proceedings of the 109th Annual Meeting of the American Association for Cancer Research; Apr. 14-18, 2018; Chicago, Illinois. Philadelphia (PA): AACR; 2018. Abstract nr {3569}, Apr. 17, 2018. (13 pages).
Rongvaux et al., "Development and function of human innate immune cells in a humanized mouse model," *Nat Biotechnol.* 32(4):364-372, 2014. (23 pages).
Sommermeyer et al., "Chimeric antigen receptor-modified T cells derived from defined CD8+ and CD4+ subsets confer superior antitumor reactivity in vivo," *Leukemia.* 30(2):492-500, Feb. 2016. (20 pAGES).

(56) References Cited

OTHER PUBLICATIONS

Willemsen et al., "Redirecting human CD4+ T lymphocytes to the MHC class I-restricted melanoma antigen MAGE-A1 by TCR aβ gene transfer requires CD8α," *Gene Therapy* 12:140-146, 2005.

* cited by examiner

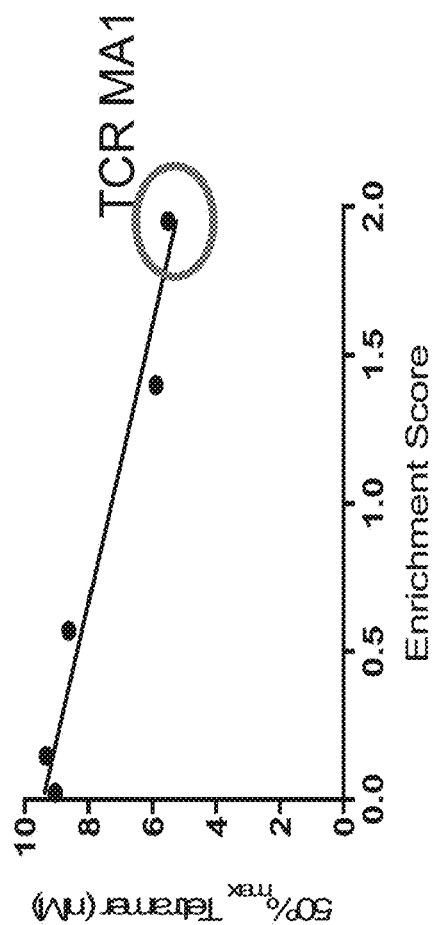
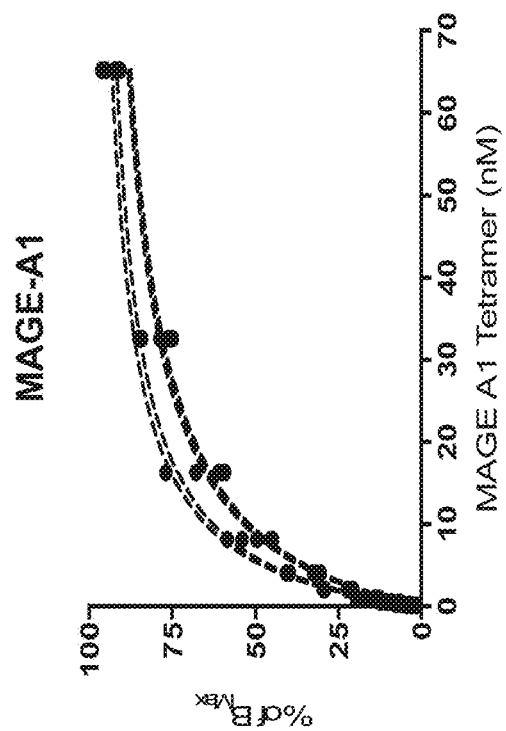
FIG. 4B
FIG. 4A

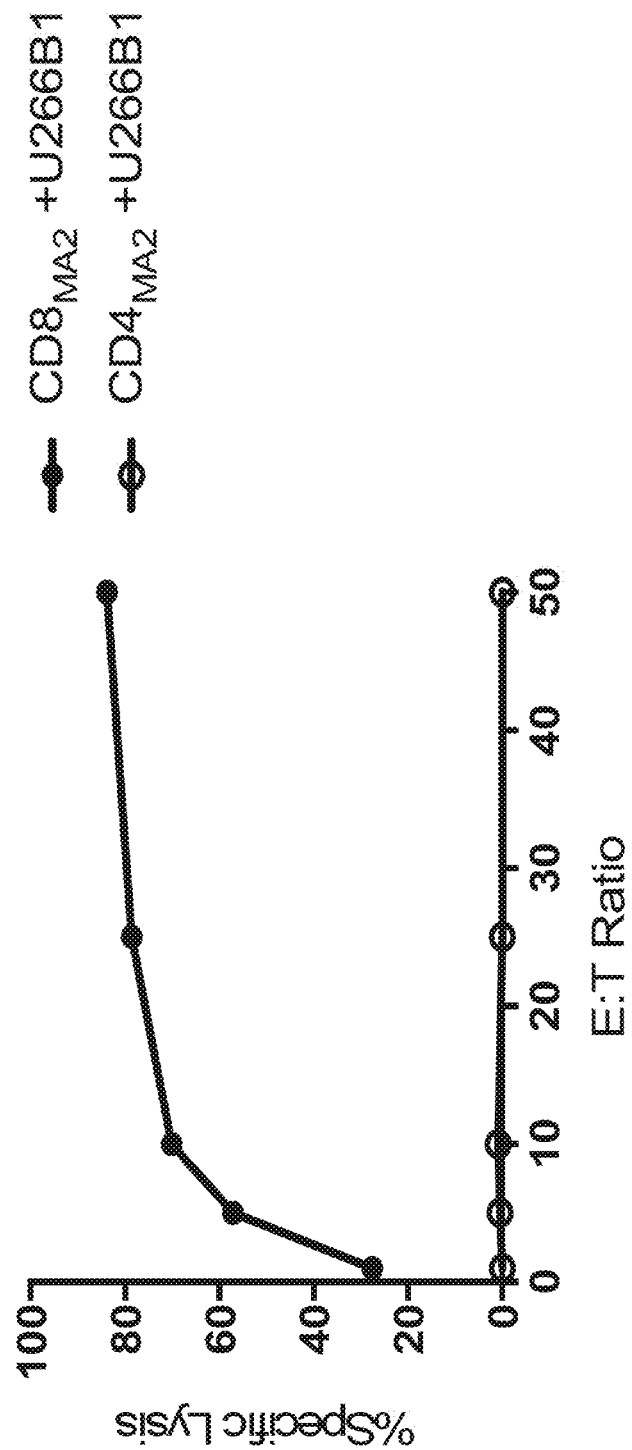

HIGH AFFINITY MAGE-A1-SPECIFIC TCRS AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_446C1_SEQUENCE_LISTING.txt. The text file is 86.3 KB, was created on Sep. 13, 2019, and is being submitted electronically via EFS-Web.

BACKGROUND

Adoptive transfer of tumor-specific T-cells is an appealing strategy to eliminate existing tumors and requires the establishment of a robust population of antigen-specific T cells in vivo to eliminate existing tumor and prevent recurrences (Stromnes et al., *Immunol. Rev.* 257:145, 2014). Although transfer of tumor-specific CD8$^+$ cytotoxic T lymphocytes (CTLs) is safe and can mediate direct anti-tumor activity in select patients (Chapuis et al., *Cancer Res.* 72:LB-136, 2012; Chapuis et al., *Sci. Transl. Med.* 5:174ra127, 2013; Chapuis et al., *Proc. Nat'l. Acad. Sci. U.S.A.* 109:4592, 2012),[2-4] the variability in the avidity of the CTLs isolated from each patient or donor limits the anti-tumor efficacy in clinical trials (Chapuis et al., 2013). Since TCR affinity is an important determinant of CTL avidity (Zoete et al., *Frontiers Immunol.* 4:268, 2013), strategies have been developed to redirect the antigen specificity of donor or patient T cells using high affinity TCRα/β genes isolated from a well-characterized T cell clone specific for a tumor-specific antigen (Stromnes et al., *Immunol. Rev.* 257:145, 2014; Robbins et al., *J. Clin. Oncol.* 29:917, 2011). Such high affinity self/tumor-reactive T cells are rare since T cells that express self/tumor-reactive TCRs are subject to central and peripheral tolerance (Stone and Kranz, *Frontiers Immunol.* 4:244, 2013), with relative TCR affinities varying widely between donors. Therefore, many matched donors must be screened to identify a sufficiently high-affinity tumor-specific T cell clone from which a TCRα/β gene therapy construct can be generated. For example, isolation of a naturally elicited Wilms' Tumor antigen 1 (WT1)-specific TCR with high functional avidity for a single HLA-allele required screening of hundreds of WT-specific T cell lines representing thousands of individual T cell clones from the peripheral repertoires of greater than 75 normal donors, a very time and labor intensive process (Chapuis et al., 2013; Schmitt et al., *Hum. Gene Ther.* 20:1240, 2009; Ho et al., *J. Immunol. Methods* 310:40, 2006).

There is a need for alternative antigen-specific TCR immunotherapies directed against various cancers, such as leukemia and tumors. Presently disclosed embodiments address these needs and provide other related advantages.

BRIEF DESCRIPTION OF THE DRAWINGS

FIGS. 4A and 4B show, respectively, (A) specific binding of MAGE-A1:HLA tetramers by TCRs identified using methods of the present disclosure and (B) enrichment of MAGE-A1-specific TCRs.

FIG. 7C shows target cell lysis (Cr$^{51}$ release) by CD8$^+$ T cells expressing MAGE-A1-specific TCR of this disclosure and the lack of killing by comparable CD4$^+$ T cells.

DETAILED DESCRIPTION

Figures 1A, 1B:
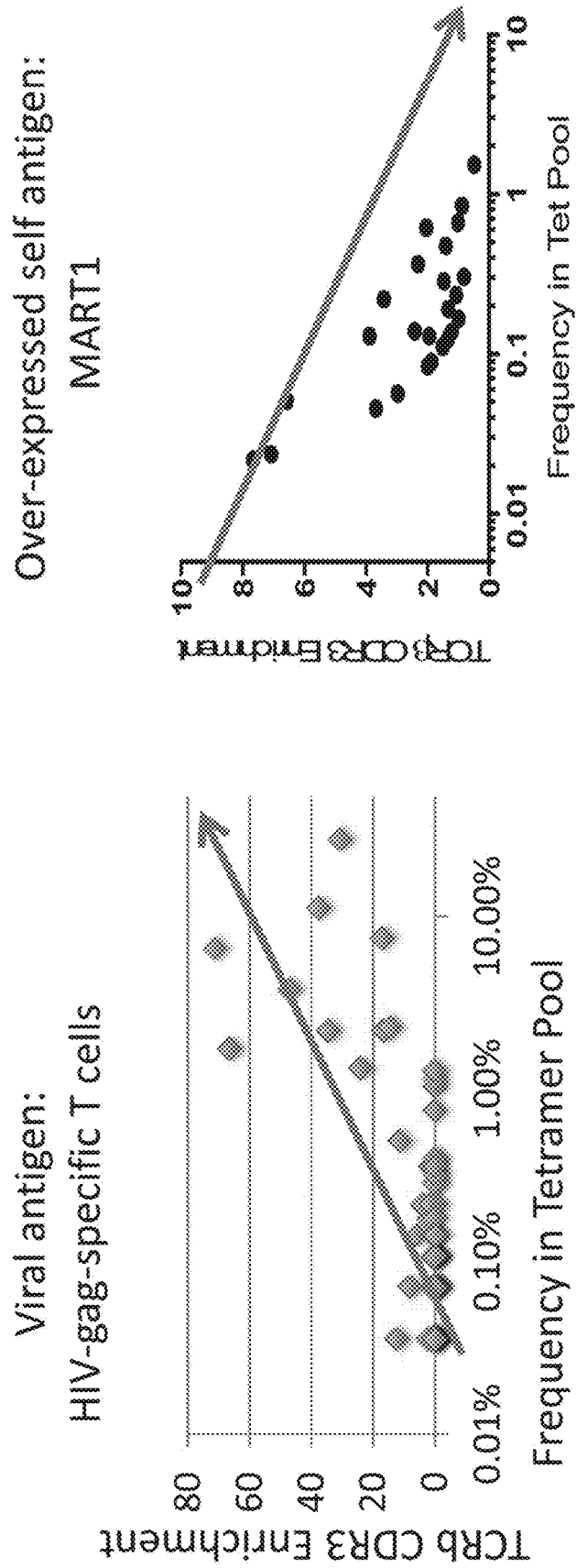
FIGS. 1A and 1B show representative data illustrating that high-affinity T cells for viral antigens are found at higher frequencies (A) than high-affinity T cells for self-antigens, which are found at very low frequencies (B).

In certain aspects, the present disclosure provides compositions comprising binding proteins specific for MAGE-A1 peptide antigens associated with a major histocompatibility complex (MHC) (e.g., human leukocyte antigen, HLA), which can be used in, for example, treating diseases or disorders associated with MAGE-A1 expression (e.g., cancer) or adoptive immunotherapy to treat cancer. In certain embodiments, the instant disclosure provides polynucleotides encoding such MAGE-A1-specific binding proteins, as well as host cells modified to express MAGE-A1-specific binding proteins (e.g., TCRs).

In other aspects, the present disclosure provides modified CD4+ T cells comprising a heterologous polynucleotide encoding a TCR from a CD8+ T cell that is capable of specifically binding to a peptide antigen (e.g., MAGE-A1) and optionally comprising a heterologous polynucleotide encoding at least an extracellular portion of a CD8 co-receptor molecule.

By way of background, most tumor targets for T cell-based immunotherapies are self-antigens since tumors arise from previously normal tissue. For example, such tumor-associated antigens (TAAs) may be expressed at high levels in a cancer cell, but may not be expressed or may be minimally expressed in other cells. During T cell development in the thymus, T cells that bind weakly to self-antigens are allowed to survive in the thymus, and can undergo further development and maturation, while T cells that bind strongly to self-antigens are eliminated by the immune system since such cells would mount an undesirable autoimmune response. Hence, T cells are sorted by their relative ability to bind to antigens to prepare the immune system to respond against a foreign invader (i.e., recognition of non-self-antigen) while at the same time preventing an autoimmune response (i.e., recognition of self-antigen). This tolerance mechanism limits naturally occurring T cells that can recognize tumor (self) antigens with high affinity and, therefore, eliminates the T cells that would effectively eliminate tumor cells. Consequently, isolating T cells having high affinity TCRs specific for tumor antigens is difficult because most such cells are essentially eliminated by the immune system.

The instant disclosure provides TCRs specific for MAGE-A1 (also called MAGE-1, MAGE family member A1, CT 1.1, and Melanoma-Antigen Gene 1) peptides, such as high affinity TCRs specific for MAGE-A1 peptides, wherein a cell expressing such a TCR is capable of binding to a MAGE-A1:HLA complex independent of CD8. In addition, such TCRs may optionally be capable of more efficiently associating with a CD3 protein as compared to endogenous TCRs.

A method was developed to quickly and simultaneously screen and rank T cell clonotypes (based on affinity) from a large cohort of HLA-matched donors in a short time (about 6-8 weeks). In certain embodiments, the instant disclosure provides methods for enriching for cells with high-affinity TCRs by using limiting concentrations of antigen-specific pMHC multimers in the presence of a subject's immune cells (e.g., PBMCs). The TCRβ repertoire and frequency analysis, coupled with bioinformatics, was used to accurately identify TCR α-chain and β-chain pairs. An advantage of these methods is that they allow for a quick comparison of the TCR affinity of thousands of clones from multiple donors as opposed to cloning individual TCRs.

The compositions and methods described herein will in certain embodiments have therapeutic utility for the treatment of diseases and conditions associated with MAGE-A1 expression. Such diseases include various forms of hyperproliferative disorders, such as hematological malignancies and solid cancers. Non-limiting examples of these and related uses are described herein and include in vitro, ex vivo and in vivo stimulation of MAGE-A1 antigen-specific T cell responses, such as by the use of recombinant T cells expressing an enhanced or high affinity TCR specific for a MAGE-A1 peptide.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" is not equivalent to "comprising" and refers to the specified materials or steps of a claim, or to those that do not materially affect the basic characteristics of a claimed subject matter. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

"Major histocompatibility complex" (MHC) refers to glycoproteins that deliver peptide antigens to a cell surface. MHC class I molecules are heterodimers having a membrane spanning α chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by CD8+ T cells. MHC class II molecules deliver peptides originating in the vesicular system to the cell surface, where they are recognized by CD4+ T cells. Human MHC is referred to as human leukocyte antigen (HLA).

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45Rβ as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$) refers to antigen-experienced CD8+ cytotoxic T lymphocytes that have decreased expression of CD62L, CCR7, CD28, and are positive for granzyme and perforin as compared to $T_{CM}$. Other exemplary T cells include regulatory T cells, such as CD4+ CD25+ (Foxp3+) regulatory T cells and Treg17 cells, as well as Tr1, Th3, CD8+ CD28−, and Qa-1 restricted T cells.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, 3$^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like immunoglobulins, the extracellular portion of TCR chains (e.g., α-chain, β-chain) contain two immunoglobulin domains, a variable domain (e.g., α-chain variable domain or $V_α$, β-chain variable domain or $V_β$; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or $C_α$, typically amino acids 117 to 259 based on Kabat, β-chain constant domain or $C_β$, typically amino acids 117 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). The $V_α$ and $V_β$ of a native TCR generally have similar structures, with each variable domain comprising four conserved FRs and three CDRs. The $V_α$ domain is encoded by two separate DNA segments, the variable gene segment and the joining gene segment (V-J); the $V_β$ domain is encoded by three separate DNA segments, the variable gene segment, the diversity gene segment, and the joining gene segment (V-D-J). A single $V_α$ or $V_β$ domain may be sufficient to confer antigen-binding specificity. Furthermore, TCRs that bind a particular antigen may be isolated using a $V_α$ or $V_β$ domain from a TCR that binds the antigen to screen a library of complementary $V_α$ or $V_β$ domains, respectively. In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

As used herein, the term "CD8 co-receptor" or "CD8" means the cell surface glycoprotein CD8, either as an alpha-alpha homodimer or an alpha-beta heterodimer. The CD8 co-receptor assists in the function of cytotoxic T cells (CD8+) and functions through signaling via its cytoplasmic tyrosine phosphorylation pathway (Gao and Jakobsen, *Immunol. Today* 21:630-636, 2000; Cole and Gao, *Cell. Mol. Immunol.* 1:81-88, 2004). There are five (5) different CD8 beta chains (see UniProtKB identifier P10966) and a single CD8 alpha chain (see UniProtKB identifier P01732). CD8 generally binds pMHC Class I complexes.

"CD4 co-receptor" or "CD4" refers to an immunoglobulin co-receptor glycoprotein that assists the TCR in communicating with antigen-presenting cells (see, Campbell & Reece, *Biology* 909 (Benjamin Cummings, Sixth Ed., 2002)). CD4 is found on the surface of immune cells such as T helper cells, monocytes, macrophages, and dendritic cells, and includes four immunoglobulin domains (D1 to D4) that are expressed at the cell surface. During antigen presentation, CD4 is recruited, along with the TCR complex, to bind to different regions of the MHCII molecule (CD4 binds MHCII β2, while the TCR complex binds MHCII α1/β1). Without wishing to be bound by theory, it is believed that close proximity to the TCR complex allows CD4-associated kinase molecules to phosphorylate the immunoreceptor tyrosine activation motifs (ITAMs) present on the cytoplasmic domains of CD3. This activity is thought to amplify the signal generated by the activated TCR in order to produce various types of T helper cells. CD4 generally binds pMHC Class II complexes.

"CD3" is a multi-protein complex of six chains (see, Abbas and Lichtman, 2003; Janeway et al., p 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Without wishing to be bound by theory, it is believed the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., MAGE-A1, MAGE-A1 peptide:MHC complex). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for their specific ability to bind to a biological molecule, a molecular complex or other target of interest.

As used herein, "specifically binds" or "specific for" refers to an association or union of a binding protein (e.g., TCR receptor) or a binding domain (or fusion protein thereof) to a target molecule with an affinity or $K_a$ (i.e., an equilibrium association constant of a particular binding interaction with units of 1/M) equal to or greater than $10^5 M^{-1}$ (which equals the ratio of the on-rate [$k_{on}$] to the off-rate [$k_{off}$] for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7 M^{-1}$, at least $10^8 M^{-1}$, at least $10^9 M^{-1}$, at least $10^{10} M^{-1}$, at least $10^{11} M^{-1}$, at least $10^{12} M^{-1}$, or at least $10^{13} M^{-1}$. "Low affinity" binding proteins or binding domains refer to those binding proteins or binding domains having a $K_a$ of up to $10^7 M^{-1}$, up to $10^6 M^{-1}$, up to $10^5 M^{-1}$. Alternatively, affinity may be defined as an equilibrium dissociation constant ($K_d$) of a particular binding interaction with units of M (e.g., $10^{-5}$M to $10^{-13}$M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate ($k_{off}$) for the target antigen that is less than that of the wild type binding domain, or a combination thereof. In certain embodiments, enhanced affinity TCRs may be codon optimized to enhance expression in a particular host cell, such as T cells (Scholten et al., *Clin. Immunol.* 119:135, 2006).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

The term "MAGE-A1-specific binding protein" refers to a protein or polypeptide that specifically binds to MAGE-A1 or a peptide or fragment thereof. In some embodiments, a MAGE-A1-specific binding protein or polypeptide binds to MAGE-A1 or a peptide thereof, such as a MAGE-A1 peptide complexed with an MHC or HLA molecule, e.g., on a cell surface, with at least, or at least about, a particular affinity. In certain embodiments, a MAGE-A1-specific binding protein binds a MAGE-A1-derived peptide:HLA complex (or MAGE-A1-derived peptide:MHC complex) with a $K_d$ of less than about $10^{-8}$M, less than about $10^{-9}$M, less than about $10^{-10}$ M, less than about $10^{-11}$M, less than about $10^{-12}$M, or less than about $10^{-13}$M, or with an affinity that is about the same as, at least about the same as, or is greater than at or about the affinity exhibited by an exemplary MAGE-A1 specific binding protein provided herein, such as any of the MAGE-A1-specific TCRs provided herein, for example, as measured by the same assay. In certain embodiments, a MAGE-A1-specific binding protein comprises a MAGE-A1-specific immunoglobulin superfamily binding protein or binding portion thereof.

Assays for assessing affinity or apparent affinity or relative affinity include, for example, measuring apparent affinity for a TCR (or for a binding protein comprising a binding domain derived from a TCR) by assessing binding to various concentrations of tetramers, for example, by flow cytometry using labeled tetramers. In some examples, apparent $K_D$ of a TCR is measured using 2-fold dilutions of labeled tetramers at a range of concentrations, followed by determination of binding curves by non-linear regression, apparent $K_D$ being determined as the concentration of ligand that yielded half-maximal binding.

The term "MAGE-A1 binding domain" or "MAGE-A1 binding fragment" refer to a domain, or portion of a MAGE-A1-specific binding protein, responsible for the specific MAGE-A1 binding. A MAGE-A1-specific binding domain alone (i.e., without any other portion of a MAGE-A1-specific binding protein) can be soluble and can bind to MAGE-A1 with a $K_d$ of less than about $10^{-8}$M, less than about $10^{-9}$M, less than about $10^{-10}$ M, less than about $10^{-11}$ M, less than about $10^{-12}$M, or less than about $10^{-13}$ M. Exemplary MAGE-A1-specific binding domains include MAGE-A1-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker) and scFv fragments as described herein, which can be derived from an anti-MAGE-A1 TCR or antibody.

Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology (8th Ed.) 2011 Garland Science, NY; chapters 6, 9 and 16). For example, processed antigen peptides originating in the cytosol (e.g., tumor antigen, intracellular pathogen) are generally from about 7 amino acids to about 11 amino acids in length and will associate with class I MHC molecules, whereas peptides processed in the vesicular system (e.g., bacterial, viral) will vary in length from about 10 amino acids to about 25 amino acids and associate with class II MHC molecules.

"MAGE-A1 antigen" or "MAGE-A1 peptide antigen" refer to a naturally or synthetically produced portion of a MAGE-A1 protein ranging in length from about 7 amino acids to about 15 amino acids, which can form a complex with a MHC (e.g., HLA) molecule and such a complex can bind with a TCR specific for a MAGE-A1 peptide:MHC (e.g., HLA) complex.

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids.

"Junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%).

As used herein, "nucleic acid" or "nucleic acid molecule" or "polynucleotide" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

As used herein, the terms "modified", "engineered", or "recombinant" refer to a cell, microorganism, nucleic acid molecule, or vector that has been genetically engineered by human intervention—that is, modified by introduction of an exogenous or heterologous nucleic acid molecule, or refers to a cell or microorganism that has been altered such that expression of an endogenous nucleic acid molecule or gene is controlled, deregulated or constitutive. Human-generated genetic alterations may include, for example, modifications that introduce nucleic acid molecules (which may include an expression control element, such as a promoter) that encode one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are described in, for example: WO 97/09433 at page 10; Lehninger, Biochemistry, $2^{nd}$ Edition; Worth Publishers, Inc. NY, NY, pp. 71-77, 1975; and Lewin, Genes IV, Oxford University Press, NY and Cell Press, Cambridge, Mass., p. 8, 1990. Conservative substitutions of amino acids may occur naturally or may be introduced when a binding protein or TCR is recombinantly produced. Amino acid substitutions, deletions, and additions may be introduced into a protein using mutagenesis methods known in the art (see, e.g., Sambrook et al., *Molecular Cloning: A Laboratory Manual,* 3d ed., Cold Spring Harbor Laboratory Press, NY, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

The term "construct" refers to any polynucleotide that contains a recombinant nucleic acid molecule. A construct may be present in a vector (e.g., a bacterial vector, a viral vector) or may be integrated into a genome.

A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

The term "operably linked" or "operatively-linked" refers to the association of two or more nucleic acid molecules on a single nucleic acid molecule or fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

The term "introduced" in the context of inserting a nucleic acid molecule into a cell, means "transfection", or 'transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" or "exogenous" nucleic acid molecule, construct or sequence refers to polynucleotide or portion of a polynucleotide that is not native to a host cell, but may be homologous to a polynucleotide or portion of a polynucleotide from the host cell. The source of the heterologous or exogenous polynucleotide, construct or sequence may be from a different genus or species. In certain embodiments, a heterologous or exogenous polynucleotide is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein or other activity encoded by an exogenous polynucleotide introduced into the host cell, even if the host cell encodes a homologous protein or activity.

As described herein, more than one heterologous or exogenous nucleic acid molecule can be introduced into a host cell as separate polynucleotides, as a plurality of individually controlled genes, as a polycistronic polynucleotide, as a single nucleic acid molecule encoding a fusion protein, or any combination thereof. For example, as disclosed herein, a host cell can be modified to express two or more heterologous or exogenous polynucleotides encoding desired TCR specific for a MAGE-A1 antigen peptide (e.g., TCRα and TCRβ). When two or more exogenous nucleic acid molecules are introduced into a host cell, it is understood that the two or more exogenous nucleic acid molecules can be introduced as a single polynucleotide (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate polynucleotides introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule may be homologous to a native host cell gene, and may optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a $CD24^{Lo}$ $Lin^-CD117^+$ phenotype or those found in the thymus (referred to as progenitor thymocytes).

As used herein, the term "host" refers to a cell (e.g., T cell) or microorganism targeted for genetic modification with a heterologous or exogenous nucleic acid molecule to produce a polypeptide of interest (e.g., high or enhanced affinity anti-MAGE-A1 TCR). In certain embodiments, a host cell may optionally already possess or be modified to include other genetic modifications that confer desired properties related or unrelated to biosynthesis of the heterologous or exogenous protein (e.g., inclusion of a detectable marker; deleted, altered or truncated endogenous TCR; increased co-stimulatory factor expression). In certain embodiments, a host cell is a human hematopoietic progenitor cell transduced with a heterologous or exogenous nucleic acid molecule encoding a TCRα chain specific for a MAGE-A1 antigen peptide.

As used herein, "hyperproliferative disorder" refers to excessive growth or proliferation as compared to a normal or undiseased cell. Exemplary hyperproliferative disorders include tumors, cancers, neoplastic tissue, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like).

Binding Proteins Specific for MAGE-A1 Antigen Peptides

In certain aspects, the present disclosure provides a modified cell comprising a heterologous polynucleotide that encodes a binding protein (e.g, a TCR, a single chain TCR (scTCR), or a CAR) that specifically binds to MAGE-A1 or a MAGE-A1 peptide antigen, such as a MAGE-A1 peptide complexed with an HLA molecule.

By way of background, ideal targets for immunotherapy are immunogenic proteins with high expression in malignant tissues and limited-to-absent expression in normal tissues. A unique group of proteins, known as cancer/testis antigens (CTAs), have been identified as promising immunotherapeutic targets due to their expression in various malignant tissues but low-level expression in healthy adult tissue except for germ cells of the testis (Ademuyiwa et al. *PLoS One*, 7(6):e38783 (2012); Badovinac Crnjevic et al., *Med Oncol.*, 29(3):1586-91 (2012); Curigliano, G. et al., *Ann. Oncol.*, 22(1):98-103 (2011). Moreover, CTAs are especially expressed in higher-grade lesions and aggressive malignancies, and associated with poorer clinical outcomes (Barrow et al., *Clin Cancer Res.*, 12(3 Pt 1):764-71 (2006); Gure, et al. *Clin Cancer Res.*, 11(22):8055-62 (2005); Velazquez et al., *Cancer Immun.*, 7: 11 (2007)). MAGE family proteins are CTAs that are broadly expressed in many tumor types such as melanoma, lung, ovarian, multiple myeloma as well as TNBC. Simpson, A. J., et al., Cancer/testis antigens, gametogenesis and cancer, *Nat. Rev. Cancer,* 2005. 5(8): 615-25; Weon, J. L. and P. R. Potts, *Curr Opin Cell Biol,* 2015. 37: 1-8; Park, T. S., et al., *J Immunother,* 2016. 39(1): 1-7; Li, X., S. C. Hughes, and R. Wevrick, *Cancer Genet,* 2015. 208(1-2):25-34; Kerkar, S. P., et al., *J Immunother,* 2016. 39(4):181-7. In particular, MAGE-A1 is expressed in 69.1% of TNBC cases overall (n=81) and in 85.7% of Grade III cases. Mrklic, I., et al., *Acta Histochem,* 2014. 116(5): 740-6. Additionally, evidence from melanoma cell lines suggests that MAGE-A1 directly drives tumorogenesis. Wang, D., et al., *Biochem Biophys Res Commun,* 2016. 473(4): 959-65.

In certain embodiments, a binding protein of the instant disclosure comprises (a) a T cell receptor (TCR) α-chain variable ($V_\alpha$) domain having a CDR3 amino acid sequence according to any one of SEQ ID NOS.:26, 32, 38, 44, 50, or 51, and a TCR β-chain variable ($V_\beta$) domain; (b) a $V_\beta$ domain having a CDR3 amino acid sequence according to any one of SEQ ID NOS.:23, 29, 35, 41, or 47, and a $V_\alpha$ domain; or (c) a $V_\alpha$ domain having a CDR3 amino acid sequence according to any one of SEQ ID NOS:26, 32, 38, 44, 50, or 51, and a $V_\beta$ domain having a CDR3 amino acid sequence according to any one of SEQ ID NOs:23, 29, 35, 41, or 47.

Peptide-MHC complexes, such as MAGE-A1 peptide: MHC complexes are recognized by and bound through the TCR Vα and TCR Vβ domains. During lymphocyte development, Vα exons are assembled from different variable and joining gene segments (V-J), and Vβ exons are assembled from different variable, diversity, and joining gene segments (V-D-J). The TCRα chromosomal locus has 70-80 variable gene segments and 61 joining gene segments. The TCRβ chromosomal locus has 52 variable gene segments, and two separate clusters of each containing a single diversity gene segment, together with six or seven joining gene segments. Functional Vα and Vβ gene exons are generated by the recombination of a variable gene segment with a joining gene segment for Vα, and a variable gene segment with a diversity gene segment and a joining gene segment for Vβ.

TCR Vα and Vβ domains each comprise three hypervariable loops, also referred to as complementary determining regions (CDRs) that contact the peptide-MHC complex. CDR1 and CDR2 are encoded within the variable gene segment, whereas CDR3 is encoded by the region spanning the variable and joining segments for Vα, or the region spanning variable, diversity, and joining segments for Vβ. Thus, if the identity of the variable gene segment of a Vα or Vβ is known (e.g., by known TRAV or TRVB alleles), the sequences of their corresponding CDR1 and CDR2 can be deduced. Moreover, certain of the presently disclosed high-affinity TCR variable regions specific for MAGE-A1 (e.g., those identified by having high-affinity CDR3 sequences) are encoded by a select TCRα allele or a TCRβ allele. In certain embodiments, an encoded binding domain comprises a $V_\beta$ domain that is derived from a TRBV30 allele, a TRBV29 allele, or a TRBV9 allele. In some embodiments, an encoded binding domain comprises a $V_\alpha$ domain that is derived from a TRAV38-1 allele, a TRAV34 allele, a TRAV16 allele, or a TRAV5 allele.

TCR variable domain sequences can be aligned to a numbering scheme (International Immunogenetics Information System (IMGT) and Aho), allowing equivalent residue positions to be annotated and for different molecules to be compared using Antigen receptor Numbering And Receptor Classification (ANARCI) software tool (2016, Bioinformatics 15:298-300). A numbering scheme provides a standardized delineation of framework regions and CDRs in the TCR variable domains.

In certain embodiments, a binding protein comprises a functional variant amino acid sequence as compared to a reference amino acid sequence disclosed herein, wherein the encoded binding protein retains binding characteristics as compared to a binding protein comprising a reference amino acid sequence. For example, in some embodiments, an encoded $V_\alpha$ domain comprises an amino acid sequence that is at least about 90% identical (e.g., is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical) to an amino acid sequence according to any one of SEQ ID NOS.:3, 7, 11, 15, and 19, and an encoded $V_\beta$ domain comprises an amino acid sequence that is at least about 90% identical to the amino acid sequence according to any one of SEQ ID NOS.:1, 5, 9, 13, 17, provided that (a) at least three or four of the CDRs have no change in sequence, wherein the CDRs that do have sequence changes have only up to two amino acid substitutions, up to a contiguous five amino acid deletion, or a combination thereof, and (b) the encoded binding protein remains capable of specifically binding to a MAGE-A1 peptide:HLA cell surface complex independent, or in the absence, of CD8.

In particular embodiments, (a) a $V_\alpha$ domain comprises (i) a CDR1 amino acid sequence according to any one of SEQ ID NOS:24, 30, 36, 42, and 48, and/or (ii) a CDR2 amino acid sequence according to any one of SEQ ID NOS:25, 31, 37, 43, and 49; and/or (b) an encoded $V_\beta$ domain comprises (iii) a CDR1 amino acid sequence according to any one of SEQ ID NOS:21, 27, 33, 39, and 45, and/or (iv) a CDR2 amino acid sequence according to any one of SEQ ID NOS:22, 28, 34, 40, and 46. In further embodiments, an encoded binding protein comprises: (a) Vα CDR1, CDR2, and CDR3 amino acid sequences according to SEQ ID NOS:24-26, respectively, and Vβ CDR1, CDR2, and CDR3 amino acid sequences according to SEQ ID NOS:21-23, respectively; (b) Vα CDR1, CDR2, and CDR3 amino acid sequences according to SEQ ID NOS:30-32, respectively, and Vβ CDR1, CDR2, and CDR3 amino acid sequences according to SEQ ID NOS:27-29, respectively; (c) Vα CDR1, CDR2, and CDR3 amino acid sequences according to SEQ ID NOS:36-38, respectively, and Vβ CDR1, CDR2, and CDR3 amino acid sequences according to SEQ ID NOS:33-35, respectively; (d) Vα CDR1, CDR2, and CDR3 amino acid sequences according to SEQ ID NOS:42-44, respectively, and Vβ CDR1, CDR2, and CDR3 amino acid sequences according to SEQ ID NOS:39-41, respectively; or (e) Vα CDR1, CDR2, and CDR3 amino acid sequences according to SEQ ID NOS:48-50, respectively, and Vβ CDR1, CDR2, and CDR3 amino acid sequences according to SEQ ID NOS:45-47, respectively.

In certain embodiments, a Vα domain comprises or consists of an amino acid sequence according to SEQ ID NO.:3, 7, 11, 15, or 19. In further embodiments, an encoded Vβ domain comprises or consists of an amino acid sequence according to SEQ ID NO.:1, 5, 9, 13, or 17.

In some embodiments, a binding protein comprises a TCR α-chain constant domain, a TCR β-chain constant domain, or both. In certain embodiments, a TCR α-chain constant (Cα) domain has at least 90% sequence identity to the amino acid sequence of any one of SEQ ID NO.:4, 8, 12, 16, or 20. In further embodiments, a TCR β-chain constant (Cβ) domain has at least 90% sequence identity to any one of the amino acid sequences of SEQ ID NO.:2, 6, 10, 14, or 18.

Accordingly, in some embodiments, a binding of the present disclosure comprises a $V_\alpha$ domain, a $V_\beta$ domain, a $C_\alpha$ domain, and a $C_\beta$ domain. In further embodiments, a binding protein comprises Vα domain comprising or consisting of SEQ ID NO.:3, a Vβ domain comprising or consisting of SEQ ID NO.:1, a Cα domain comprising or consisting of SEQ ID NO.:4, and a Cβ domain comprising or consisting of SEQ ID NO.:2. In other embodiments, a binding protein comprises a Vα domain comprising or consisting of SEQ ID NO.:7, a Vβ domain comprising or consisting of SEQ ID NO.:5, a Cα domain comprising or consisting of SEQ ID NO.:8, and a Cβ comprising or consisting of SEQ ID NO.:6. In still further embodiments, a binding protein comprises a Vα domain comprising or consisting of SEQ ID NO.:11, a Vβ domain comprising or consisting of SEQ ID NO.:9, a Cα domain comprising or consisting of SEQ ID NO.:12, and a Cβ domain comprising or consisting of SEQ ID NO.:10. In other embodiments, a binding protein comprises a Vα domain comprising or consisting of SEQ ID NO.:15, a Vβ domain comprising or consisting of SEQ ID NO.: 13, a Cα comprising or consisting of SEQ ID NO.: 16, and a Cβ domain comprising or consisting of SEQ ID NO.:14. In yet other embodiments, a binding protein comprises a Vα domain comprising or consisting of SEQ ID NO.: 19, a Vβ domain comprising or consisting of SEQ ID NO.:17, a Cα domain comprising or consisting of SEQ ID NO.:20, and a Cβ domain comprising or consisting of SEQ ID NO.: 18.

In any of the embodiments disclosed herein, a binding protein (e.g., in soluble form or expressed on a cell surface of a modified cell of the present disclosure) is capable of binding to a MAGE-A1:HLA-A*201 complex (e.g., a KVLEYVIKV (SEQ ID NO.:123):HLA-A*201 complex) on a cell surface independent of or in the absence of CD8.

In certain embodiments, any of the aforementioned MAGE-A1 specific binding proteins are each a T cell receptor (TCR), a chimeric antigen receptor or an antigen-binding fragment of a TCR, any of which can be chimeric, humanized or human. In further embodiments, an antigen-binding fragment of the TCR comprises a single chain TCR (scTCR) or a chimeric antigen receptor (CAR). In certain embodiments, a MAGE-A1 specific binding protein is a TCR, optionally a scTCR. Methods for producing engineered TCRs are described in, for example, Bowerman et al., *Mol. Immunol.*, 46(15):3000 (2009), the techniques of which are herein incorporated by reference. In certain embodiments, a MAGE-A1-specific binding domain is a CAR comprising a MAGE-A1-specific TCR binding domain (see, e.g., Walseng et al., *Scientific Reports* 7:10713 (2017), the TCR CAR constructs of which are hereby incorporated by reference in their entirety). Methods for making CARs are also described, for example, in U.S. Pat. Nos. 6,410,319; 7,446,191; U.S. Patent Publication No. 2010/065818; U.S. Pat. No. 8,822,647; PCT Publication No. WO 2014/031687; U.S. Pat. No. 7,514,537; and Brentjens et al., 2007, *Clin. Cancer Res.* 13:5426, the techniques of which are herein incorporated by reference.

Methods useful for isolating and purifying recombinantly produced soluble TCR, by way of example, may include obtaining supernatants from suitable host cell/vector systems that secrete the recombinant soluble TCR into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant soluble TCR described herein include batch cell culture, which is monitored and controlled to maintain appropriate culture conditions. Purification of the soluble TCR may be performed according to methods described herein and known in the art and that comport with laws and guidelines of domestic and foreign regulatory agencies.

In certain embodiments, nucleic acid molecules encoding a binding protein or high affinity TCR specific for MAGE-A1 are used to transfect/transduce a host cell (e.g., T cells) for use in adoptive transfer therapy. Advances in TCR sequencing have been described (e.g., Robins et al., *Blood* 114:4099, 2009; Robins et al., *Sci. Translat. Med.* 2:47ra64, 2010; Robins et al., (September 10) *J. Imm. Meth. Epub ahead of print*, 2011; Warren et al., *Genome Res.* 21:790, 2011) and may be employed in the course of practicing the embodiments according to the present disclosure. Similarly, methods for transfecting/transducing T cells with desired nucleic acids have been described (e.g., U.S. Patent Application Pub. No. US 2004/0087025) as have adoptive transfer procedures using T-cells of desired antigen-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein, including those directed to high affinity TCRs specific for MAGE-A1 peptide antigens complexed with an HLA receptor.

MAGE-A1-specific binding proteins or domains as described herein may be functionally characterized according to any of a large number of art accepted methodologies for assaying T cell activity, including determination of T cell binding, activation or induction and also including determination of T cell responses that are antigen-specific. Examples include determination of T cell proliferation, T cell cytokine release, antigen-specific T cell stimulation, MHC restricted T cell stimulation, CTL activity (e.g., by detecting $^{51}$Cr release from pre-loaded target cells), changes in T cell phenotypic marker expression, and other measures of T-cell functions. Procedures for performing these and similar assays are may be found, for example, in Lefkovits (*Immunology Methods Manual: The Comprehensive Sourcebook of Techniques*, 1998). See, also, *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein.

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen (e.g., MAGE-A1), wherein the complex is capable of binding T cell receptors specific for the cognate antigen. Each of the MHC molecules may be tagged with a biotin molecule. Biotinylated MHC/peptides are tetramerized by the addition of streptavidin, which can be fluorescently labeled. The tetramer may be detected by flow cytometry via the fluorescent label. In certain embodiments, an MHC-peptide tetramer assay is used to detect or select enhanced affinity TCRs of the instant disclosure.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

Polynucleotides and Vectors

In another aspect, isolated or recombinant polynucleotides are provided herein, wherein a polynucleotide encodes a binding protein of the present disclosure (e.g., immunoglobulin superfamily binding protein, such as a TCR, scTCR, or CAR) specific for 5T4, and wherein the polynucleotide is codon optimized for expression in a host cell (e.g., an immune cell of the present disclosure). Also provided are vectors (e.g., expression vectors) that comprise a polynucleotide of this disclosure, wherein the polynucleotide is operatively associated or operably linked to an expression control sequence (e.g., a promoter). Construction of an expression vector to produce a binding protein specific for a MAGE-A1 peptide of this disclosure can be made using restriction endonuclease digestion, ligation, transformation, plasmid purification, DNA sequencing, or a combination thereof, as described in, for example, Sambrook et al. (1989 and 2001 editions; *Molecular Cloning: A Laboratory Manual*, Cold Spring Harbor Laboratory Press, NY) and Ausubel et al. (Current Protocols in Molecular Biology, 2003). For efficient transcription and translation, a polynucleotide contained in an expression construct includes at least one appropriate expression control sequence (also called a regulatory sequence), such as a leader sequence and particularly a promoter operably (i.e., operatively) linked to the nucleotide sequence encoding the binding protein of this disclosure.

A nucleic acid may be a single- or a double-stranded DNA, cDNA or RNA in any form, and may include a positive and a negative strand of the nucleic acid which complement each other, including anti-sense DNA, cDNA and RNA. Also included are siRNA, microRNA, RNA-DNA hybrids, ribozymes, and other various naturally occurring or synthetic forms of DNA or RNA.

Isolated or recombinant nucleic acid molecules encoding a binding protein (e.g., immunoglobulin superfamily binding protein) or high affinity recombinant T cell receptor (TCR) specific for MAGE-A1 as described herein may be produced and prepared according to various methods and techniques of the molecular biology or polypeptide purification arts.

In certain embodiments, an isolated polynucleotide is provided that encodes a binding protein having a TCR Vα domain and a TCR Vβ domain, wherein the encoded binding protein is capable of specifically binding to a MAGE-A1 peptide:HLA complex on a cell surface independent of CD8 or in the absence of CD8, the isolated polynucleotide comprising: (a) a Vα CDR3-encoding polynucleotide according to SEQ ID NO:97, 103, 109, 115 or 121, and a Vβ-encoding polynucleotide; (b) a Vβ CDR3-encoding polynucleotide according to SEQ ID NO:94, 100, 106, 112, or 118, and a Vα-encoding polynucleotide; or (c) a Vα CDR3-encoding polynucleotide according to SEQ ID NO:97, 103, 109, 115 or 121 and a Vβ CDR3-encoding polynucleotide according to SEQ ID NO:94, 100, 106, 112, or 118. In further embodiments, a Vβ-encoding polynucleotide is derived from a TRBV30 allele, a TRBV29 allele, or a TRBV9 allele. In some embodiments, a Vα-encoding polynucleotide is derived from a TRAV38-1 allele, a TRAV34 allele, a TRAV16 allele, or a TRAV5 allele.

Presently disclosed polynucleotides encoding binding proteins can, in some embodiments, comprise: (a) a $V_\alpha$ CDR3-encoding polynucleotide according to SEQ ID NO:97 and a $V_\beta$ CDR3-encoding polynucleotide according to SEQ ID NO:94; (b) a $V_\alpha$ CDR3-encoding polynucleotide according to SEQ ID NO:103 and a $V_\beta$ CDR3-encoding polynucleotide according to SEQ ID NO:100; (c) a $V_\alpha$ CDR3-encoding polynucleotide according to SEQ ID NO:109 and a V$_\beta$ CDR3-encoding polynucleotide according to SEQ ID NO:106; (d) a V$_\alpha$ CDR3-encoding polynucleotide according to SEQ ID NO:115 and a V$_\beta$ CDR3-encoding polynucleotide according to SEQ ID NO:112; or (e) a V$_\alpha$ CDR3-encoding polynucleotide according to SEQ ID NO:121 and a V$_\beta$ CDR3-encoding polynucleotide according to SEQ ID NO:118. In certain embodiments, an isolated polynucleotide encoding a binding protein further comprises (a) a V$\alpha$ CDR1-encoding polynucleotide according to SEQ ID NO:95, 101, 107, 113 or 119; (b) a V$\alpha$ CDR2-encoding polynucleotide according to SEQ ID NO:96, 102, 108, 114 or 120; (c) a CDR1-encoding polynucleotide according to SEQ ID NO:92, 98, 104, 110 or 116; and/or (d) a V$\beta$ CDR2-encoding polynucleotide according to SEQ ID NO:93, 99, 105, 111 or 117.

In particular embodiments, an isolated polynucleotide encoding a binding protein of the present disclosure comprises (a) a V$\alpha$ CDR1-encoding polynucleotide according to SEQ ID NO:95, a V$\alpha$ CDR2-encoding polynucleotide according to SEQ ID NO:96, a V$\alpha$ CDR3-encoding polynucleotide according to SEQ ID NO:97, a V$\beta$ CDR1-encoding polynucleotide according to SEQ ID NO:92, a V$\beta$ CDR2-encoding polynucleotide according to SEQ ID NO:93, and V$\beta$ CDR3-encoding polynucleotide according to SEQ ID NO:94; (b) a V$\alpha$ CDR1-encoding polynucleotide according to SEQ ID NO:101, a V$\alpha$ CDR2-encoding polynucleotide according to SEQ ID NO:102, a V$\alpha$ CDR3-encoding polynucleotide according to SEQ ID NO:103, a V$\beta$ CDR1-encoding polynucleotide according to SEQ ID NO:98, a V$\beta$ CDR2-encoding polynucleotide according to SEQ ID NO:99, and V$\beta$ CDR3-encoding polynucleotide according to SEQ ID NO:100; (c) a V$\alpha$ CDR1-encoding polynucleotide according to SEQ ID NO:107, a V$\alpha$ CDR2-encoding polynucleotide according to SEQ ID NO:108, a V$\alpha$ CDR3-encoding polynucleotide according to SEQ ID NO:109, a V$\beta$ CDR1-encoding polynucleotide according to SEQ ID NO:104, a V$\beta$ CDR2-encoding polynucleotide according to SEQ ID NO:105, and V$\beta$ CDR3-encoding polynucleotide according to SEQ ID NO:106; (d) a V$\alpha$ CDR1-encoding polynucleotide according to SEQ ID NO:113, a V$\alpha$ CDR2-encoding polynucleotide according to SEQ ID NO:114, a V$\alpha$ CDR3-encoding polynucleotide according to SEQ ID NO:115, a V$\beta$ CDR1-encoding polynucleotide according to SEQ ID NO:110, a V$\beta$ CDR2-encoding polynucleotide according to SEQ ID NO:111, and V$\beta$ CDR3-encoding polynucleotide according to SEQ ID NO:112; or (e) a V$\alpha$ CDR1-encoding polynucleotide according to SEQ ID NO:119, a V$\alpha$ CDR2-encoding polynucleotide according to SEQ ID NO:120, a V$\alpha$ CDR3-encoding polynucleotide according to SEQ ID NO:121, a V$\beta$ CDR1-encoding polynucleotide according to SEQ ID NO:116, a V$\beta$ CDR2-encoding polynucleotide according to SEQ ID NO:117, and V$\beta$ CDR3-encoding polynucleotide according to SEQ ID NO:118.

In some embodiments, the instant disclosure provides a polynucleotide encoding a binding protein, wherein a V$_\alpha$-encoding polynucleotide comprises a nucleotide sequence having at least 80% identity (e.g., at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identity) to SEQ ID NO:58, 66, 74, 82, or 90, and a V$_\beta$-encoding polynucleotide comprises a nucleotide sequence having at least 80% identity to SEQ ID NO:56, 64, 72, 80, or 88. In further embodiments: (a) a V$\alpha$-encoding polynucleotide comprises a nucleotide sequence having at least 80% identity to SEQ ID NO:58 and a V$\beta$-encoding polynucleotide comprises a nucleotide sequence having at least 80% identity to SEQ ID NO:56; (b) a V$\alpha$-encoding polynucleotide comprises a nucleotide sequence having at least 80% identity to SEQ ID NO:66 and a V$\beta$-encoding polynucleotide comprises a nucleotide sequence having at least 80% identity to SEQ ID NO:64; (c) a V$\alpha$-encoding polynucleotide comprises a nucleotide sequence having at least 80% identity to SEQ ID NO:74 and a V$\beta$-encoding polynucleotide comprises a nucleotide sequence having at least 80% identity to SEQ ID NO:72; (d) a V$\alpha$-encoding polynucleotide comprises a nucleotide sequence having at least 80% identity to SEQ ID NO:82 and a V$\beta$-encoding polynucleotide comprises a nucleotide sequence having at least 80% identity to SEQ ID NO:80; or (e) a V$\alpha$-encoding polynucleotide comprises a nucleotide sequence having at least 80% identity to SEQ ID NO:90 and a V$\beta$-encoding polynucleotide comprises a nucleotide sequence having at least 80% identity to SEQ ID NO:88.

In particular embodiments, (a) a V$\alpha$-encoding polynucleotide comprises or consists of a nucleotide sequence according to SEQ ID NO:58 and a V$\beta$-encoding polynucleotide comprises or consists of a nucleotide sequence according to SEQ ID NO:56; (b) a V$\alpha$-encoding polynucleotide comprises or consists of a nucleotide sequence according to SEQ ID NO:66 and a V$\beta$-encoding polynucleotide comprises or consists of a nucleotide sequence according to SEQ ID NO:64; (c) a V$\alpha$-encoding polynucleotide comprises or consists of a nucleotide sequence according to SEQ ID NO:74 and a V$\beta$-encoding polynucleotide comprises or consists of a nucleotide sequence according to SEQ ID NO:72; (d) a V$\alpha$-encoding polynucleotide comprises or consists of a nucleotide sequence according to SEQ ID NO:82 and a V$\beta$-encoding polynucleotide comprises or consists of a nucleotide sequence according to SEQ ID NO:80; or (e) a V$\alpha$-encoding polynucleotide comprises or consists of a nucleotide sequence according to SEQ ID NO:90 and a V$\beta$-encoding polynucleotide comprises or consists of a nucleotide sequence according to SEQ ID NO:88.

Binding protein-encoding polynucleotides of the instant disclosure may, in certain embodiments, further comprise a polynucleotide that encodes a TCR $\alpha$-chain constant domain, a polynucleotide that encodes a TCR $\beta$-chain constant domain, or both. In some embodiments, an isolated polynucleotide encoding a binding protein of the present disclosure further comprises: (a) a C$_\alpha$-domain-encoding polynucleotide having at least 80% identity to SEQ ID NO:59, 67, 75, 83, or 91; and/or (b) a C$_\beta$-domain-encoding polynucleotide having at least 80% identity to SEQ ID NO:57, 65, 73, 81, or 89. In further embodiments, a C$_\alpha$-domain-encoding polynucleotide comprises or consists of a nucleotide sequence according to SEQ ID NO:59, 67, 75, 83, or 91, and aC$_\beta$-domain-encoding polynucleotide comprises or consists of a nucleotide sequence according to SEQ ID NO:57, 65, 73, 81, or 89.

In particular embodiments, an isolated polynucleotide encoding a binding protein of the present disclosure comprises: (a) a V$_\alpha$-encoding polynucleotide according to SEQ ID NO:58, a V$_\beta$-encoding polynucleotide according to SEQ ID NO:56, a C$_\alpha$-domain-encoding polynucleotide according to SEQ ID NO:59, and a C$_\beta$-domain-encoding polynucleotide according to SEQ ID NO:57; (b) a V$_\alpha$-encoding polynucleotide according to SEQ ID NO:66, a V$_\beta$-encoding polynucleotide according to SEQ ID NO:64, a C$_\alpha$-domain-encoding polynucleotide according to SEQ ID NO:67, and a C$_\beta$-domain-encoding polynucleotide according to SEQ ID NO:65; (c) a V$_\alpha$-encoding polynucleotide according to SEQ ID NO:74, a V$_\beta$-encoding polynucleotide according to SEQ ID NO:72, a C$_\alpha$-domain-encoding polynucleotide according to SEQ ID NO:75, and a C$_\beta$-domain-encoding polynucleotide according to SEQ ID NO:73; (d) a V$_\alpha$-encoding polynucleotide according to SEQ ID NO:82, a V$_\beta$-encoding polynucleotide according to SEQ ID NO:80, a C$_\alpha$-domain-encoding polynucleotide according to SEQ ID NO:83, and a C$_\beta$-domain-encoding polynucleotide according to SEQ ID NO:81; or (e) a V$_\alpha$-encoding polynucleotide according to SEQ ID NO:90, a V$_\beta$-encoding polynucleotide according to SEQ ID NO:88, a C$_\alpha$-domain-encoding polynucleotide according to SEQ ID NO:91, and a C$_\beta$-domain-encoding polynucleotide according to SEQ ID NO:89.

In further embodiments, two or more substituent gene products of a binding protein of this disclosure are expressed as a single peptide with the parts separated by a cleavable or removable segment. For instance, self-cleaving peptides useful for expression of separable polypeptides encoded by a single polynucleotide or vector are known in the art and include, for example, a Porcine teschovirus-1 2A (P2A) peptide, such as a peptide encoded by a polynucleotide having the nucleotide sequence shown in any one of SEQ ID NOS:128 or 129, a Thoseaasigna virus 2A (T2A) peptide, such as a peptide encoded by a polynucleotide having the nucleotide sequence shown in SEQ ID NO:132, an Equine rhinitis A virus (ERAV) 2A (E2A) peptide, such as a peptide encoded by a polynucleotide having the nucleotide sequence shown in SEQ ID NO:131, and a Foot-and-Mouth disease virus 2A (F2A) peptide, such as a peptide encoded by a polynucleotide having the nucleotide sequence shown in SEQ ID NO:130.

Accordingly, in certain embodiments, an isolated polynucleotide encoding a binding protein of the instant disclosure further comprises a polynucleotide encoding a self-cleaving peptide disposed between a TCR α-chain-encoding polynucleotide and a TCR β-chain-encoding polynucleotide, or disposed between a TCR Vβ domain-encoding polynucleotide and a TCR Vα-encoding polynucleotide, or disposed between a TCR variable domain-encoding polynucleotide and a TCR constant domain-encoding polynucleotide, or any combination thereof. In particular embodiments, a polynucleotide encoding a self-cleaving peptide comprises or consists of a nucleotide sequence according to any one of SEQ ID NOS.:128-132. In further embodiments, a polynucleotide encodes a self-cleaving peptide comprising or consisting of an amino acid sequence according to any one of SEQ ID NOS.:124-127.

Also provided herein are vectors containing polynucleotides of the instant disclosure. Construction of an expression vector that is used for recombinantly producing a binding protein or high affinity engineered TCR specific for a MAGE-A1 peptide of interest can be accomplished by using any suitable molecular biology engineering techniques, including the use of restriction endonuclease digestion, ligation, transformation, plasmid purification, and DNA sequencing as described in, for example, Sambrook et al. (1989 and 2001 editions; *Molecular Cloning: A Laboratory Manual*, Cold Spring Harbor Laboratory Press, NY) and Ausubel et al. (Current Protocols in Molecular Biology, 2003). To obtain efficient transcription and translation, a polynucleotide in each recombinant expression construct includes at least one appropriate expression control sequence, such as a promoter operably (i.e., operatively) linked to a nucleotide sequence encoding a binding protein. In addition, a polynucleotide encoding a binding protein of this disclosure may also include a sequence encoding a leader sequence at the amino-terminus of the binding protein (also referred to as a pre-binding protein), which leader sequence may be removed by the cell to produce a mature binding protein.

An exemplary vector may comprise a nucleic acid molecule capable of transporting another nucleic acid molecule to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector)). Additionally, some vectors are capable of directing the expression of genes to which they are operatively linked (these vectors may be referred to as "expression vectors"). According to related embodiments, it is further understood that, if one or more agents (e.g., polynucleotides encoding binding proteins or high affinity recombinant TCRs specific for MAGE-A1 or variants thereof, as described herein) is co-administered to a subject, that each agent may reside in separate or the same vectors, and multiple vectors (each containing a different agent the same agent) may be introduced to a cell or cell population or administered to a subject.

In certain embodiments, a polynucleotide encoding binding proteins or high affinity recombinant TCRs specific for MAGE-A1 may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest. In certain embodiments, polynucleotides encoding binding proteins of the instant disclosure are contained in an expression vector that is a viral vector, such as a lentiviral vector or a γ-retroviral vector.

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

In particular embodiments, a recombinant or engineered expression vector is delivered to an appropriate cell (i.e., is capable of delivering a binding protein-encoding polynucleotide of the present disclosure to a host cell), for example, a T cell or an antigen-presenting cell, i.e., a cell that displays a peptide/MHC complex on its cell surface (e.g., a dendritic cell) and lacks CD8. In certain embodiments, a host cell is a hematopoietic progenitor cell or a human immune system cell. For example, an immune system cell can be a CD4+ T cell, a CD8+ T cell, a CD4− CD8− double negative T cell, a γδ T cell, a natural killer cell, a dendritic cell, or any combination thereof. In certain embodiments, wherein a T cell is the host, the T cell can be naïve, a central memory T cell, an effector memory T cell, or any combination thereof. Recombinant expression vectors of the present disclosure may therefore also include, for example, lymphoid tissue-specific transcriptional regulatory elements (TREs), such as a B lymphocyte, T lymphocyte, or dendritic cell specific TREs. Lymphoid tissue specific TREs are known in the art (see, e.g., Thompson et al., *Mol. Cell. Biol.* 12:1043, 1992); Todd et al., *J. Exp. Med.* 177:1663, 1993); Penix et al., *J. Exp. Med.* 178:1483, 1993).

In addition to vectors, certain embodiments relate to host cells that comprise the vectors that are presently disclosed. One of skill in the art readily understands that many suitable host cells are available in the art. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

Host Cells

Also provided are host cells (i.e., modified cells) that include a heterologous polynucleotide encoding a binding protein of this disclosure. In certain embodiments, a host cell comprises a human immune cell such as, for example, a T cell, a NK cell, or a NK-T cell. In some embodiments, a host cell comprises a CD4+ T cell, a CD8+ T cell, or both. Methods for transfecting/transducing T cells with desired nucleic acids have been described (e.g., U.S. Patent Application Pub. No. US 2004/0087025) as have adoptive transfer procedures using T cells of desired target-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein.

In certain embodiments, a modified cell comprises a heterologous polynucleotide encoding a binding protein, wherein the encoded binding protein comprises: (a) a T cell receptor (TCR) α-chain variable ($V_\alpha$) domain having a CDR3 amino acid sequence according to any one of SEQ ID NOS.:26, 32, 38, 44, 50, or 51, and a TCR β-chain variable ($V_\beta$) domain; (b) a $V_\beta$ domain having a CDR3 amino acid sequence according to any one of SEQ ID NOS.:23, 29, 35, 41, or 47, and a $V_\alpha$ domain; or (c) a $V_\alpha$ domain having a CDR3 amino acid sequence according to any one of SEQ ID NOS:26, 32, 38, 44, 50, or 51, and a $V_\beta$ domain having a CDR3 amino acid sequence according to any one of SEQ ID NOs:23, 29, 35, 41, or 47; and wherein the binding protein is capable of specifically binding to a MAGE-A1 peptide:HLA complex on a cell surface independent of CD8 or in the absence of CD8. In some embodiments, the encoded binding protein is capable of specifically binding to a KVLEYVIKV (SEQ ID NO.:123):human leukocyte antigen (HLA) complex with a $K_d$ less than or equal to about $10^{-8}$M.

Any appropriate method can be used to transfect or transduce the cells, for example, the T cells, or to administer the polynucleotides or compositions of the present methods. Known methods for delivering polynucleotides to host cells include, for example, use of cationic polymers, lipid-like molecules, and certain commercial products such as, for example, IN-VIVO-JET PEI. Other methods include ex vivo transduction, injection, electroporation, DEAE-dextran, sonication loading, liposome-mediated transfection, receptor-mediated transduction, microprojectile bombardment, transposon-mediated transfer, and the like. Still further methods of transfecting or transducing host cells employ vectors, described in further detail herein.

In any of the foregoing embodiments, a host cell (e.g., an immune cell) may be a "universal donor" cell that is modified to reduce or eliminate expression of one or more endogenous genes that encode a polypeptide involved in immune signaling or other related activities. Exemplary gene knockouts include those that encode PD-1, LAG-3, CTLA4, TIM3, an HLA molecule, a TCR molecule, or the like. Without wishing to be bound by theory, certain endogenously expressed immune cell proteins may be recognized as foreign by an allogeneic host receiving the host immune cells, which may result in elimination of the host immune cells (e.g., an HLA allele), or may downregulate the immune activity of a modified cell (e.g., PD-1, LAG-3, CTLA4), or may interfere with the binding activity of a heterologously expressed binding protein of the present disclosure (e.g., an endogenous TCR that binds a non-MAGE-A1 antigen and thereby interferes with the modified cell binding a cell that expresses MAGE-A1 antigen). Accordingly, decreasing or eliminating expression or activity of such endogenous genes or proteins can improve the activity, tolerance, and persistence of modified cells within an allogeneic host, and allows for universal, "off-the-shelf" cells for administration (e.g., to any recipient regardless of HLA type).

In certain embodiments, a host cell (e.g., a modified immune cell) of this disclosure comprises a chromosomal gene knockout of one or more of a gene that encodes PD-1, LAG-3, CTLA4, TIM3, an HLA component (e.g., a gene that encodes an α1 macroglobulin, an α2 macroglobulin, an α3 macroglobulin, a β1 microglobulin, or a β2 microglobulin), or a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013), the gene editing techniques and compositions of which are herein incorporated by reference in their entirety). As used herein, the term "chromosomal gene knockout" refers to a genetic alteration in a modified cell that prevents production, by the modified cell, of a functionally active endogenous polypeptide product. Alterations resulting in a chromosomal gene knockout can include, for example, introduced nonsense mutations (including the formation of premature stop codons), missense mutations, gene deletion, and strand breaks, as well as the heterologous expression of inhibitory nucleic acid molecules that inhibit endogenous gene expression in the modified cell.

A chromosomal gene knockout may be introduced by chromosomal editing of the immune cell. In certain embodiments, the chromosomal gene knockout is made by chromosomal editing of the immune cell. Chromosomal editing can be performed using, for example, endonucleases. As used herein "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for gene "knock-in" to inactivate a target gene. NHEJ is an error-prone repair process that often results in changes to the DNA sequence at the site of the cleavage, e.g., a substitution, deletion, or addition of at least one nucleotide. NHEJ may be used to "knock-out" a target gene. Methods of disrupting or knocking out genes or gene expression in immune cells using endonucleases are known in the art and described, for example, in PCT Publication Nos. WO 2015/066262; WO 2013/074916; and WO 2014/059173; methods from each of which is incorporated by reference. Examples of endonucleases include zinc finger nucleases, TALE-nucleases, CRISPR-Cas nucleases, and meganucleases.

As used herein, a "zinc finger nuclease" (ZFN) refers to a fusion protein comprising a zinc finger DNA-binding domain fused to a non-specific DNA cleavage domain, such as a FokI endonuclease. Each zinc finger motif of about 30 amino acids binds to about 3 base pairs of DNA, and amino acids at certain residues can be changed to alter triplet sequence specificity (see, e.g., Desjarlais et al., *Proc. Natl. Acad. Sci.* 90:2256-2260, 1993; Wolfe et al., *J. Mol. Biol.* 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, a gene knockout comprises an insertion, a deletion, a mutation or a combination thereof, made using a ZFN molecule.

As used herein, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" is composed of one or more TALE repeat domains/units, each generally having a highly conserved 33-35 amino acid sequence with divergent $12^{th}$ and $13^{th}$ amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known (see, e.g., U.S. Patent Publication No. US 2011/0301073, which atypical RVDs are incorporated by reference herein in its entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, a gene knockout comprises an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., *Science* 337:816-21, 2012). Further, the region of the guide RNA complementary to the target site can be altered or programed to target a desired sequence (Xie et al., PLOS One 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/071474; the techniques and compositions of each of which are incorporated by reference). In certain embodiments, a gene knockout comprises an insertion, a deletion, a mutation or a combination thereof, and made using a CRISPR/Cas nuclease system.

As used herein, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG, GIY-YIG, HNH, His-Cys box and PD-(D/E)XK. Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., *Nucleic Acids Res.* 25:3379-3388, 1997; Dujon et al., *Gene* 82:115-118, 1989; Perler et al., *Nucleic Acids Res.* 22:1125-1127, 1994; Jasin, *Trends Genet.* 12:224-228, 1996; Gimble et al., *J. Mol. Biol.* 263:163-180, 1996; Argast et al., *J. Mol. Biol.* 280:345-353, 1998).

In certain embodiments, naturally-occurring meganucleases may be used to promote site-specific genome modification of a target selected from PD-1, LAG3, TIM3, CTLA4, an HLA-encoding gene, or a TCR component-encoding gene. In other embodiments, an engineered meganuclease having a novel binding specificity for a target gene is used for site-specific genome modification (see, e.g., Porteus et al., *Nat. Biotechnol.* 23:967-73, 2005; Sussman et al., *J. Mol. Biol.* 342:31-41, 2004; Epinat et al., *Nucleic Acids Res.* 31:2952-62, 2003; Chevalier et al., *Molec. Cell* 10:895-905, 2002; Ashworth et al., *Nature* 441:656-659, 2006; Paques et al., *Curr. Gene Ther.* 7:49-66, 2007; U.S. Patent Publication Nos. US 2007/0117128; US 2006/0206949; US 2006/0153826; US 2006/0078552; and US 2004/0002092).

In certain embodiments, a chromosomal gene knockout comprises an inhibitory nucleic acid molecule that is introduced into a modified cell comprising a heterologous polynucleotide encoding an antigen-specific receptor that specifically binds to a tumor associated antigen, wherein the inhibitory nucleic acid molecule encodes a target-specific inhibitor and wherein the encoded target-specific inhibitor inhibits endogenous gene expression (i.e., of PD-1, TIM3, LAG3, CTLA4, an HLA component, a TCR component, or any combination thereof) in the modified cell.

A chromosomal gene knockout can be confirmed directly by DNA sequencing of the modified cell following use of the knockout procedure or agent. Chromosomal gene knockouts can also be inferred from the absence of gene expression (e.g., the absence of an mRNA or polypeptide product encoded by the gene) following the knockout.

In some embodiments, a modified cell is a CD4$^+$ T cell that comprises a heterologous polynucleotide encoding a binding protein of the present disclosure (e.g., a MAGE-A1-specific TCR from a CD8$^+$ T cell that is capable of specifically binding to a peptide antigen). In some embodiments, a heterologously encoded TCR of a modified CD4$^+$ T cell is a high-affinity TCR. In particular embodiments, a heterologously encoded TCR of a modified CD4$^+$ T cell is capable of specifically binding to a peptide:antigen HLA complex on a cell surface independent of CD8 or in the absence of CD8.

In further embodiments, a modified CD4$^+$ T cell further comprises a heterologous polynucleotide encoding at least an extracellular portion of a CD8 co-receptor. As shown in the Examples, co-expression of a MAGE-A1-specific binding protein of the present disclosure and at least an extracellular portion of a CD8 co-receptor by a CD4$^+$ T cell can confer a new or improved functionality (e.g., improved cytokine release, CTL response when bound to a MAGE-A1:HLA-expressing target cell) upon the CD4$^-$ T cell. An amino acid sequence of a CD8 co-receptor α-chain is provided in SEQ ID NO:143. Amino acid sequences of five different isoforms of CD8 co-receptor β-chain are provided in SEQ ID NOS:144-148, respectively. In some embodiments, a modified CD4$^+$ T cell of this disclosure further comprises a heterologous polynucleotide encoding a full-length CD8 co-receptor receptor β-chain, a heterologous polynucleotide encoding a full-length CD8 co-receptor α-chain, or both.

Also provided herein are methods for making a modified CD4$^+$ T cell, wherein the methods comprise transducing a CD4+ T cell with a heterologous polynucleotide encoding a TCR from a CD8$^+$ T cell that is capable of specifically binding a peptide antigen. In certain embodiments, a TCR-encoding polynucleotide used to modify a CD4$^+$ T cell is from a naturally occurring CD8$^+$ T cell (i.e., the TCR is a naturally occurring TCR). Further embodiments of the methods may include transducing the CD4$^+$ T cell with a heterologous polynucleotide encoding at least an extracellular portion of a CD8 co-receptor, which may in some embodiments comprise a CD8α and a CD8β from the CD8$^+$ T cell.

Compositions

Also provided herein are compositions (e.g., pharmaceutical compositions) that comprise a modified cell as disclosed herein and a pharmaceutically acceptable carrier, diluent, or excipient. Suitable excipients include water, saline, dextrose, glycerol, or the like and combinations thereof. In embodiments, compositions comprising fusion proteins or host cells as disclosed herein further comprise a suitable infusion media. Suitable infusion media can be any isotonic medium formulation, typically normal saline, Normosol R (Abbott) or Plasma-Lyte A (Baxter), 5% dextrose in water, Ringer's lactate can be utilized. An infusion medium can be supplemented with human serum albumin or other human serum components. Compositions described herein may be presented in unit-dose or multi-dose containers, such as sealed ampoules or vials. Such containers may be frozen to preserve the stability of the formulation until infusion into the patient.

An "effective amount" of a composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

Compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's condition, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the compositions administered according to the methods described herein can be determined by performing pre-clinical (including in vitro and in vivo studies) and clinical studies and analyzing data obtained therefrom by appropriate statistical, biological, and clinical methods and techniques.

A therapeutically effective dose is an amount of host cells (expressing a binding protein or high affinity recombinant TCR specific for human MAGE-A1) used in adoptive transfer that is capable of producing a clinically desirable result (i.e., a sufficient amount to induce or enhance a specific T cell immune response against cells overexpressing MAGE-A1 (e.g., a cytotoxic T cell response) in a statistically significant manner) in a treated human or non-human mammal. The dosage for any one patient depends upon many factors, including the patient's size, weight, body surface area, age, the particular therapy to be administered, sex, time and route of administration, general health, and other drugs being administered concurrently. Doses will vary, but a preferred dose for administration of a host cell comprising a recombinant expression vector as described herein is about $10^7$ cells/m$^2$, about $5\times10^7$ cells/m$^2$, about $10^8$ cells/m$^2$, about $5\times10^8$ cells/m$^2$, about $10^9$ cells/m$^2$, about $5\times10^9$ cells/m$^2$, about $10^{10}$ cells/m$^2$, about $5\times10^{10}$ cells/m$^2$, or about $10^{11}$ cells/m$^2$. In certain embodiments, a unit dose comprises a modified cell as described herein at a dose of about $10^7$ cells/m$^2$ to about $10^{11}$ cells/m$^2$.

In certain embodiments, a unit dose comprises (i) a composition comprising at least about 30%, at least about 40%, at least about 50%, at least about 60%, at least about 70%, at least about 80%, at least about 85%, at least about 90%, or at least about 95% engineered CD4$^+$ T cells, combined with (ii) a composition comprising at least about 30%, at least about 40%, at least about 50%, at least about 60%, at least about 70%, at least about 80%, at least about 85%, at least about 90%, or at least about 95% engineered CD8$^+$ T cells, in about a 1:1 ratio. In further embodiments, a unit dose contains a reduced amount or substantially no naïve T cells (i.e., has less than about 50%, less than about 40%, less than about 30%, less than about 20%, less than about 10%, less than about 5%, or less than about 1% the population of naïve T cells present in a unit dose as compared to a patient sample having a comparable number of PBMCs).

In some embodiments, a unit dose comprises (i) a composition comprising at least about 50% engineered CD4$^+$ T cells, combined with (ii) a composition comprising at least about 50% engineered CD8$^+$ T cells, in about a 1:1 ratio, wherein the unit dose contains a reduced amount or substantially no naïve T cells. In further embodiments, a unit dose comprises (i) a composition comprising at least about 60% modified CD4$^+$ T cells, combined with (ii) a composition comprising at least about 60% modified CD8$^+$ T cells, in about a 1:1 ratio, wherein the unit dose contains a reduced amount or substantially no naïve T cells. In still further embodiments, a unit dose comprises (i) a composition comprising at least about 70% modified CD4$^+$ T cells, combined with (ii) a composition comprising at least about 70% modified CD8$^+$ T cells, in about a 1:1 ratio, wherein the unit dose contains a reduced amount or substantially no naïve T cells. In some embodiments, a unit dose comprises (i) a composition comprising at least about 80% modified CD4$^+$ T cells, combined with (ii) a composition comprising at least about 80% modified CD8$^+$ T cells, in about a 1:1 ratio, wherein the unit dose contains a reduced amount or substantially no naïve T cells. In some embodiments, a unit dose comprises (i) a composition comprising at least about 85% modified CD4$^+$ T cells, combined with (ii) a composition comprising at least about 85% modified CD8$^+$ T cells, in about a 1:1 ratio, wherein the unit dose contains a reduced amount or substantially no naïve T cells. In some embodiments, a unit dose comprises (i) a composition comprising at least about 90% modified CD4$^+$ T cells, combined with (ii) a composition comprising at least about 90% modified CD8$^+$ T cells, in about a 1:1 ratio, wherein the unit dose contains a reduced amount or substantially no naïve T cells.

In any of the embodiments described herein, a unit dose comprises equal, or approximately equal numbers, of modified CD45RA$^-$ CD3$^+$ CD8$^+$ and modified CD45RA$^-$ CD3$^+$ CD4$^+$ T$_M$ cells.

The development of suitable dosing and treatment regimens for using the particular compositions described herein in a variety of treatment regimens, including, e.g., parenteral or intravenous administration or formulation. If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of modified cells or active compound calculated to produce the desired effect in association with an appropriate pharmaceutical carrier.

As used herein, administration of a composition refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., modified cells with one or more cytokines; immunosuppressive therapy such as calcineurin inhibitors, corticosteroids, microtubule inhibitors, low dose of a mycophenolic acid prodrug, HDAC inhibitors, DNA hypomethylation agents, or any combination thereof).

In certain embodiments, a plurality of doses of a modified cell described herein is administered to the subject, which may be administered at intervals between administrations of about two to about four weeks.

Methods of Treatment

In certain aspects, the instant disclosure is directed to methods for treating a hyperproliferative disorder or a condition characterized by MAGE-A1 expression (e.g., aberrant MAGE-A1 expression) by administering to human subject in need thereof a modified cell, composition, or unit dose as disclosed herein (or any combination thereof).

A condition associated with MAGE-A1 expression includes any disorder or condition in which underactivity, over-activity or improper activity of a MAGE-A1 cellular or molecular event is present, and may be the result of unusually high (with statistical significance) levels of MAGE-A1 expression or inappropriate (i.e., not occurring in healthy cells of the given cell type) expression in afflicted cells (e.g., myeloma cells), relative to normal cells. A subject having such a disorder or condition would benefit from treatment with a composition or method of the presently described embodiments. Some conditions associated with aberrant MAGE-A1 expression thus may include acute as well as chronic disorders and diseases, such as those pathological conditions that predispose the subject to a particular disorder.

Some examples of conditions associated with MAGE-A1 expression include proliferative disorders or hyperproliferative disorders, which refer to states of activated and/or proliferating cells (which may also be transcriptionally overactive) in a subject including tumors, neoplasms, cancer, malignancy, etc. In addition to activated or proliferating cells, the hyperproliferative disorder may also include an aberration or dysregulation of cell death processes, whether by necrosis or apoptosis. Such aberration of cell death processes may be associated with a variety of conditions, including cancer (including primary, secondary malignancies as well as metastasis), or other conditions.

The presence of a hyperproliferative disorder or malignant condition in a subject refers to the presence of dysplastic, cancerous and/or transformed cells in the subject, including, for example neoplastic, tumor, non-contact inhibited or oncogenically transformed cells, or the like (e.g., solid cancers; hematologic cancers including lymphomas and leukemias, such as acute myeloid leukemia, chronic myeloid leukemia, etc.), which are known in the art and for which criteria for diagnosis and classification are established (e.g., Hanahan and Weinberg, *Cell* 144:646, 2011; Hanahan and Weinberg, *Cell* 100:57, 2000; Cavallo et al., *Canc. Immunol. Immunother.* 60:319, 2011; Kyrigideis et al., *J. Carcinog.* 9:3, 2010). In certain embodiments, such cancer cells may be cells of acute myeloid leukemia, B-cell lymphoblastic leukemia, T-cell lymphoblastic leukemia, or myeloma, including cancer stem cells that are capable of initiating and serially transplanting any of these types of cancer (see, e.g., Park et al., *Molec. Therap.* 17:219, 2009).

In certain embodiments, there are provided methods for treating a hyperproliferative disorder, such as a hematological malignancy or a solid cancer, wherein the method comprises administering to a human subject in need thereof a modified cell, composition, or unit dose of the present disclosure. Exemplary hematological malignancies include acute lymphoblastic leukemia (ALL), acute myeloid leukemia (AML), chronic myelogenous leukemia (CIVIL), chronic eosinophilic leukemia (CEL), myelodysplastic syndrome (MDS), non-Hodgkin's lymphoma (NHL), or multiple myeloma (MM).

In further embodiments, there are provided methods for treating a hyperproliferative disorder, such as a solid cancer is selected from non-small cell lung cancer (NSCLC), triple negative breast cancer (TNBC), ovarian cancer, malignant melanoma, colon cancer, colorectal adenocarcinoma, colorectal cancer, biliary cancer, bladder cancer, bone and soft tissue carcinoma, brain tumor, breast cancer, cervical cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, osteosarcoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of a binding protein or high affinity recombinant TCR specific for human MAGE-A1 or a host cell expressing the same, and optionally an adjunctive therapy (e.g., a cytokine such as IL-2, IL-15, IL-21 or any combination thereof), in an amount sufficient to provide therapeutic or prophylactic benefit. Therapeutic or prophylactic benefit resulting from therapeutic treatment or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

"Treatment" can also mean prolonging survival when compared to expected survival if a subject were not receiving treatment. Subjects in need of the methods and compositions described herein include those who already have the disease or disorder, as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit, as described in the examples.

In certain embodiments of the presently disclosed methods, a modified cell is capable of promoting an antigen-specific T cell response against a MAGE-A1 in a class I HLA-restricted manner. In some embodiments, a class I HLA-restricted response is transporter-associated with antigen processing (TAP) independent. In some embodiments, an antigen-specific T cell response promoted by a modified cell administered according of the presently disclosed methods comprises at least one of a CD4+ helper T lymphocyte (Th) response and a CD8+ cytotoxic T lymphocyte (CTL) response. In particular embodiments, a CTL response elicited according to the instantly disclosed methods is directed against a cell having aberrant MAGE-A1 expression (e.g., a MAGE-A1+ tumor cell). The level of a CTL immune response may be determined by any one of numerous immunological methods described herein and routinely practiced in the art. The level of a CTL immune response may be determined prior to and following administration of any one of the herein described MAGE-A1-specific binding proteins expressed by, for example, a T cell. Cytotoxicity assays for determining CTL activity may be performed using any one of several techniques and methods routinely practiced in the art (see, e.g., Henkart et al., "Cytotoxic T-Lymphocytes" in *Fundamental Immunology*, Paul (ed.) (2003 Lippincott Williams & Wilkins, Philadelphia, Pa.), pages 1127-50, and references cited therein).

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to a MAGE-A1-derived antigen peptide as described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

Modified cells of this disclosure are useful, in certain embodiments, in adoptive cell therapies. For example, in some embodiments, a modified cell is modified (e.g., transduced with a recombinant expression vector or polynucleotide of the present disclosure) ex vivo, and then administered to a subject in need thereof. In certain embodiments, modified cell is an allogeneic cell, a syngeneic cell, or an autologous cell (i.e., relative to the subject administered the modified cell). In any of the presently disclosed methods, a modified cell comprises a modified human immune cell selected from a CD4+ T cell, a CD8+ T cell, a CD4– CD8– double negative T cell, a γδ T cell, a natural killer cell, a dendritic cell, or any combination thereof. In certain embodiments, a modified cell is a T cell, e.g., is a naïve T cell, a central memory T cell, an effector memory T cell, or any combination thereof.

In particular embodiments, a modified cell used in the presently disclosed methods is a CD4+ T cell. In some such embodiments, a modified CD4+ T cell further comprises a heterologous polynucleotide encoding at least an extracellular portion of a CD8 co-receptor, and optionally encodes a complete CD8 α-chain, a complete CD8 β-chain, or both. Such methods may, in certain embodiments, further comprise administering to the subject a CD8+ T cell that is capable of specifically binding to a MAGE-A1 peptide:HLA complex on a cell surface, such as a CD8+ modified T cell according to the present disclosure.

Presently disclosed treatment or prevention methods may include any appropriate method of administering or dosing a modified cell, or a combination therapy. For example, in certain embodiments, a plurality of doses of a modified cell as described herein is administered to the subject, which may be administered at intervals between administrations of about two to about four weeks. In addition, treatment or prevention methods of this disclosure may be administered to a subject as part of a treatment course or regimen, which may comprise additional treatments prior to, or after, administration of the instantly disclosed unit doses, cells, or compositions. In further embodiments, a cytokine is administered sequentially, provided that the subject was administered the recombinant host cell at least three or four times before cytokine administration. In certain embodiments, the cytokine is administered subcutaneously (e.g., IL-2, IL-15, IL-21). In still further embodiments, the subject being treated is further receiving immunosuppressive therapy, such as calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant. In some embodiments, subject has been administered one or more of a DNA hypomethylation agent and a HDAC inhibitor, either or both of which may enhance MAGE-A1 expression (see Weon, J. L. and P. R. Potts, *Curr Opin Cell Biol*, 2015. 37: p. 1-8) and thereby enhance an adoptive cell therapy targeting MAGE-A1.

Methods according to the instant disclosure may, in certain embodiments, further include administering one or more additional agents to treat the disease or disorder in a combination therapy. For example, in certain embodiments, a combination therapy comprises administering a modified cell with (concurrently, simultaneously, or sequentially) an immune checkpoint inhibitor. In some embodiments, a combination therapy comprises administering a modified cell with an agonist of a stimulatory immune checkpoint agent. In further embodiments, a combination therapy comprises administering a modified cell with a secondary therapy, such as chemotherapeutic agent, a radiation therapy, a surgery, an antibody, or any combination thereof.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/ 2B4, HVEM, BTLA, CD160, TIM3, GALS, KIR, PVR1G (CD112R), PVRL2, adenosine, A2aR, immunosuppressive cytokines (e.g., IL-10, IL-4, IL-1RA, IL-35), IDO, arginase, VISTA, TIGIT, LAIR1, CEACAM-1, CEACAM-3, CEACAM-5, Treg cells, or any combination thereof.

An immune suppression agent inhibitor (also referred to as an immune checkpoint inhibitor) may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise a modified cell with one or more inhibitor of any one of the following immune suppression components, singly or in any combination.

In certain embodiments, a modified cell cell is used in combination with a PD-1 inhibitor, for example a PD-1-specific antibody or binding fragment thereof, such as pidilizumab, nivolumab, pembrolizumab, MEDI0680 (formerly AMP-514), AMP-224, BMS-936558 or any combination thereof. In further embodiments, a modified cell of the present disclosure is used in combination with a PD-L1 specific antibody or binding fragment thereof, such as BMS-936559, durvalumab (MEDI4736), atezolizumab (RG7446), avelumab (MSB0010718C), MPDL3280A, or any combination thereof.

In certain embodiments, a modified cell of the present disclosure is used in combination with a LAG3 inhibitor, such as LAG525, IMP321, IMP701, 9H12, BMS-986016, or any combination thereof.

In certain embodiments, a modified cell is used in combination with an inhibitor of CTLA4. In particular embodiments, a modified cell is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, a modified cell is used in combination with a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., *Cancer Res.* 73:4820, 2013, as well as those described in U.S. Pat. No. 9,574,000 and PCT Patent Publication Nos. WO/201640724A1 and WO 2013/025779A1.

In certain embodiments, a modified cell is used in combination with an inhibitor of CD244.

In certain embodiments, a modified cell is used in combination with an inhibitor of BLTA, HVEM, CD160, or any combination thereof. Anti CD-160 antibodies are described in, for example, PCT Publication No. WO 2010/084158.

In certain embodiments, a modified cell is used in combination with an inhibitor of TIM3.

In certain embodiments, a modified cell is used in combination with an inhibitor of Gal9.

In certain embodiments, a modified cell is used in combination with an inhibitor of adenosine signaling, such as a decoy adenosine receptor.

In certain embodiments, a modified cell is used in combination with an inhibitor of A2aR.

In certain embodiments, a modified cell is used in combination with an inhibitor of KIR, such as lirilumab (BMS-986015).

In certain embodiments, a modified cell is used in combination with an inhibitor of an inhibitory cytokine (typically, a cytokine other than TGFβ) or Treg development or activity.

In certain embodiments a modified cell is used in combination with an IDO inhibitor, such as levo-1-methyl tryptophan, epacadostat (INCB024360; Liu et al., *Blood* 115: 3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tirapazamine, or any combination thereof.

In certain embodiments, a modified cell is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, a modified cell is used in combination with an inhibitor of VISTA, such as CA-170 (Curis, Lexington, Mass.).

In certain embodiments, a modified cell is used in combination with an inhibitor of TIGIT such as, for example, COM902 (Compugen, Toronto, Ontario Canada), an inhibitor of CD155, such as, for example, COM701 (Compugen), or both.

In certain embodiments, a modified cell is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, a modified cell is used in combination with a LAIR1 inhibitor.

In certain embodiments, a modified cell is used in combination with an inhibitor of CEACAM-1, CEACAM-3, CEACAM-5, or any combination thereof.

In certain embodiments, a modified cell is used in combination with an agent that increases the activity (i.e., is an agonist) of a stimulatory immune checkpoint molecule. For example, a modified cell can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering a modified cell with one or more agonist of a stimulatory immune checkpoint molecule, including any of the foregoing, singly or in any combination.

In certain embodiments, a combination therapy comprises a modified cell and a secondary therapy comprising one or more of: an antibody or antigen binding-fragment thereof that is specific for a cancer antigen expressed by the non-inflamed solid tumor, a radiation treatment, a surgery, a chemotherapeutic agent, a cytokine, RNAi, or any combination thereof.

In certain embodiments, a combination therapy method comprises administering a modified cell and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer in a subject are well-known to those of ordinary skill in the art.

In certain embodiments, a combination therapy method comprises administering an a modified cell and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/ antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (Vβ 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethyleniminies and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

Cytokines are increasingly used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with a modified cell of this disclosure.

EXAMPLES

Example 1

Generation of High-Affinity TCRs Specific for Cancer Epitopes

Figure 2A:
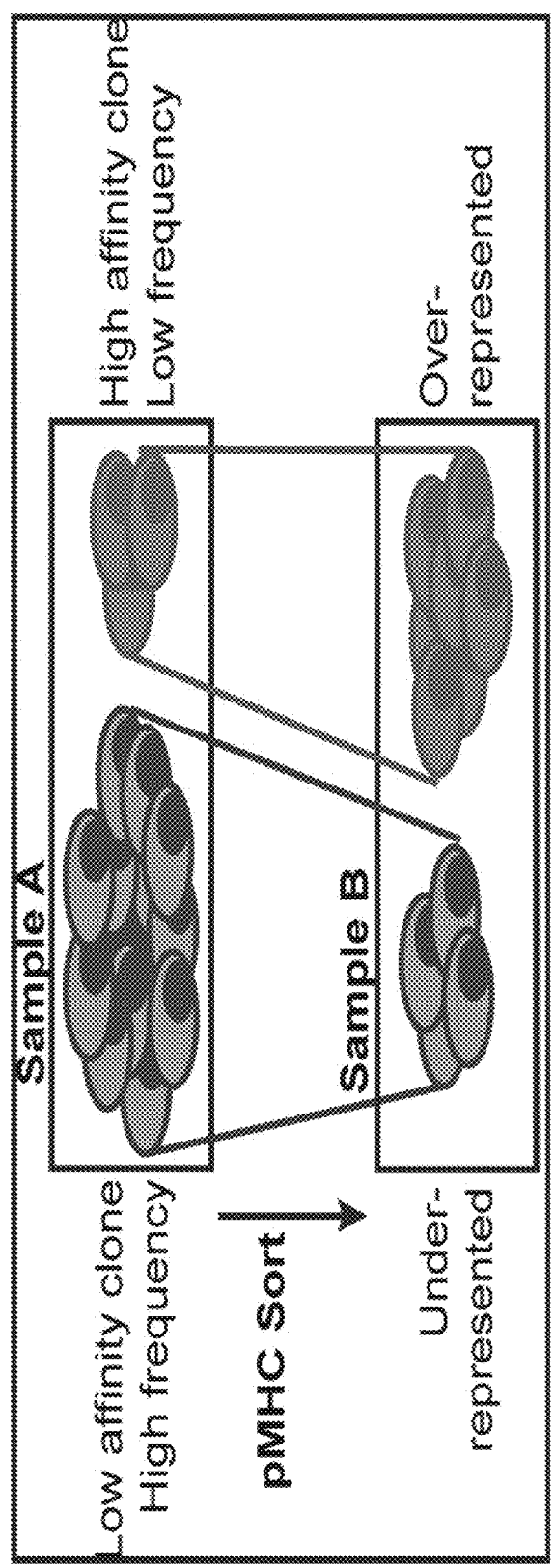
FIGS. 2A and 2B show, respectively, (A) a schematic of a T cell enrichment assay performed by the inventors of the present disclosure, (B) flow cytometry data from a series of sorting experiments used to enrich for antigen-specific CD8$^+$ T cells.
Figure 2B:
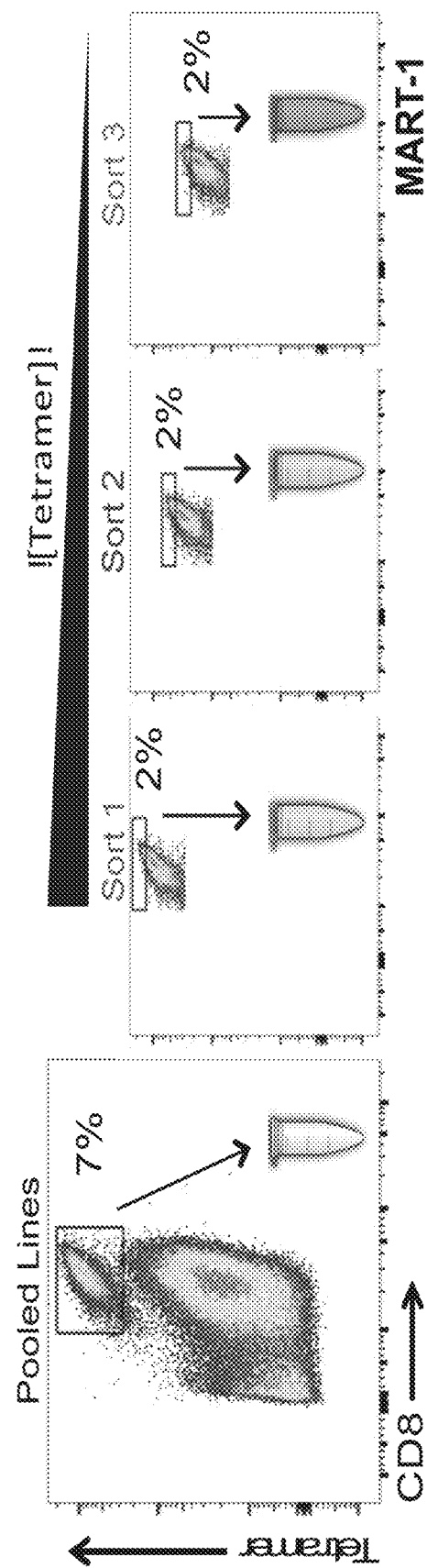

Generation of high-affinity TCRs for use in adoptive cell therapies is difficult due to thymic selection, wherein TCRs with high-affinity for self-antigens (e.g., MART1 and MAGE-A1) are removed and, therefore, relatively rare as compared to TCRs specific for foreign antigens (see, e.g., FIGS. 1A and 1B). As shown in FIGS. 2A and 2B, a new screening and enrichment process was developed to identify high-affinity TCRs specific for MAGE-A1. Briefly, CD8+ T cells from peripheral blood mononuclear cells (PBMCs) of 12 healthy donors were stimulated once with peptide-pulsed autologous DCs and twice with peptide-pulsed autologous PBMCs, in the presence of IL-2, IL-7, IL-15 and IL-21, to obtain polyclonal MAGE-A1-specific CD8+ T cell lines. The stimulated cell lines from all donors were pooled and sorted several times using limited concentrations MAGE-A1 peptide:MHC multimers, which produced enriched populations of high-affinity T cell clones. TCRβ genes from the populations were sequenced to the frequency of TCRs in pooled and individual pMHC sorts.

Figure 3:
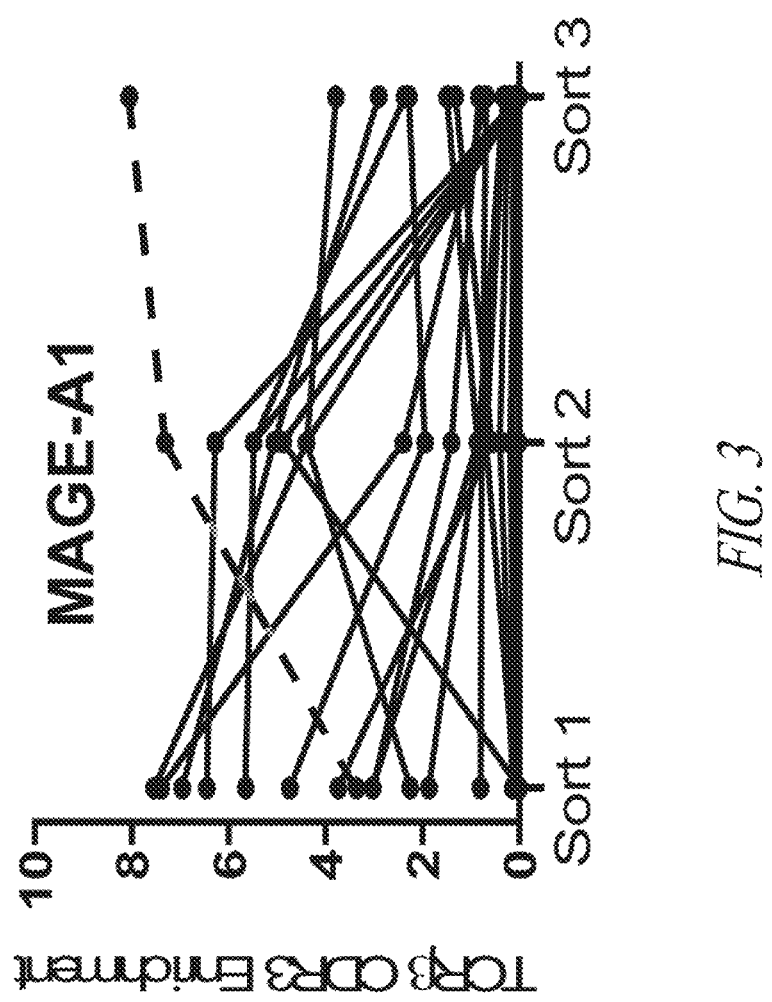
FIG. 3 shows exemplary data from a TCRβ CDR3 enrichment scheme of the present disclosure using MAGE-A1:HLA tetramers.

FIG. 3 shows exemplary data from a series of pMHC sorts that enriched for T cells expressing TCRβ CDR3 specific for the MAGE-A1 antigen. High-affinity clones identified from the pool strongly bound MAGE-A1:MHC, correlating with lower $EC_{50}$ (FIGS. 4A, 4B).

Example 2

In Vitro Functionality of a MAGE-A1-Specific TCR

Figure 5A:
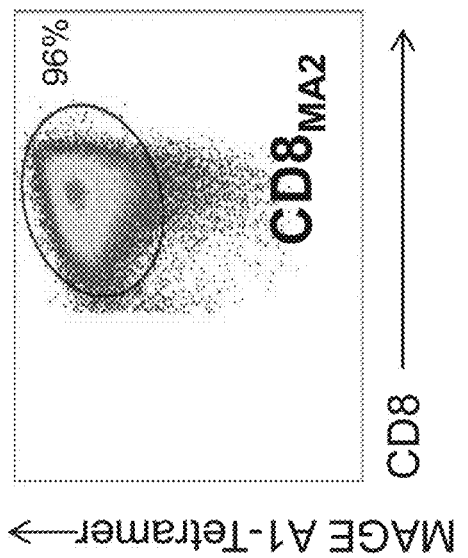
FIGS. 5A-5C provide, respectively, (A) flow cytometry data showing MAGE-A1-specific CD8$^+$ T cells of the present disclosure binding MAGE-A1:HLA tetramers, (B) cytokine production by MAGE-A1-specific CD8$^+$ T cells in the absence (left) or presence (right) of antigen-expressing U266 myeloma cells, and (C) specific lysis data showing that high-affinity MAGE-A1 TCR-transduced CD8$^+$ T cells of this disclosure bind antigen:MHC tetramers and kill cells presenting MAGE-A1:MHC (A*0201). Data in (C) was from a standard Cr$^{51}$-release assay in which the CD8$^+$ T cells were co-cultured with U266 cells alone, with exogenous interferon-gamma (IFNγ) or with exogenous MAGE-A1 peptide.
Figure 5B:
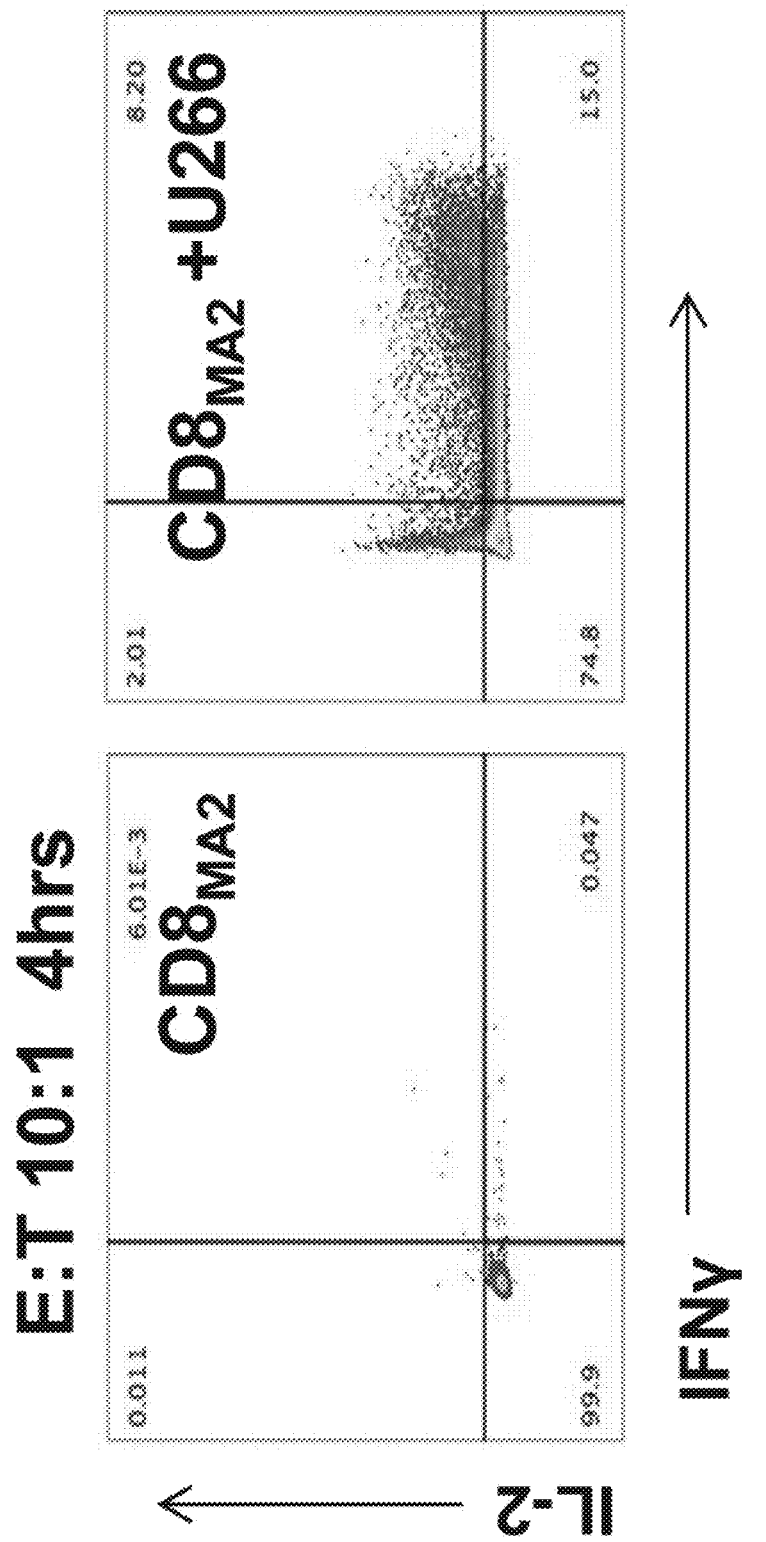
Figure 5C:
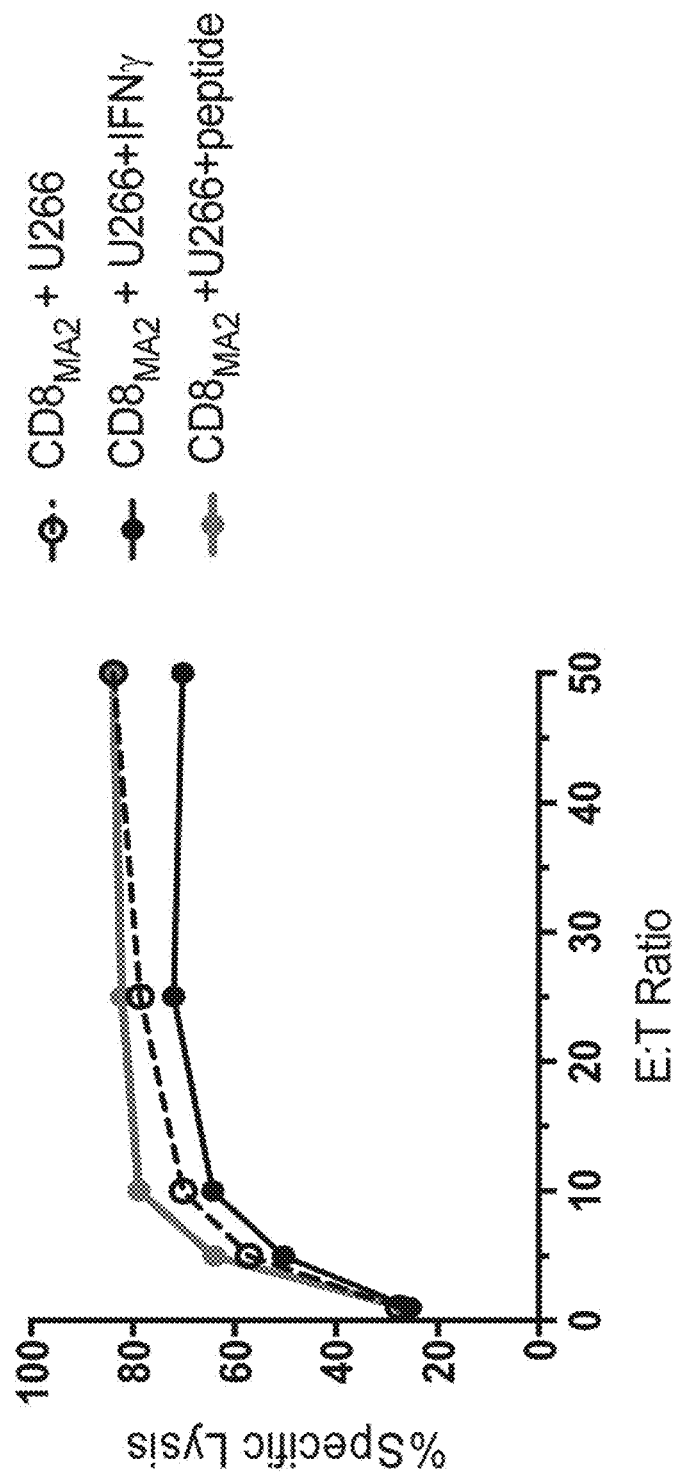

A high-affinity MAGE-A1-specific $CD8^+$T cell clone "MA2" generated using the method of Example 1 (FIG. 5A) was selected for further testing. As shown in FIG. 5B, $MA2^+CD8^+$T cells selectively produced cytokines when co-cultured with MAGE-A1-expressing HLA-A*$0201^+$ U266 multiple myeloma cells (effector to target (E:T) ratio of 10:1, 4 hrs). In a standard 4 hr. $Cr^{51}$-release assay, $MA2^+$ T cells were capable of killing target cells in the presence or absence of exogenous IFN-γ and MAGE-A1 peptide (FIG. 5C).

Example 3

MAGE-A1-Specific CD8 TCR Binds Tetramer Independent of CD8

$CD8^+$ TCRs recognize antigens presented by class I HLA molecules, while $CD4^+$ TCRs recognize antigens presented in the context of class II HLA. To test whether the high-affinity MA2 TCR could bind MAGE-A1:HLA I independent of CD8, $CD4^+$ T cells were transduced with MA2 TCR (see, e.g., schematic diagrams of FIGS. 6A and 6B). As shown in FIGS. 7A and 7B, $CD4^+$ T cells transduced with MA2 TCR bound MAGE-A1:HLA tetramers with an affinity that was comparable (~5-fold difference in $B_{max}$) to MA2

CD8+ T cells. However, as shown in FIG. 7C, the transformed CD4+ T cells did not kill target cells in vitro.

Example 4

Figure 6A:
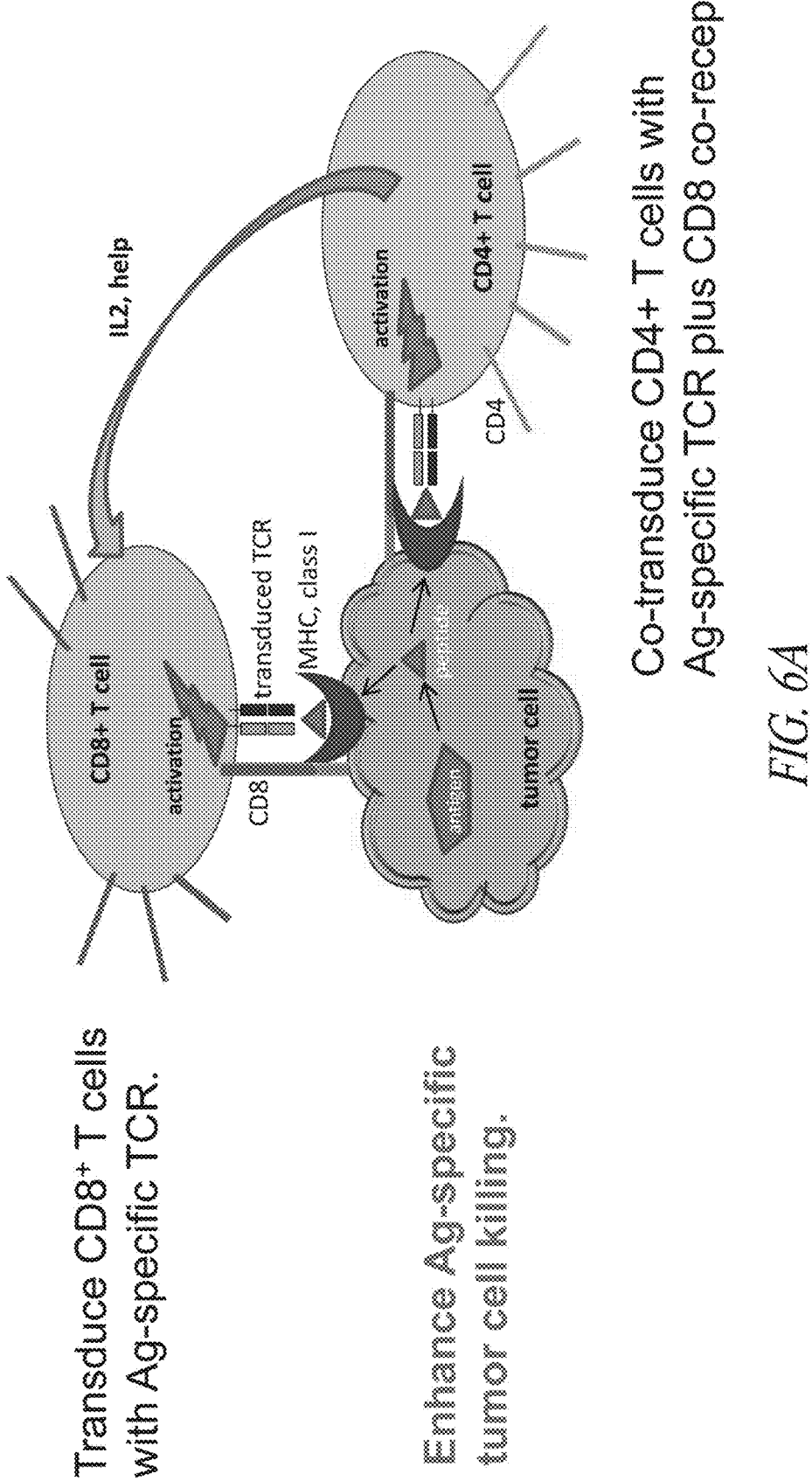
FIG. 6A illustrates an immunotherapy approach according to the present disclosure in which CD4$^+$ T cells are transduced to express a TCR and a CD8 co-receptor, both from a CD8$^+$ T cell that is specific for a peptide antigen. Activation of the transduced CD4$^+$ T cell can augment or improve the antigenic response of CD8$^+$ T cells, such as infused CTLs in an immunotherapy setting.
Figure 6B:
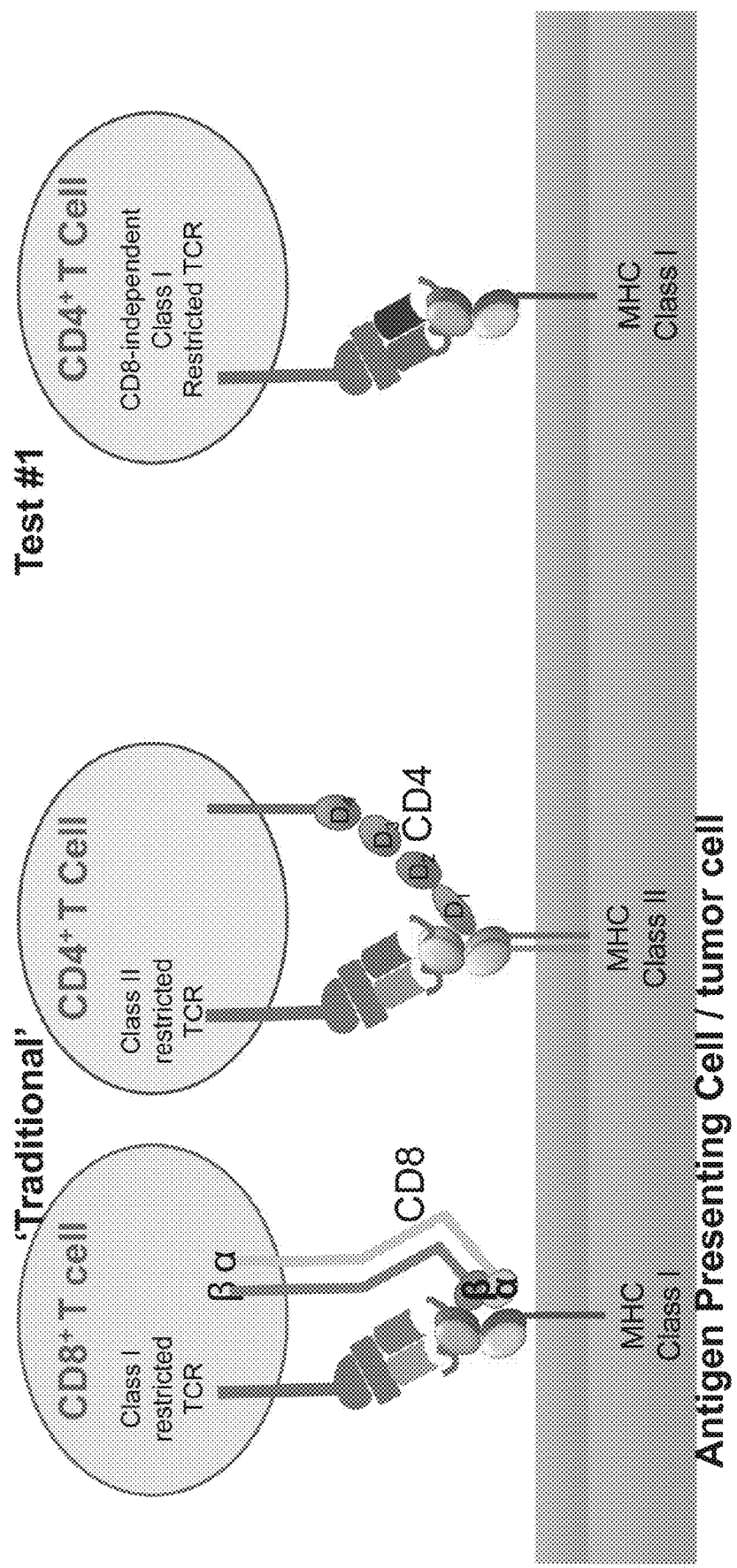
FIG. 6B shows the design of an experiment performed by the inventors of the present disclosure in which a CD4$^+$ T cell was transduced to express a CD8-independent MHC Class I-restricted TCR, but not a CD8 co-receptor.
Figure 7B:
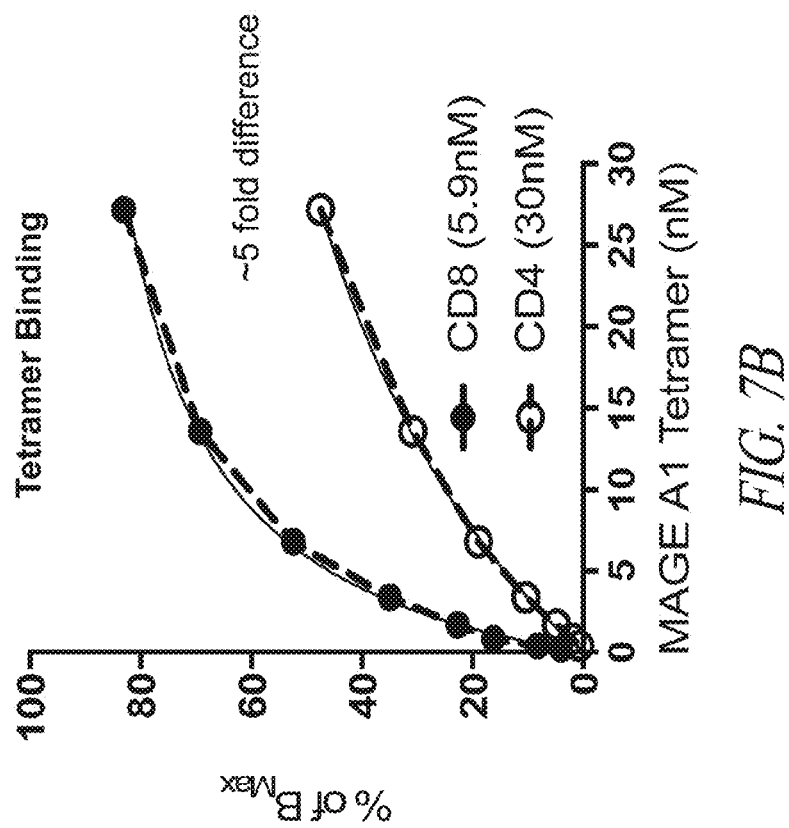
FIG. 7B shows specific binding by the MAGE-A1-specific T cells to MAGE-A1:MHC tetramers.
Figure 7A:
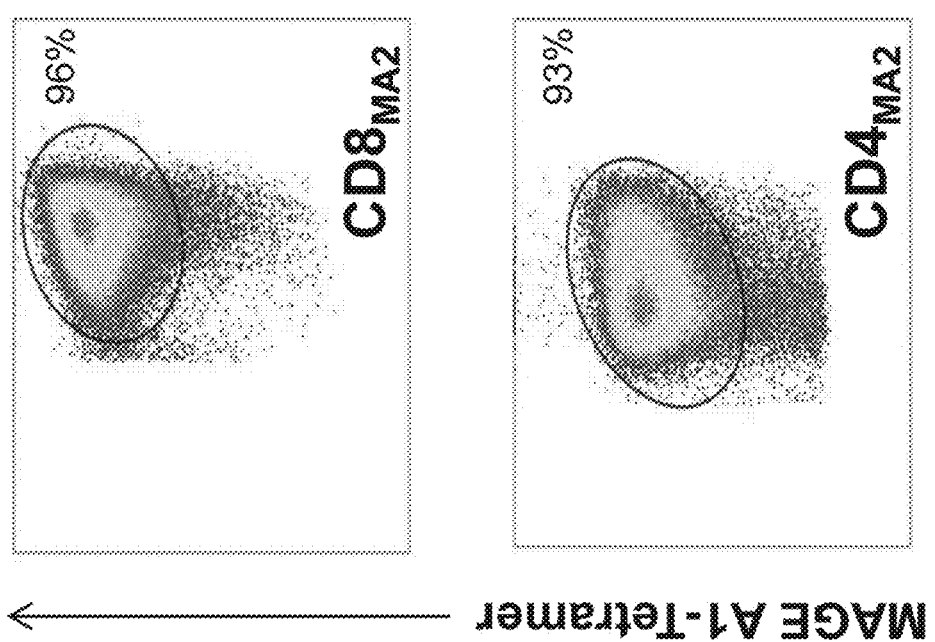
FIG. 7A shows flow cytometry data from an experiment in which T cells (CD8$^+$ and CD4$^+$) expressing high-affinity CD8 anti-MAGE-A1 TCR were assayed for binding to MAGE-A1:MHC tetramers.
Figure 8A:
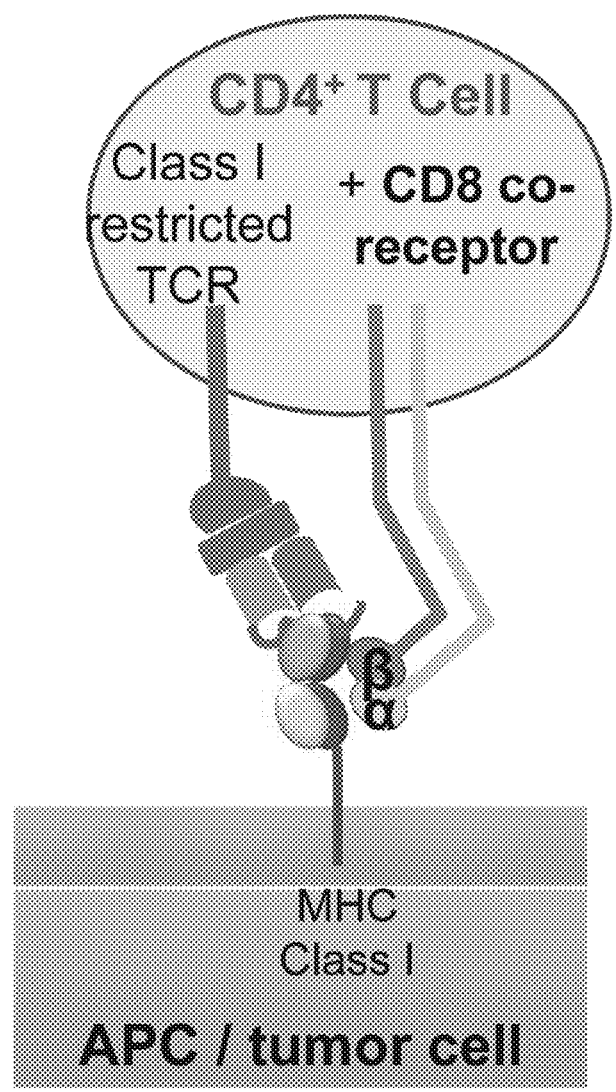
FIG. 8A shows a schematic illustrating an experiment conducted by the inventors of the present disclosure in which CD4$^+$ T cells were transduced to express the high-affinity MAGE A1 Class I TCR plus a CD8αβ co-receptor and examined for functionality in the presence of cells expressing peptide:MHC.
Figure 8B:
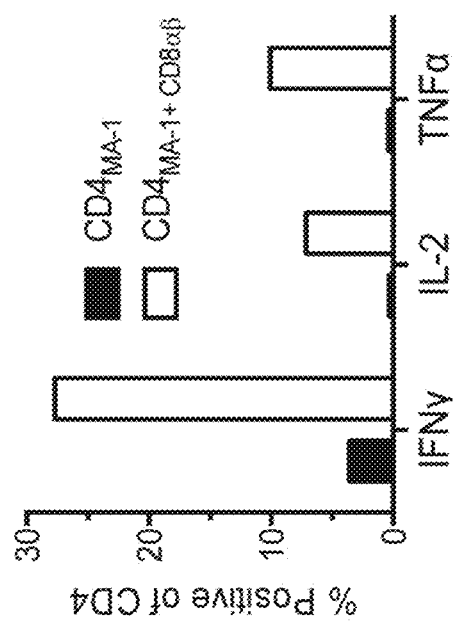
FIG. 8B shows that a higher proportion of the CD4$^+$ T cells transduced with both MAGE-A1 TCR and CD8 co-receptor produced cytokines as compared to CD4$^+$ T cells expressing the MAGE-A1 TCR alone.
Figure 8C:
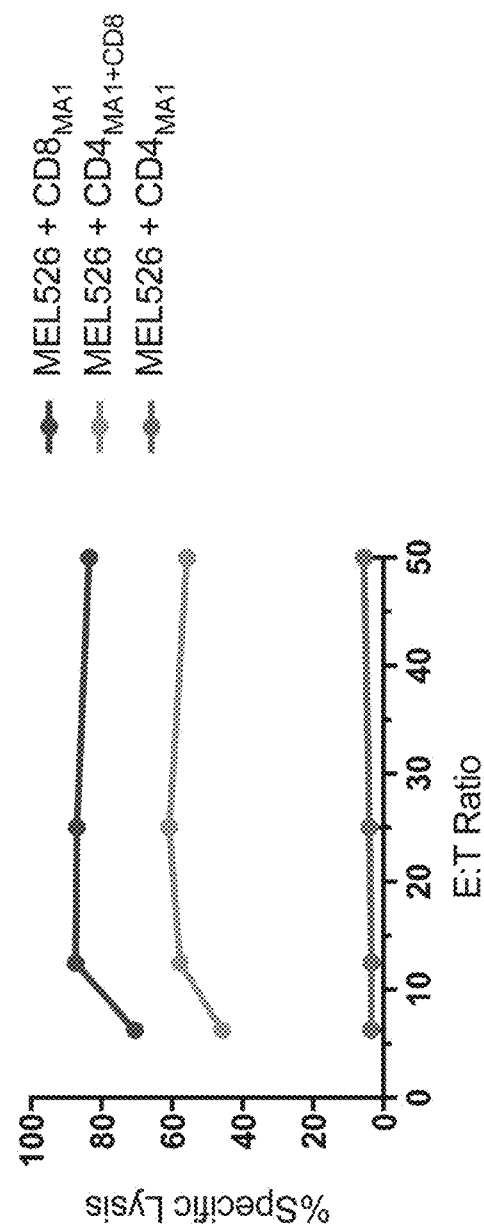
FIG. 8C shows specific lysis of antigen-presenting MEL526 melanoma target cells by the indicated T cells.
Figure 8D:
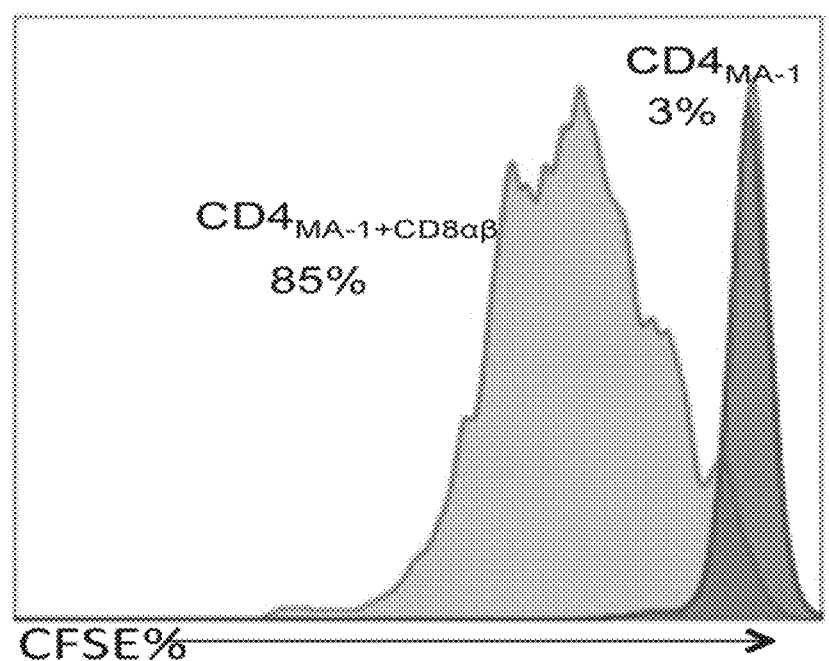
FIG. 8D shows expansion of the two groups of transduced CD4$^+$ T cells following stimulation with antigen.

Functional Testing of an Engineered CD4+ T Cell Expressing a MAGE-A1-Specific CD8 TCR and CD8 Co-Receptor Next, the ability of a CD8+co-receptor to improve functionality of high-affinity CD8-TCR-expressing CD4+ T cells was investigated (see, e.g., FIG. 6A). As illustrated in the diagram of FIG. 8A, CD4+ T cells were transduced with both a high-affinity Class-I-restricted MAGE-A1-specific TCR and a CD8 co-receptor. FIG. 8B shows that a greater proportion of CD4+ T cells transduced with both exogenous CD8 TCR and CD8 co-receptor produced cytokines in response to antigen, as compared to CD4+ T cells transduced with the exogenous CD8 TCR alone. FIG. 8C shows that the dually transduced CD4+T cells surprisingly exhibited cytolytic activity against MEL526 target cells, at rates comparable to CD8+ T cells expressing the same high-affinity TCR. As shown in FIG. 8D, the dually transduced CD4+ T cells also proliferated more robustly following stimulation with antigen than MA1+CD4+ cells without CD8.

These data show that high-affinity MAGE-A1-specific TCRs of the present disclosure, and CD8+ and CD4+ T cells expressing the same, are useful for targeting and killing MAGE-A1-expressing cancer cells and have use in cellular immunotherapies against MAGE-A1-expressing diseases.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, if any, including U.S. Provisional Patent Application No. 62/471,956, filed Mar. 15, 2017, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated modified cell comprising a heterologous polynucleotide encoding a binding protein, wherein the encoded binding protein comprises:

(a) a T cell receptor (TCR) α-chain variable (Vα) domain having CDR1, CDR2, and CDR3 amino acid sequences of SEQ ID NOS.:48-50, respectively, and a TCR β-chain variable (Vβ) domain having CDR1, CDR2, and CDR3 amino acid sequences of SEQ ID NOS.:45-47, respectively;

(b) a TCR Vα domain having CDR1, CDR2, and CDR3 amino acid sequences of SEQ ID NOS.:30-32, respectively, and a TCR Vβ domain having CDR1, CDR2, and CDR3 amino acid sequences of SEQ ID NOS.:27-29, respectively;

(c) a TCR Vα domain having CDR1, CDR2, and CDR3 amino acid sequences of SEQ ID NOS.:36-38, respectively, and a TCR Vβ domain having CDR1, CDR2, and CDR3 amino acid sequences of SEQ ID NOS.:33-35, respectively;

(d) a TCR Vα domain having CDR1, CDR2, and CDR3 amino acid sequences of SEQ ID NOS.:42-44, respectively, and a TCR Vβ domain having CDR1, CDR2, and CDR3 amino acid sequences of SEQ ID NOS.:39-41, respectively; or (e) a TCR Vα domain having CDR1, CDR2, and CDR3 amino acid sequences of SEQ ID NOS.:24-26, respectively, and a TCR Vβ domain having CDR1, CDR2, and CDR3 amino acid sequences of SEQ ID NOS.:21-23, respectively; and wherein the binding protein is capable of specifically binding to a KVLEYVIKV (SEQ ID NO.: 123):human leukocyte antigen (HLA)-A *0201 complex on a cell surface independent of CD8 or in the absence of CD8.

2. The isolated modified cell of claim 1, wherein the encoded binding protein of (a) is capable of specifically binding to a KVLEYVIKV (SEQ ID NO:123):HLA-A*201 complex with a Kd less than or equal to about $10^{-8}$ M.

3. The isolated modified cell of claim 1, wherein the Vβ domain of the encoded binding protein is derived from a TRBV30 allele, a TRBV29 allele, or a TRBV9 allele.

4. The isolated modified cell of claim 1, wherein the Vα domain of the encoded binding protein is derived from a TRAV38-1 allele, a TRAV34 allele, a TRAV16 allele, or a TRAV5 allele.

5. An isolated modified cell comprising a heterologous polynucleotide encoding a binding protein, wherein the encoded binding protein comprises:

(a) a TCR Vα domain having CDR1, CDR2, and CDR3 amino acid sequences of SEQ ID NOS.:48-50, respectively, and a TCR Vβ domain having CDR1, CDR2, and CDR3 amino acid sequences of SEQ ID NOS.:45-47, respectively;

(b) a TCR Vα domain having CDR1, CDR2, and CDR3 amino acid sequences of SEQ ID NOS.:30-32, respectively, and a TCR Vβ domain having CDR1, CDR2, and CDR3 amino acid sequences of SEQ ID NOS.:27-29, respectively;

(c) a TCR Vα domain having CDR1, CDR2, and CDR3 amino acid sequences of SEQ ID NOS.:36-38, respectively, and a TCR Vβ domain having CDR1, CDR2, and CDR3 amino acid sequences of SEQ ID NOS.:33-35, respectively;

(d) a TCR Vα domain having CDR1, CDR2, and CDR3 amino acid sequences of SEQ ID NOS.:42-44, respectively, and a TCR Vβ domain having CDR1, CDR2, and CDR3 amino acid sequences of SEQ ID NOS.:39-41, respectively; or (e) a TCR Vα domain having CDR1, CDR2, and CDR3 amino acid sequences of SEQ ID NOS.:24-26, respectively, and a TCR Vβ domain having CDR1, CDR2, and CDR3 amino acid sequences of SEQ ID NOS.:21-23, respectively;

wherein the binding protein is capable of specifically binding to a KVLEYVIKV (SEQ ID NO.: 123):human leukocyte antigen (HLA)-A *0201 complex on a cell surface independent of CD8 or in the absence of CD8; and wherein:

(i) the encoded Vα domain comprises an amino acid sequence that is at least 90% identical to the amino acid sequence of any one of SEQ ID NOS.:3, 7, 11, 15, and 19; and (ii) the encoded Vβ domain comprises an amino acid sequence that is at least 90% identical to the amino acid sequence of any one of SEQ ID NOS.: 1, 5, 9, 13, and 17.

6. The isolated modified cell of claim 1, wherein the encoded binding protein comprises:

$V_\alpha$ CDR1, CDR2, and CDR3 amino acid sequences of SEQ ID NOS.:48-50, respectively, and $V_\beta$ CDR1, CDR2, and CDR3 amino acid sequences of SEQ ID NOS.:45-47, respectively.

7. The isolated modified cell of claim 1, wherein the encoded binding protein is a pre-binding protein and wherein the encoded Vα domain comprises or consists of the amino acid sequence according to SEQ ID NO.:3, 7, 11, 15, or 19.

8. The isolated modified cell of claim 1, wherein the encoded binding protein is a pre-binding protein and wherein the encoded Vβ domain comprises or consists of the amino acid sequence according to SEQ ID NO.:1, 5, 9, 13, or 17.

9. The isolated modified cell of claim 1, further comprising a heterologous polynucleotide encoding a TCR α-chain constant (Cα) domain having at least 90% sequence identity to the amino acid sequence of SEQ ID NO.:4, 8, 12, 16, or 20; and/or a heterologous polynucleotide encoding a TCR β-chain constant ($C_\beta$) domain comprising an amino acid sequence with at least 90% sequence identity to the amino acid sequence of SEQ ID NO.:2, 6, 10, 14, or 18.

10. The isolated modified cell according to claim 1, wherein the encoded binding protein is a pre-binding protein and the modified cell comprises:

(i) a polynucleotide encoding (1) a TCR α-chain pre-protein comprising (1)(a) a $V_\alpha$ domain comprising or consisting of SEQ ID NO.: 19 and (1)(b) a $C_\alpha$ domain comprising or consisting of SEQ ID NO.: 20, and a polynucleotide encoding (2) a TCR β-chain pre-protein comprising (2)(a) a $V_\beta$ domain comprising or consisting of SEQ ID NO.: 17 and (2)(b) a $C_\beta$ domain comprising or consisting of SEQ ID NO.: 18;

(ii) a polynucleotide encoding (1) a TCR α-chain pre-protein comprising (1)(a) a $V_\alpha$ domain comprising or consisting of SEQ ID NO.: 7 and (1)(b) a $C_\alpha$ domain comprising or consisting of SEQ ID NO.: 8, and a polynucleotide encoding (2) a TCR β-chain pre-protein comprising (2)(a) a $V_\beta$ domain comprising or consisting of SEQ ID NO.: 5 and (2)(b) a $C_\beta$ comprising or consisting of SEQ ID NO.: 6;

(iii) a polynucleotide encoding (1) a TCR α-chain pre-protein comprising (1)(a) a $V_\alpha$ domain comprising or consisting of SEQ ID NO.: 11 and (1)(b) a $C_\alpha$ domain comprising or consisting of SEQ ID NO.: 12, and a polynucleotide encoding (2) a TCR β-chain pre-protein comprising (2)(a) a $V_\beta$ domain comprising or consisting of SEQ ID NO.: 9 and (2)(b) a $C_\beta$ domain comprising or consisting of SEQ ID NO.: 10;

(iv) a polynucleotide encoding (1) a TCR α-chain pre-protein comprising (1)(a) a $V_\alpha$ domain comprising or consisting of SEQ ID NO.: 15 and (1)(b) a $C_\alpha$ comprising or consisting of SEQ ID NO.: 16, and a polynucleotide encoding (2) a TCR β-chain pre-protein comprising (2a) a $V_\beta$ domain comprising or consisting of SEQ ID NO.: 13 and (2)(b) a $C_\beta$ domain comprising or consisting of SEQ ID NO.: 14; or (v) a polynucleotide encoding (1) a TCR α-chain pre-protein comprising (1)(a) a $V_\alpha$ domain comprising or consisting of SEQ ID NO.: 3 and (1)(b) a $C_\alpha$ domain comprising or consisting of SEQ ID NO.: 4, and a polynucleotide encoding (2) a TCR β-chain pre-protein comprising (2)(a) a $V_\beta$ domain comprising or consisting of SEQ ID NO.: 1 and (2)(b) a $C_\beta$ domain comprising or consisting of SEQ ID NO.: 2.

11. The isolated modified cell according to claim 1, wherein the modified cell is an immune cell selected from a T cell, a NK cell, or a NK-T cell.

12. The isolated modified cell according to claim 11, wherein the immune cell is a CD4+ T cell, a CD8+ T cell, or both.

13. The isolated modified cell according to claim 12, wherein the modified cell is a CD4+ T cell and further comprises a heterologous polynucleotide encoding at least an extracellular portion of a CD8 co-receptor.

14. A composition comprising a modified cell according to claim 1 and a pharmaceutically acceptable carrier, diluent, or excipient.

15. An isolated polynucleotide encoding a binding protein having a TCR $V_\alpha$ domain and a TCR $V_\beta$ domain, wherein:
   (i) (a) the encoded $V_\alpha$ domain comprises CDR1, CDR2, and CDR3 amino acid sequences of SEQ ID NOS.:48-50, respectively, and the encoded $V_\beta$ domain comprises CDR1, CDR2, and CDR3 amino acid sequences of SEQ ID NOS.:45-47, respectively;
     (b) the encoded $V_\alpha$ domain comprises CDR1, CDR2, and CDR3 amino acid sequences of SEQ ID NOS.: 30-32, respectively, and the encoded $V_\beta$ domain comprises CDR1, CDR2, and CDR3 amino acid sequences of SEQ ID NOS.:27-29, respectively;
     (c) the encoded $V_\alpha$ domain comprises CDR1, CDR2, and CDR3 amino acid sequences of SEQ ID NOS.: 36-38, respectively, and the encoded $V_\beta$ domain comprises CDR1, CDR2, and CDR3 amino acid sequences according to SEQ ID NOS.:33-35, respectively;
     (d) the encoded $V_\alpha$ domain comprises CDR1, CDR2, and CDR3 amino acid sequences of SEQ ID NOS.: 42-44, respectively, and the encoded $V_\beta$ domain comprises CDR1, CDR2, and CDR3 amino acid sequences of SEQ ID NOS.:39-41, respectively; or
     (e) the encoded $V_\alpha$ domain comprises CDR1, CDR2, and CDR3 amino acid sequences of SEQ ID NOS.:24-26, respectively, and the encoded $V_\beta$ domain comprises CDR1, CDR2, and CDR3 amino acid sequences SEQ ID NOS.:21-23, respectively;
   (ii) the encoded binding protein is capable of specifically binding to a KVLEYVIKV (SEQ ID NO.:123): human leukocyte antigen (HLA)-A*0201 complex on a cell surface independent of CD8 or in the absence of CD8; and
   (iii) the $V_\alpha$-encoding polynucleotide comprises a nucleotide sequence having at least 80% identity to SEQ ID NO:58, 66, 74, 82, or 90, and the $V_\beta$-encoding polynucleotide comprises a nucleotide sequence having at least 80% identity to SEQ ID NQ:56, 64, 72, 80, or 88.

16. An isolated expression vector, comprising a polynucleotide according to claim 15 operably linked to an expression control sequence.

17. A method for treating a hyperproliferative disorder associated with MAGE-A1 expression, comprising administering to a human subject in need thereof a modified cell according to claim 1.

18. The method of claim 17, wherein the human subject is further receiving an anti-PD-1 antibody or an anti-PD-L1 antibody.

19. The method according to claim 17, wherein the modified cell is an immune cell selected from a T cell, a NK cell, or a NK-T cell.

20. The method according to claim 17, wherein the hyperproliferative disorder is a hematological malignancy or a solid cancer.

21. The method according to claim 20, wherein the hematological malignancy is selected from acute lymphoblastic leukemia (ALL), acute myeloid leukemia (AML), chronic myelogenous leukemia (CIVIL), chronic eosinophilic leukemia (CEL), myelodysplastic syndrome (MDS), non-Hodgkin's lymphoma (NHL), or multiple myeloma (MM).

22. The method according to claim 20, wherein the solid cancer is selected from non-small cell lung cancer (NSCLC), triple negative breast cancer (TNBC), ovarian cancer, malignant melanoma, colon cancer, colorectal adenocarcinoma, colorectal cancer, biliary cancer, bladder cancer, bone and soft tissue carcinoma, brain tumor, breast cancer, cervical cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, osteosarcoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

23. The method according to claim 19, wherein the immune cell is a human immune system cell.

24. The isolated modified cell according to claim 11, wherein the immune cell is a human immune system cell.

25. An isolated modified T cell comprising a heterologous polynucleotide encoding a binding protein, wherein the encoded binding protein comprises:
   a T cell receptor (TCR) α-chain variable (Vα) domain comprising CDR1, CDR2, and CDR3 amino acid sequences of SEQ ID NOS.:48-50, respectively; and
   (ii) a TCR β chain variable (Vβ) domain comprising CDR1, CDR2, and CDR3 amino acid sequences of SEQ ID NOS.:45-47, respectively,
   and wherein the encoded binding protein is capable of specifically binding to a KVLEYVIKV (SEQ ID NO.:123):human leukocyte antigen (HLA)-A*0201 complex on a cell surface independent of CD8 or in the absence of CD8,
   wherein the T cell is a CD4+ T cell or a CD8+ T cell.

26. The isolated modified T cell of claim 25, wherein:
   (a) the $V_\alpha$ domain comprises or consists of the amino acid sequence of SEQ ID NO.: 19, and the $V_\alpha$ domain is comprised in a TCR α-chain pre-protein that further comprises a Ca domain comprising or consisting of the amino acid sequence of SEQ ID NO.: 20; and
   (b) the $V_\beta$ domain comprises or consists of the amino acid sequence of SEQ ID NO.: 17, and the $V_\beta$ domain is comprised in a TCR β-chain pre-protein that further comprises a $C_\beta$ domain comprising or consisting of the amino acid sequence of SEQ ID NO.: 18.

27. The isolated modified cell of claim 13, wherein the encoded at least an extracellular portion of a CD8 co-receptor comprises:
   (i) the CD8 co-receptor α-chain amino acid sequence of SEQ ID NO.:143; and
   (ii) the CD8 co-receptor β-chain amino acid sequence of any one of SEQ ID NOs.:144-145.

28. The isolated polynucleotide of claim 15, wherein the encoded binding protein comprises $V_\alpha$ CDR1, CDR2, and CDR3 amino acid sequences of SEQ ID NOS.:48-50, respectively, and $V_\beta$ CDR1, CDR2, and CDR3 amino acid sequences according to SEQ ID NOS.:45-47, respectively.

29. The isolated polynucleotide of claim 28, wherein the encoded $V_\alpha$ domain comprises or consists of the amino acid sequence according to SEQ ID NO.: 19 and the encoded $V_\beta$ domain comprises or consists of the amino acid sequence according to SEQ ID NO.: 17.

30. The isolated polynucleotide of claim 15, wherein the $V_\alpha$-encoding polynucleotide comprises or consists of a nucleotide sequence having at least 80% identity to SEQ ID NO.:90, and the $V_\beta$-encoding polynucleotide comprises a nucleotide sequence having at least 80% identity to SEQ ID NO.:88.

\* \* \* \* \*

SEQUENCE LISTING

```
<160> NUMBER OF SEQ ID NOS: 148

<210> SEQ ID NO 1
<211> LENGTH: 133
<212> TYPE: PRT
<213> ORGANISM: Artificial Sequence
<220> FEATURE:
<223> OTHER INFORMATION: Synthetic sequence beta chain variable domain
      (amino acid)

<400> SEQUENCE: 1

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Asn Asn Arg Asp Ser Tyr Asn Ser Pro Leu His Phe Gly Asn Gly Thr
        115                 120                 125

Arg Leu Thr Val Thr
    130

<210> SEQ ID NO 2
<211> LENGTH: 177
<212> TYPE: PRT
<213> ORGANISM: Artificial Sequence
<220> FEATURE:
<223> OTHER INFORMATION: Synthetic sequence beta chain constant domain
```

(amino acid)

<400> SEQUENCE: 2

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 3
<211> LENGTH: 128
<212> TYPE: PRT
<213> ORGANISM: Artificial Sequence
<220> FEATURE:
<223> OTHER INFORMATION: Synthetic sequence alpha chain variable domain
      (amino acid)

<400> SEQUENCE: 3

Met Lys Pro Thr Leu Ile Ser Val Leu Val Ile Ile Phe Ile Leu Arg
1               5                   10                  15

Gly Thr Arg Ala Gln Arg Val Thr Gln Pro Glu Lys Leu Leu Ser Val
            20                  25                  30

Phe Lys Gly Ala Pro Val Glu Leu Lys Cys Asn Tyr Ser Tyr Ser Gly
        35                  40                  45

Ser Pro Glu Leu Phe Trp Tyr Val Gln Tyr Ser Arg Gln Arg Leu Gln
    50                  55                  60

Leu Leu Leu Arg His Ile Ser Arg Glu Ser Ile Lys Gly Phe Thr Ala
65                  70                  75                  80

Asp Leu Asn Lys Gly Glu Thr Ser Phe His Leu Lys Lys Pro Phe Ala
                85                  90                  95

Gln Glu Glu Asp Ser Ala Met Tyr Tyr Cys Ala Leu Arg Ser Gly Gly
            100                 105                 110

Tyr Gln Lys Val Thr Phe Gly Thr Gly Thr Lys Leu Gln Val Ile Pro
        115                 120                 125

<210> SEQ ID NO 4
<211> LENGTH: 141
<212> TYPE: PRT
<213> ORGANISM: Artificial Sequence
<220> FEATURE:
<223> OTHER INFORMATION: Synthetic sequence alpha chain constant domain
      (amino acid)

<400> SEQUENCE: 4

```
Asp Ile Gln Asn Pro Asp Pro Ala Val Tyr Gln Leu Arg Asp Ser Lys
1               5                  10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
130                 135                 140
```

<210> SEQ ID NO 5
<211> LENGTH: 130
<212> TYPE: PRT
<213> ORGANISM: Artificial Sequence
<220> FEATURE:
<223> OTHER INFORMATION: Synthetic sequence beta chain variable domain
      (amino acid)

<400> SEQUENCE: 5

```
Met Gly Phe Arg Leu Leu Cys Cys Val Ala Phe Cys Leu Leu Gly Ala
1               5                  10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Gln Gly Asp Glu Lys Leu Phe Phe Gly Ser Gly Thr Gln Leu Ser
        115                 120                 125

Val Leu
130
```

<210> SEQ ID NO 6
<211> LENGTH: 177
<212> TYPE: PRT
<213> ORGANISM: Artificial Sequence
<220> FEATURE:
<223> OTHER INFORMATION: Synthetic sequence beta chain constant domain
      (amino acid)

-continued

<400> SEQUENCE: 6

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

<210> SEQ ID NO 7
<211> LENGTH: 130
<212> TYPE: PRT
<213> ORGANISM: Artificial Sequence
<220> FEATURE:
<223> OTHER INFORMATION: Synthetic sequence alpha chain variable domain
      (amino acid)

<400> SEQUENCE: 7

```
Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ser Ile Asp Ala Arg Leu Met Phe Gly Asp Gly Thr Gln Leu Val Val
        115                 120                 125

Lys Pro
    130
```

<210> SEQ ID NO 8
<211> LENGTH: 141

<212> TYPE: PRT
<213> ORGANISM: Artificial Sequence
<220> FEATURE:
<223> OTHER INFORMATION: Synthetic sequence alpha chain constant domain
      (amino acid)

<400> SEQUENCE: 8

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
130                 135                 140

<210> SEQ ID NO 9
<211> LENGTH: 127
<212> TYPE: PRT
<213> ORGANISM: Artificial Sequence
<220> FEATURE:
<223> OTHER INFORMATION: Synthetic sequence beta chain variable domain
      (amino acid)

<400> SEQUENCE: 9

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
        35                  40                  45

Asn Leu Tyr Trp Tyr Arg Gln Ala Ala Gly Arg Gly Leu Gln Leu Leu
50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Leu Ser Thr
            100                 105                 110

Ser Tyr Glu Gln Tyr Phe Gly Pro Gly Thr Arg Leu Thr Val Thr
        115                 120                 125

<210> SEQ ID NO 10
<211> LENGTH: 178
<212> TYPE: PRT
<213> ORGANISM: Artificial Sequence
<220> FEATURE:
<223> OTHER INFORMATION: Synthetic sequence beta chain constant domain
      (amino acid)

<400> SEQUENCE: 10

```
Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Cys Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly
```

<210> SEQ ID NO 11
<211> LENGTH: 133
<212> TYPE: PRT
<213> ORGANISM: Artificial Sequence
<220> FEATURE:
<223> OTHER INFORMATION: Synthetic sequence slpha chain variable domain
      (amino acid)

<400> SEQUENCE: 11

```
Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Asn Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Met Lys Ser His Ser Gly Tyr Ile Phe Gly Thr Gly Thr Arg
        115                 120                 125

Leu Lys Val Leu Ala
    130
```

<210> SEQ ID NO 12
<211> LENGTH: 141
<212> TYPE: PRT

<213> ORGANISM: Artificial Sequence
<220> FEATURE:
<223> OTHER INFORMATION: Synthetic sequence alpha chain constant domain
      (amino acid)

<400> SEQUENCE: 12

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 13
<211> LENGTH: 129
<212> TYPE: PRT
<213> ORGANISM: Artificial Sequence
<220> FEATURE:
<223> OTHER INFORMATION: Synthetic sequence beta chain variable domain
      (amino acid)

<400> SEQUENCE: 13

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
        35                  40                  45

Asn Leu Tyr Trp Tyr Arg Gln Ala Ala Gly Arg Gly Leu Gln Leu Leu
    50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Val
            100                 105                 110

Ala Val Asn Thr Glu Ala Phe Phe Gly Gln Gly Thr Arg Leu Thr Val
        115                 120                 125

Val

<210> SEQ ID NO 14
<211> LENGTH: 177
<212> TYPE: PRT
<213> ORGANISM: Artificial Sequence
<220> FEATURE:
<223> OTHER INFORMATION: Synthetic sequence beta chain constant domain
      (amino acid)

<400> SEQUENCE: 14

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65              70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

<210> SEQ ID NO 15
<211> LENGTH: 132
<212> TYPE: PRT
<213> ORGANISM: Artificial Sequence
<220> FEATURE:
<223> OTHER INFORMATION: Synthetic sequence alpha chain variable domain
      (amino acid)

<400> SEQUENCE: 15

```
Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Asn Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65              70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Gly Glu Gly Ala Arg Leu Met Phe Gly Asp Gly Thr Gln Leu
        115                 120                 125

Val Val Lys Pro
    130
```

<210> SEQ ID NO 16
<211> LENGTH: 141

<212> TYPE: PRT
<213> ORGANISM: Artificial Sequence
<220> FEATURE:
<223> OTHER INFORMATION: Synthetic sequence alpha chain constant domain
     (amino acid)

<400> SEQUENCE: 16

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 17
<211> LENGTH: 129
<212> TYPE: PRT
<213> ORGANISM: Artificial Sequence
<220> FEATURE:
<223> OTHER INFORMATION: Synthetic sequence beta chain variable domain
     (amino acid)

<400> SEQUENCE: 17

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
            20                  25                  30

Gly Ser Pro Leu Ser Leu Glu Cys Thr Val Glu Gly Thr Ser Asn Pro
        35                  40                  45

Asn Leu Tyr Trp Tyr Arg Gln Ala Ala Gly Arg Gly Leu Gln Leu Leu
    50                  55                  60

Phe Tyr Ser Ile Gly Ile Asp Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Val
            100                 105                 110

Thr Arg His Asn Glu Gln Phe Phe Gly Pro Gly Thr Arg Leu Thr Val
        115                 120                 125

Leu

<210> SEQ ID NO 18
<211> LENGTH: 178
<212> TYPE: PRT
<213> ORGANISM: Artificial Sequence
<220> FEATURE:
<223> OTHER INFORMATION: Synthetic sequence beta chain constant domain -continued (amino acid)

<400> SEQUENCE: 18

Asp Leu Lys Asn Val Phe Pro Pro Glu Val Ala Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Cys Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 19
<211> LENGTH: 135
<212> TYPE: PRT
<213> ORGANISM: Artificial Sequence
<220> FEATURE:
<223> OTHER INFORMATION: Synthetic sequence alpha chain variable domain
      (amino acid)

<400> SEQUENCE: 19

Met Leu Cys Ser Leu Leu Ala Leu Leu Leu Gly Thr Phe Phe Glu Pro
1               5                   10                  15

Arg Thr Ser Gln Glu Leu Glu Gln Ser Pro Gln Ser Leu Ile Val Gln
            20                  25                  30

Glu Gly Lys Asn Leu Thr Ile Asn Cys Thr Ser Ser Lys Thr Leu Tyr
        35                  40                  45

Gly Leu Tyr Trp Tyr Lys Gln Lys Tyr Gly Glu Gly Leu Ile Phe Leu
    50                  55                  60

Met Met Leu Gln Lys Gly Gly Glu Glu Lys Ser His Glu Lys Ile Thr
65                  70                  75                  80

Ala Lys Leu Asp Glu Lys Lys Gln Gln Ser Ser Leu His Ile Thr Ala
                85                  90                  95

Ser Gln Pro Ser His Ala Gly Ile Tyr Leu Cys Gly Ala Ala Pro Thr
            100                 105                 110

Tyr Ser Asn Tyr Gly Gly Ser Gln Gly Asn Leu Ile Phe Gly Lys Gly
        115                 120                 125

Thr Lys Leu Ser Val Lys Pro
    130                 135

<210> SEQ ID NO 20

```
<211> LENGTH: 141
<212> TYPE: PRT
<213> ORGANISM: Artificial Sequence
<220> FEATURE:
<223> OTHER INFORMATION: Synthetic sequence alpha chain constant domain
      (amino acid)

<400> SEQUENCE: 20

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 21
<211> LENGTH: 5
<212> TYPE: PRT
<213> ORGANISM: Artificial Sequence
<220> FEATURE:
<223> OTHER INFORMATION: Synthetic sequence 1388.1 beta chain CDR1
      domain (amino acid)

<400> SEQUENCE: 21

Met Asp His Glu Asn
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic sequence 1388.1 beta chain CDR2
      domain (amino acid)

<400> SEQUENCE: 22

Ser Tyr Asp Val Lys Met
1               5

<210> SEQ ID NO 23
<211> LENGTH: 15
<212> TYPE: PRT
<213> ORGANISM: Artificial Sequence
<220> FEATURE:
<223> OTHER INFORMATION: Synthetic sequence 1388.1 beta chain CDR3
      domain (amino acid)

<400> SEQUENCE: 23

Cys Ala Ser Asn Asn Arg Asp Ser Tyr Asn Ser Pro Leu His Phe
1               5                   10                  15
```

```
<210> SEQ ID NO 24
<211> LENGTH: 6
<212> TYPE: PRT
<213> ORGANISM: Artificial Sequence
<220> FEATURE:
<223> OTHER INFORMATION: Synthetic sequence 1388.1 alpha chain CDR1
      domain (amino acid)

<400> SEQUENCE: 24

Tyr Ser Gly Ser Pro Glu
1               5

<210> SEQ ID NO 25
<211> LENGTH: 4
<212> TYPE: PRT
<213> ORGANISM: Artificial Sequence
<220> FEATURE:
<223> OTHER INFORMATION: Synthetic sequence 1388.1 alpha chain CDR2
      domain (amino acid)

<400> SEQUENCE: 25

His Ile Ser Arg
1

<210> SEQ ID NO 26
<211> LENGTH: 13
<212> TYPE: PRT
<213> ORGANISM: Artificial Sequence
<220> FEATURE:
<223> OTHER INFORMATION: Synthetic sequence 1388.1 alpha chain CDR3
      domain (amino acid)

<400> SEQUENCE: 26

Cys Ala Leu Arg Ser Gly Gly Tyr Gln Lys Val Thr Phe
1               5                   10

<210> SEQ ID NO 27
<211> LENGTH: 5
<212> TYPE: PRT
<213> ORGANISM: Artificial Sequence
<220> FEATURE:
<223> OTHER INFORMATION: Synthetic sequence 1388.2b beta chain CDR1
      domain (amino acid)

<400> SEQUENCE: 27

Ser Gly Asp Leu Ser
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic sequence 1388.2b beta chain CDR2
      domain (amino acid)

<400> SEQUENCE: 28

Tyr Tyr Asn Gly Glu Glu
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic sequence 1388.2b beta chain CDR3
      domain (amino acid)

<400> SEQUENCE: 29
```

```
Cys Ala Ser Ser Gln Gly Asp Glu Lys Leu Phe Phe
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Synthetic sequence 1388.2b alpha chain CDR1
      domain (amino acid)

<400> SEQUENCE: 30

Asp Ser Ser Ser Thr Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic sequence 1388.2b alpha chain CDR2
      domain (amino acid)

<400> SEQUENCE: 31

Ile Phe Ser Asn Met Asp Met
1               5

<210> SEQ ID NO 32
<211> LENGTH: 11
<212> TYPE: PRT
<213> ORGANISM: Artificial Sequence
<220> FEATURE:
<223> OTHER INFORMATION: Synthetic sequence 1388.2b alpha chain CDR3
      domain (amino acid)

<400> SEQUENCE: 32

Cys Ala Glu Ser Ile Asp Ala Arg Leu Met Phe
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Synthetic sequence 1388.3 beta chain CDR1
      domain (amino acid)

<400> SEQUENCE: 33

Gly Thr Ser Asn Pro Asn
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic sequence 1388.3 beta chain CDR2
      domain (amino acid)

<400> SEQUENCE: 34

Ser Val Gly Ile Gly
1               5

<210> SEQ ID NO 35
<211> LENGTH: 11
<212> TYPE: PRT
<213> ORGANISM: Artificial Sequence
```

```
<220> FEATURE:
<223> OTHER INFORMATION: Synthetic sequence 1388.3 beta chain CDR3
      domain (amino acid)

<400> SEQUENCE: 35

Cys Ala Leu Ser Thr Ser Tyr Glu Gln Tyr Phe
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic sequence 1388.3 alpha chain CDR1
      domain (amino acid)

<400> SEQUENCE: 36

Thr Ser Glu Asn Asn Tyr Tyr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic sequence 1388.3 alpha chain CDR2
      domain (amino acid)

<400> SEQUENCE: 37

Gln Glu Ala Tyr Lys Gln Gln Asn
1               5

<210> SEQ ID NO 38
<211> LENGTH: 12
<212> TYPE: PRT
<213> ORGANISM: Artificial Sequence
<220> FEATURE:
<223> OTHER INFORMATION: Synthetic sequence 1388.3 alpha chain CDR3
      domain (amino acid)

<400> SEQUENCE: 38

Cys Ala Phe Met Lys Ser His Ser Gly Tyr Ile Phe
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Synthetic sequence 17804.1b beta chain CDR1
      domain (amino acid)

<400> SEQUENCE: 39

Gly Thr Ser Asn Pro Asn
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic sequence 17804.1b beta chain CDR2
      domain (amino acid)

<400> SEQUENCE: 40

Ser Val Gly Ile Gly
1               5
```

<210> SEQ ID NO 41
<211> LENGTH: 13
<212> TYPE: PRT
<213> ORGANISM: Artificial Sequence
<220> FEATURE:
<223> OTHER INFORMATION: Synthetic sequence 17804.1b beta chain CDR3
      domain (amino acid)

<400> SEQUENCE: 41

Cys Ala Trp Ser Val Ala Val Asn Thr Glu Ala Phe Phe
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Synthetic sequence 17804.1b alpha chain CDR1
      domain (amino acid)

<400> SEQUENCE: 42

Thr Ser Glu Asn Asn Tyr Tyr
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic sequence 17804.1b alpha chain CDR2
      domain (amino acid)

<400> SEQUENCE: 43

Gln Glu Ala Tyr Lys Gln Gln Asn
1               5

<210> SEQ ID NO 44
<211> LENGTH: 11
<212> TYPE: PRT
<213> ORGANISM: Artificial Sequence
<220> FEATURE:
<223> OTHER INFORMATION: Synthetic sequence 17804.1b alpha chain CDR3
      domain (amino acid)

<400> SEQUENCE: 44

Cys Ala Phe Gly Glu Gly Ala Arg Leu Met Phe
1               5                   10

<210> SEQ ID NO 45
<211> LENGTH: 6
<212> TYPE: PRT
<213> ORGANISM: Artificial Sequence
<220> FEATURE:
<223> OTHER INFORMATION: Synthetic sequence 17804.2 beta chain CDR1
      domain (amino acid)

<400> SEQUENCE: 45

Gly Thr Ser Asn Pro Asn
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic sequence 17804.2 beta chain CDR2
      domain (amino acid)

```
<400> SEQUENCE: 46

Ser Ile Gly Ile Asp
1               5

<210> SEQ ID NO 47
<211> LENGTH: 13
<212> TYPE: PRT
<213> ORGANISM: Artificial Sequence
<220> FEATURE:
<223> OTHER INFORMATION: Synthetic sequence 17804.2 beta chain CDR3
      domain (amino acid)

<400> SEQUENCE: 47

Cys Ala Trp Ser Val Thr Arg His Asn Glu Gln Phe Phe
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Synthetic sequence 17804.2 alpha chain CDR1
      domain (amino acid)

<400> SEQUENCE: 48

Lys Thr Leu Tyr Gly
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic sequence 17804.2 alpha chain CDR2
      domain (amino acid)

<400> SEQUENCE: 49

Leu Gln Lys Gly Gly Glu Glu
1               5

<210> SEQ ID NO 50
<211> LENGTH: 19
<212> TYPE: PRT
<213> ORGANISM: Artificial Sequence
<220> FEATURE:
<223> OTHER INFORMATION: Synthetic sequence 17804.2 alpha chain CDR3
      domain (amino acid)

<400> SEQUENCE: 50

Cys Gly Ala Ala Pro Thr Tyr Ser Asn Tyr Gly Gly Ser Gln Gly Asn
1               5                   10                  15

Leu Ile Phe

<210> SEQ ID NO 51
<211> LENGTH: 14
<212> TYPE: PRT
<213> ORGANISM: Artificial Sequence
<220> FEATURE:
<223> OTHER INFORMATION: Synthetic sequence 18648.2 alpha chain CDR3
      domain (amino acid)

<400> SEQUENCE: 51

Cys Ala Leu Arg Gly Leu Asn Tyr Gly Gln Asn Phe Val Phe
1               5                   10

<210> SEQ ID NO 52
```

<211> LENGTH: 399
<212> TYPE: DNA
<213> ORGANISM: Artificial Sequence
<220> FEATURE:
<223> OTHER INFORMATION: Synthetic sequence 1388.1 beta chain variable domain

<400> SEQUENCE: 52

```
atgggaatca ggctcctctg tcgtgtggcc ttttgtttcc tggctgtagg cctcgtagat      60
gtgaaagtaa cccagagctc gagatatcta gtcaaaagga cgggagagaa agttttctg     120
gaatgtgtcc aggatatgga ccatgaaaat atgttctggt atcgacaaga cccaggtctg    180
gggctacggc tgatctattt ctcatatgat gttaaaatga agaaaaagg agatattcct     240
gaggggtaca gtgtctctag agagaagaag gagcgcttct ccctgattct ggagtccgcc    300
agcaccaacc agacatctat gtacctctgc gccagcaaca cagagacag ctacaacagc     360
cccctccact ttgggaacgg gaccaggctc actgtgacg                           399
```

<210> SEQ ID NO 53
<211> LENGTH: 531
<212> TYPE: DNA
<213> ORGANISM: Artificial Sequence
<220> FEATURE:
<223> OTHER INFORMATION: Synthetic sequence 1388.1 beta chain constant domain (Native NA)

<400> SEQUENCE: 53

```
gaggacctga acaaagtgtt ccccccagag gtggccgtgt tcgagccttc tgaggccgag      60
atcagccaca cccagaaagc caccctcgtg tgcctggcca ccggcttttt ccccgaccac    120
gtggaactgt cttggtgggt caacggcaaa gaggtgcact ccggcgtgtg caccgatccc    180
cagcctctga agaacagcc cgccctgaac gacagccggt actgcctgtc agcagactg      240
agagtgtccg ccaccttctg cagaaccccc ggaaccact tcagatgcca ggtgcagttc     300
tacggcctga gcgagaacga cgagtggacc caggacagag ccaagcccgt gacacagatc    360
gtgtctgccg aagcctgggg cagagccgat tgcggcttta cctccgtgtc ctatcagcag    420
ggcgtgctga cgccaccat cctgtacgag atcctgctgg caaggccac actgtacgcc      480
gtgctggtgt ctgccctggt gctgatggcc atggtcaagc ggaaggactt c             531
```

<210> SEQ ID NO 54
<211> LENGTH: 384
<212> TYPE: DNA
<213> ORGANISM: Artificial Sequence
<220> FEATURE:
<223> OTHER INFORMATION: Synthetic sequence 1388.1 alpha chain variable domain (Native NA)

<400> SEQUENCE: 54

```
atgaagccca ccctcatctc agtgcttgtg ataatattta tactcagagg aacaagagcc      60
cagagagtga ctcagcccga gaagctcctc tctgtcttta aggggcccc agtggagctg     120
aagtgcaact attcctattc tgggagtcct gaactcttct ggtatgtcca gtactccaga    180
caacgcctcc agttactctt gagacacatc tctagagaga gcatcaaagg cttcactgct    240
gaccttaaca aaggcgagac atctttccac ctgaagaaac catttgctca agaggaagac    300
tcagccatgt attactgcgc cctgagaagc ggcggctacc agaaggtgac ctttggaact    360
ggaacaaagc tccaagtcat ccca                                           384
```

<210> SEQ ID NO 55

<211> LENGTH: 426
<212> TYPE: DNA
<213> ORGANISM: Artificial Sequence
<220> FEATURE:
<223> OTHER INFORMATION: Synthetic sequence 1388.1 alpha chain constant
      domain (Native NA)

<400> SEQUENCE: 55

```
gatatccaga accctgaccc tgccgtgtac cagctgagag actctaaatc cagtgacaag      60
tctgtctgcc tattcaccga ttttgattct caaacaaatg tgtcacaaag taaggattct     120
gatgtgtata tcacagacaa atgtgtgcta gacatgaggt ctatggactt caagagcaac     180
agtgctgtgg cctggagcaa caaatctgac tttgcatgtg caaacgcctt caacaacagc     240
attattccag aagacacctt cttccccagc ccagaaagtt cctgtgatgt caagctggtc     300
gagaaaagct ttgaaacaga tacgaaccta aactttcaaa acctgtcagt gattgggttc     360
cgaatcctcc tcctgaaagt ggccgggttt aatctgctca tgacgctgcg gctgtggtcc     420
agctga                                                                426
```

<210> SEQ ID NO 56
<211> LENGTH: 399
<212> TYPE: DNA
<213> ORGANISM: Artificial Sequence
<220> FEATURE:
<223> OTHER INFORMATION: Synthetic sequence 1388.1 beta chain variable
      domain (Codon-optimized NA)

<400> SEQUENCE: 56

```
atgggaatta gactgctgtg ccgggtggcc ttctgcttcc tggctgtggg actggtggac      60
gtgaaagtga cccagagcag cagatacctc gtgaagcgga ccggcgagaa ggtgttcctg     120
gaatgcgtgc aggacatgga ccacgagaat atgttctggt acagacagga ccccggcctg     180
ggcctgcggc tgatctactt cagctacgac gtgaagatga aggaaaaggg cgacatcccc     240
gagggctaca cgtgtccag agagaagaa gagcggttca gcctgatcct ggaaagcgcc     300
agcaccaacc agaccagcat gtacctgtgc gcctccaaca ccgggacag ctacaacagc     360
cccctgcact cggcaacgg caccagactg accgtgacc                             399
```

<210> SEQ ID NO 57
<211> LENGTH: 531
<212> TYPE: DNA
<213> ORGANISM: Artificial Sequence
<220> FEATURE:
<223> OTHER INFORMATION: Synthetic sequence 1388.1 beta chain constant
      domain (Codon-optimized NA)

<400> SEQUENCE: 57

```
gaggacctga acaaagtgtt ccccccagag gtggccgtgt cgagccttc tgaggccgag       60
atcagccaca cccagaaagc caccctcgtg tgcctggcca ccggcttttt ccccgaccac     120
gtggaactgt cttggtgggt caacggcaaa gaggtgcact ccggcgtgtg caccgatccc     180
cagcctctga agaacagcc cgccctgaac gacagccggt actgcctgtc cagcagactg     240
agagtgtccg ccaccttctg gcagaacccc cggaaccact tcagatgcca ggtgcagttc     300
tacggcctga gcgagaacga cgagtggacc caggacagag ccaagcccgt gacacagatc     360
gtgtctgccg aagcctgggg cagagccgat tgcggcttta cctccgtgtc ctatcagcag     420
ggcgtgctga gcgccaccat cctgtacgag atcctgctgg gcaaggccac actgtacgcc     480
gtgctggtgt ctgccctggt gctgatggcc atggtcaagc ggaaggactt c              531
```

<210> SEQ ID NO 58
<211> LENGTH: 390
<212> TYPE: DNA
<213> ORGANISM: Artificial Sequence
<220> FEATURE:
<223> OTHER INFORMATION: Synthetic sequence 1388.2b alpha chain variable
      domain (Native NA)

<400> SEQUENCE: 58

| atgaagacat | ttgctggatt | ttcgttcctg | tttttgtggc | tgcagctgga | ctgtatgagt | 60 |
| agaggagagg | atgtggagca | gagtcttttc | ctgagtgtcc | gagagggaga | cagctccgtt | 120 |
| ataaactgca | cttacacaga | cagctcctcc | acctacttat | actggtataa | gcaagaacct | 180 |
| ggagcaggtc | tccagttgct | gacgtatatt | ttttcaaata | tggacatgaa | acaagaccaa | 240 |
| agactcactg | ttctattgaa | taaaaaggat | aaacatctgt | ctctgcgcat | tgcagacacc | 300 |
| cagactgggg | actcagctat | ctacttctgt | gcagagagta | tcgatgccag | actcatgttt | 360 |
| ggagatggaa | ctcagctggt | ggtgaagccc | | | | 390 |

<210> SEQ ID NO 59
<211> LENGTH: 426
<212> TYPE: DNA
<213> ORGANISM: Artificial Sequence
<220> FEATURE:
<223> OTHER INFORMATION: Synthetic sequence 1388.1 alpha chain constant
      domain (Codon-optimized NA)

<400> SEQUENCE: 59

| gacatccaga | accccgaccc | tgcagtgtac | cagctgcggg | acagcaagag | cagcgacaag | 60 |
| agcgtgtgcc | tgttcaccga | cttcgacagc | cagaccaacg | tgtcccagag | caaggacagc | 120 |
| gacgtgtaca | tcaccgataa | gtgcgtgctg | gacatgcgga | gcatggactt | caagagcaac | 180 |
| agcgccgtgg | cctggtccaa | caagagcgac | ttcgcctgcg | ccaacgcctt | caacaacagc | 240 |
| attatccccg | aggacacatt | cttcccaagc | cccgagagca | gctgcgacgt | gaagctggtg | 300 |
| gaaaagagct | tcgagacaga | caccaacctg | aacttccaga | acctcagcgt | gatcggcttc | 360 |
| cggatcctgc | tgctgaaggt | ggccggcttc | aacctgctga | tgaccctgcg | gctgtggtcc | 420 |
| agctga | | | | | | 426 |

<210> SEQ ID NO 60
<211> LENGTH: 390
<212> TYPE: DNA
<213> ORGANISM: Artificial Sequence
<220> FEATURE:
<223> OTHER INFORMATION: Synthetic sequence 1388.2b beta chain variable
      domain (Native NA)

<400> SEQUENCE: 60

| atgggcttca | ggctcctctg | ctgtgtggcc | ttttgtctcc | tgggagcagg | cccagtggat | 60 |
| tctggagtca | cacaaacccc | aaagcacctg | atcacagcaa | ctggacagcg | agtgacgctg | 120 |
| agatgctccc | ctaggtctgg | agacctctct | gtgtactggt | accaacagag | cctggaccag | 180 |
| ggcctccagt | tcctcattca | gtattataat | ggagaagaga | gagcaaaagg | aaacattctt | 240 |
| gaacgattct | ccgcacaaca | gttccctgac | ttgcactctg | aactaaacct | gagctctctg | 300 |
| gagctggggg | actcagcttt | gtatttctgt | gccagcagcc | aggggatga | aaaactgttt | 360 |
| tttggcagtg | gaacccagct | ctctgtcttg | | | | 390 |

<210> SEQ ID NO 61

<211> LENGTH: 531
<212> TYPE: DNA
<213> ORGANISM: Artificial Sequence
<220> FEATURE:
<223> OTHER INFORMATION: Synthetic sequence 1388.2b beta chain constant domain (Native NA)

<400> SEQUENCE: 61

| gaggacctga | acaaagtgtt | cccccagag | gtggccgtgt | tcgagccttc | tgaggccgag | 60 |
| atcagccaca | cccagaaagc | caccctcgtg | tgcctggcca | ccggctttt | ccccgaccac | 120 |
| gtggaactgt | cttggtgggt | caacggcaaa | gaggtgcact | ccggcgtgtg | caccgatccc | 180 |
| cagcctctga | agaacagcc | cgccctgaac | gacagccggt | actgcctgtc | cagcagactg | 240 |
| agagtgtccg | ccaccttctg | gcagaacccc | cggaaccact | tcagatgcca | ggtgcagttc | 300 |
| tacggcctga | gcgagaacga | cgagtggacc | caggacagag | ccaagcccgt | gacacagatc | 360 |
| gtgtctgccg | aagcctgggg | cagagccgat | tgcggcttta | cctccgtgtc | ctatcagcag | 420 |
| ggcgtgctga | cgccaccat | cctgtacgag | atcctgctgg | caaggccac | actgtacgcc | 480 |
| gtgctggtgt | ctgccctggt | gctgatggcc | atggtcaagc | ggaaggactt | c | 531 |

<210> SEQ ID NO 62
<211> LENGTH: 390
<212> TYPE: DNA
<213> ORGANISM: Artificial Sequence
<220> FEATURE:
<223> OTHER INFORMATION: Synthetic sequence 1388.2b alpha chain variable domain (Native NA)

<400> SEQUENCE: 62

| atgaagacat | ttgctggatt | ttcgttcctg | tttttgtggc | tgcagctgga | ctgtatgagt | 60 |
| agaggagagg | atgtggagca | gagtcttttc | ctgagtgtcc | gagagggaga | cagctccgtt | 120 |
| ataaactgca | cttacacaga | cagctcctcc | acctactat | actggtataa | gcaagaacct | 180 |
| ggagcaggtc | tccagttgct | gacgtatatt | ttttcaaata | tggacatgaa | acaagaccaa | 240 |
| agactcactg | ttctattgaa | taaaaggat | aaacatctgt | ctctgcgcat | tgcagacacc | 300 |
| cagactgggg | actcagctat | ctacttctgt | gcagagagta | tcgatgccag | actcatgttt | 360 |
| ggagatggaa | ctcagctggt | ggtgaagccc | | | | 390 |

<210> SEQ ID NO 63
<211> LENGTH: 426
<212> TYPE: DNA
<213> ORGANISM: Artificial Sequence
<220> FEATURE:
<223> OTHER INFORMATION: Synthetic sequence 1388.2b alpha chain constant domain (Native NA)

<400> SEQUENCE: 63

| gatatccaga | accctgaccc | tgccgtgtac | cagctgagag | actctaaatc | cagtgacaag | 60 |
| tctgtctgcc | tattcaccga | ttttgattct | caaacaaatg | tgtcacaaag | taaggattct | 120 |
| gatgtgtata | tcacagacaa | atgtgtgcta | gacatgaggt | ctatggactt | caagagcaac | 180 |
| agtgctgtgg | cctggagcaa | caaatctgac | tttgcatgtg | caaacgcctt | caacaacagc | 240 |
| attattccag | aagacacctt | cttccccagc | ccagaaagtt | cctgtgatgt | caagctggtc | 300 |
| gagaaaagct | ttgaaacaga | tacgaaccta | aactttcaaa | acctgtcagt | gattgggttc | 360 |
| cgaatcctcc | tcctgaaagt | ggccgggttt | aatctgctca | tgacgctgcg | gctgtggtcc | 420 |
| agctga | | | | | | 426 |

<210> SEQ ID NO 64
<211> LENGTH: 390
<212> TYPE: DNA
<213> ORGANISM: Artificial Sequence
<220> FEATURE:
<223> OTHER INFORMATION: Synthetic sequence 1388.2b beta chain variable
domain(Codon-optimized NA)

<400> SEQUENCE: 64

```
atgggcttca gactgctgtg ctgcgtggcc ttctgtctgc tgggagccgg ccctgtggat      60
agcggcgtga cacagacacc caagcacctg atcaccgcca ccggccagcg cgtgacactg     120
agatgtagcc ctagaagcgg cgacctgagc gtgtactggt atcagcagag cctggaccag     180
ggcctgcagt tcctgatcca gtactacaac ggcgaggaac gggccaaggg caacatcctg     240
gaacggttca cgcccagca gttccccgat ctgcacagcg agctgaacct gagcagcctg     300
gaactgggcg acagcgccct gtacttctgt gccagttctc agggcgacga agctgttc      360
ttcggcagcg gcacacagct gagcgtgctg                                      390
```

<210> SEQ ID NO 65
<211> LENGTH: 531
<212> TYPE: DNA
<213> ORGANISM: Artificial Sequence
<220> FEATURE:
<223> OTHER INFORMATION: Synthetic sequence 1388.2b beta chain constant
domain (Codon-optimized NA)

<400> SEQUENCE: 65

```
gaagatctga caaggtgtt ccccccagag gtggccgtgt cgagccttc tgaggccgag       60
atcagccaca cccagaaagc caccctcgtg tgcctggcca ccggctttt ccccgaccac     120
gtggaactgt cttggtgggt caacggcaaa gaggtgcact ccggcgtgtg caccgatccc     180
cagcctctga agaacagcc cgccctgaac gacagccggt actgcctgtc agcagactg      240
agagtgtccg ccaccttctg gcagaacccc cggaaccact tcagatgcca ggtgcagttc     300
tacggcctga gcgagaacga cgagtggacc caggacagag ccaagcccgt gacccagatc     360
gtgtctgccg aagcctgggg cagagccgat tgcggcttta ccagcgtgtc ctatcagcag     420
ggcgtgctga gcgccaccat cctgtacgag atcctgctgg gcaaggccac cctgtacgcc     480
gtgctggtgt ctgccctggt gctgatggcc atggtcaagc ggaaggactt c             531
```

<210> SEQ ID NO 66
<211> LENGTH: 390
<212> TYPE: DNA
<213> ORGANISM: Artificial Sequence
<220> FEATURE:
<223> OTHER INFORMATION: Synthetic sequence 1388.2b alpha chain variable
domain (Codon-optimized NA)

<400> SEQUENCE: 66

```
atgaagacct cgccggctt cagcttcctg ttcctgtggc tgcagctgga ctgcatgagc       60
agaggcgagg acgtggaaca gagcctgttt ctgtccgtgc gcgagggcga ctccagcgtg     120
atcaattgca cctacaccga cagcagcagc acctacctgt attggtacaa gcaggaaccc     180
ggcgctggcc tgcagctgct gacctacatc ttcagcaaca tggacatgaa gcaggaccag     240
cggctgaccg tgctgctgaa caagaaggat aagcacctgt ccctgcggat cgccgatacc     300
cagacaggcg actccgccat ctacttttgc gccgagagca tcgacgcccg gctgatgttt     360
ggagatggca cccagctggt cgtgaagccc                                      390
```

<210> SEQ ID NO 67
<211> LENGTH: 426
<212> TYPE: DNA
<213> ORGANISM: Artificial Sequence
<220> FEATURE:
<223> OTHER INFORMATION: Synthetic sequence 1388.2b alpha chain constant
      domain (Codon-optimized NA)

<400> SEQUENCE: 67

| gacatccaga | accccgaccc | tgcagtgtac | cagctgcggg | acagcaagag | cagcgacaag | 60 |
| agcgtgtgcc | tgttcaccga | cttcgacagc | cagaccaacg | tgtcccagag | caaggacagc | 120 |
| gacgtgtaca | tcaccgataa | gtgcgtgctg | gacatgcgga | gcatggactt | caagagcaac | 180 |
| agcgccgtgg | cctggtccaa | caagagcgac | ttcgcctgcg | ccaacgcctt | caacaacagc | 240 |
| attatccccg | aggacacatt | cttcccaagc | cccgagagca | gctgcgacgt | gaagctggtg | 300 |
| gaaaagagct | tcgagacaga | caccaacctg | aacttccaga | acctcagcgt | gatcggcttc | 360 |
| cggatcctgc | tgctgaaggt | ggccggcttc | aacctgctga | tgaccctgcg | gctgtggtcc | 420 |
| agctga     |            |            |            |            |            | 426 |

<210> SEQ ID NO 68
<211> LENGTH: 381
<212> TYPE: DNA
<213> ORGANISM: Artificial Sequence
<220> FEATURE:
<223> OTHER INFORMATION: Synthetic sequence 1388.3 beta chain variable
      domain (Native NA)

<400> SEQUENCE: 68

| atgctctgct | ctctccttgc | ccttctcctg | ggcactttct | ttggggtcag | atctcagact | 60 |
| attcatcaat | ggccagcgac | cctggtgcag | cctgtgggca | gcccgctctc | tctggagtgc | 120 |
| actgtggagg | gaacatcaaa | ccccaaccta | tactggtacc | gacaggctgc | aggcagggc  | 180 |
| ctccagctgc | tcttctactc | cgttggtatt | ggcagatca  | gctctgaggt | gccccagaat | 240 |
| ctctcagcct | ccagaccca  | ggaccggcag | ttcatcctga | gttctaagaa | gctccttctc | 300 |
| agtgactctg | gcttctatct | ctgcgccctg | agcaccagct | acgagcagta | cttcgggccg | 360 |
| ggcaccaggc | tcacggtcac | a          |            |            |            | 381 |

<210> SEQ ID NO 69
<211> LENGTH: 537
<212> TYPE: DNA
<213> ORGANISM: Artificial Sequence
<220> FEATURE:
<223> OTHER INFORMATION: Synthetic sequence 1388.3 beta chain constant
      domain (Native NA)

<400> SEQUENCE: 69

| gacctgaaaa | acgtgttccc | acccgaggtc | gctgtgtttg | agccatcaga | agcagagatc | 60 |
| tcccacaccc | aaaaggccac | actggtgtgc | ctggccacag | gcttctaccc | cgaccacgtg | 120 |
| gagctgagct | ggtgggtgaa | tgggaaggag | gtgcacagtg | ggtctgcac  | agaccccgcag | 180 |
| cccctcaagg | agcagcccgc | cctcaatgac | tccagatact | gcctgagcag | ccgcctgagg | 240 |
| gtctcggcca | ccttctggca | gaaccccgc  | aaccacttcc | gctgtcaagt | ccagttctac | 300 |
| gggctctcgg | agaatgacga | gtggaccag  | gatagggcca | aacctgtcac | ccagatcgtc | 360 |
| agcgccgagg | cctggggtag | agcagactgt | ggcttcacct | ccgagtctta | ccagcaaggg | 420 |
| gtcctgtctg | ccaccatcct | ctatgagatc | ttgctaggga | aggccacctt | gtatgccgtg | 480 | ctggtcagtg ccctcgtgct gatggccatg gtcaagagaa aggattccag aggctag      537

<210> SEQ ID NO 70
<211> LENGTH: 399
<212> TYPE: DNA
<213> ORGANISM: Artificial Sequence
<220> FEATURE:
<223> OTHER INFORMATION: Synthetic sequence 1388.3 alpha chain variable
      domain (Native NA)

<400> SEQUENCE: 70
atgacacgag ttagcttgct gtgggcagtc gtggtctcca cctgtcttga atccggcatg     60
gcccagacag tcactcagtc tcaaccagag atgtctgtgc aggaggcaga gactgtgacc    120
ctgagttgca catatgacac cagtgagaat aattattatt tgttctggta caagcagcct    180
cccagcaggc agatgattct cgttattcgc caagaagctt ataagcaaca gaatgcaacg    240
gagaatcgtt tctctgtgaa cttccagaaa gcagccaaat ccttcagtct caagatctca    300
gactcacagc tgggggacac tgcgatgtat ttctgtgctt tcatgaagtc ccactccgga    360
tacatctttg gaacaggcac caggctgaag gttttagca                           399

<210> SEQ ID NO 71
<211> LENGTH: 426
<212> TYPE: DNA
<213> ORGANISM: Artificial Sequence
<220> FEATURE:
<223> OTHER INFORMATION: Synthetic sequence 1388.3 alpha chain constant
      domain (Native NA)

<400> SEQUENCE: 71
gatatccaga accctgaccc tgccgtgtac cagctgagag actctaaatc cagtgacaag     60
tctgtctgcc tattcaccga ttttgattct caaacaaatg tgtcacaaag taaggattct    120
gatgtgtata tcacagacaa atgtgtgcta gacatgaggt ctatggactt caagagcaac    180
agtgctgtgg cctggagcaa caaatctgac tttgcatgtg caaacgcctt caacaacagc    240
attattccag aagacacctt cttccccagc cagaaagtt cctgtgatgt caagctggtc    300
gagaaaagct tgaaacagat acgaaccta aactttcaaa acctgtcagt gattgggttc    360
cgaatcctcc tcctgaaagt ggccgggttt aatctgctca tgacgctgcg gctgtggtcc    420
agctga                                                              426

<210> SEQ ID NO 72
<211> LENGTH: 381
<212> TYPE: DNA
<213> ORGANISM: Artificial Sequence
<220> FEATURE:
<223> OTHER INFORMATION: Synthetic sequence 1388.3 beta chain variable
      domain(Codon-optimized NA)

<400> SEQUENCE: 72
atgctgtgtt ctctgctggc cctgctgctg ggcaccttct ttggagtgcg gagccagacc     60
atccaccagt ggcctgctac actggtgcag cctgtgggca ccctctgag cctggaatgt    120 accgtggaag gcaccagcaa ccccaacctg tactggtaca gcaggccgc tggcagaggc    180 ctgcagctgc tgttttacag cgtgggcatc ggccagatca gcagcgaggt gcccagaat    240 ctgagcgcca gcagacccca ggaccggcag tttatcctga gcagcaagaa gctgctgctg    300
agcgacagcg gcttctacct gtgtgccctg agcaccagct acgagcagta cttcggccca    360
ggcaccagac tgaccgtgac c                                             381

<210> SEQ ID NO 73
<211> LENGTH: 534
<212> TYPE: DNA
<213> ORGANISM: Artificial Sequence
<220> FEATURE:
<223> OTHER INFORMATION: Synthetic sequence 1388.3 beta chain constant
      domain (Codon-optimized NA)

<400> SEQUENCE: 73

```
gacctgaaga acgtgttccc cccagaggtg gccgtgttcg agccttctga ggccgagatc      60
agccacaccc agaaagccac cctcgtgtgt ctggccaccg cttttaccc cgaccacgtg      120 gaactgtctt ggtgggtcaa cggcaaagag gtgcactccg gcgtgtgcac cgatccccag      180
cctctgaaag aacagcccgc cctgaacgac agccggtact gcctgtccag cagactgaga      240
gtgtccgcca ccttctggca gaaccccgg aaccacttca gatgccaggt gcagttctac      300
ggcctgagcg agaacgacga gtggacccag gacagagcca gcccgtgac ccagatcgtg      360 tctgccgaag cctggggcag agccgattgc ggctttacca gcgagagcta ccagcagggc      420
gtgctgtctg ccaccatcct gtacgagatc ctgctgggaa aggccaccct gtacgccgtg      480
ctggtgtctg ccctggtgct gatggccatg gtcaagcgga aggacagcag aggc            534
```

<210> SEQ ID NO 74
<211> LENGTH: 399
<212> TYPE: DNA
<213> ORGANISM: Artificial Sequence
<220> FEATURE:
<223> OTHER INFORMATION: Synthetic sequence 1388.3 alpha chain variable
      domain (Codon-optimized NA)

<400> SEQUENCE: 74

```
atgacccggg tgtcactgct gtgggctgtg gtggtgtcca cctgtctgga aagcggcatg      60
gcccagaccg tgacacagtc ccagcctgag atgagcgtgc aggaagccga cagtgacc      120 ctgagctgca cctacgacac ctccgagaac aactactacc tgttttggta caagcagccc      180
cccagccggc agatgatcct cgtgatcaga caggaagcct ataagcagca gaacgccacc      240
gagaacagat tcagcgtgaa cttccagaag gccgccaaga gctttagcct gaagatcagc      300
gacagccagc tgggcgacac cgccatgtac ttttgcgcct ttatgaagtc ccacagcggc      360
tacatcttcg gcaccggcac acggctgaaa gtgctggct                                399
```

<210> SEQ ID NO 75
<211> LENGTH: 426
<212> TYPE: DNA
<213> ORGANISM: Artificial Sequence
<220> FEATURE:
<223> OTHER INFORMATION: Synthetic sequence 1388.3 alpha chain constant
      domain (Codon-optimized NA)

<400> SEQUENCE: 75

```
gacatccaga accccgaccc tgcagtgtac cagctgcggg acagcaagag cagcgacaag      60
agcgtgtgcc tgttcaccga cttcgacagc cagaccaacg tgtcccagag caaggacagc      120
gacgtgtaca tcaccgataa gtgcgtgctg gacatgcgga gcatggactt caagagcaac      180
agcgccgtgg cctggtccaa caagagcgac ttcgcctgcg ccaacgcctt caacaacagc      240
attatccccg aggacacatt cttcccaagc cccgagagca gctgcgacgt gaagctggtg      300
gaaaagagct cgagacaga caccaacctg aacttccaga acctcagcgt gatcggcttc      360
cggatcctgc tgctgaaggt ggccggcttc aacctgctga tgaccctgcg gctgtggtcc      420
```

```
agctga                                                          426

<210> SEQ ID NO 76
<211> LENGTH: 387
<212> TYPE: DNA
<213> ORGANISM: Artificial Sequence
<220> FEATURE:
<223> OTHER INFORMATION: Synthetic sequence 17804.1b beta chain variable
      domain (Native NA)

<400> SEQUENCE: 76
atgctctgct ctctccttgc ccttctcctg ggcactttct ttggggtcag atctcagact    60
attcatcaat ggccagcgac cctggtgcag cctgtgggca gcccgctctc tctggagtgc   120
actgtggagg gaacatcaaa ccccaaccta tactggtacc gacaggctgc aggcaggggc   180
ctccagctgc tcttctactc cgttggtatt ggccagatca gctctgaggt gcccagaat   240 ctctcagcct ccagacccca ggaccggcag ttcatcctga gttctaagaa gctccttctc   300
agtgactctg gcttctatct ctgtgcctgg agtgttgcgg tgaacactga agctttcttt   360
ggacaaggca ccagactcac agttgta                                       387

<210> SEQ ID NO 77
<211> LENGTH: 531
<212> TYPE: DNA
<213> ORGANISM: Artificial Sequence
<220> FEATURE:
<223> OTHER INFORMATION: Synthetic sequence 17804.1b beta chain constant
      domain (Native NA)

<400> SEQUENCE: 77
gaggacctga acaaagtgtt ccccccagag gtggccgtgt cgagccttc tgaggccgag     60 atcagccaca cccagaaagc caccctcgtg tgcctggcca ccggcttttt ccccgaccac   120
gtggaactgt cttggtgggt caacggcaaa gaggtgcact ccggcgtgtg caccgatccc   180
cagcctctga agaacagcc cgccctgaac gacagccgt actgcctgtc agcagactg     240 agagtgtccg ccaccttctg gcagaacccc cggaaccact tcagatgcca ggtgcagttc   300
tacggcctga gcgagaacga cgagtggacc caggacagag ccaagcccgt gacacagatc   360
gtgtctgccg aagcctgggg cagagccgat tgcggcttta cctccgtgtc ctatcagcag   420
ggcgtgctga cgccaccat cctgtacgag atcctgctgg caaggccac actgtacgcc    480 gtgctggtgt ctgccctggt gctgatggcc atggtcaagc ggaaggactt c           531

<210> SEQ ID NO 78
<211> LENGTH: 396
<212> TYPE: DNA
<213> ORGANISM: Artificial Sequence
<220> FEATURE:
<223> OTHER INFORMATION: Synthetic sequence 17804.1b alpha chain
      variable domain (Native NA)

<400> SEQUENCE: 78
atgacacgag ttagcttgct gtgggcagtc gtggtctcca cctgtcttga atccggcatg    60
gcccagacag tcactcagtc tcaaccagag atgtctgtgc aggaggcaga gactgtgacc   120
ctgagttgca catatgacac cagtgagaat aattattatt tgttctggta caagcagcct   180
cccagcaggc agatgattct cgttattcgc caagaagctt ataagcaaca gaatgcaacg   240
gagaatcgtt tctctgtgaa cttccagaaa gcagccaaat ccttcagtct caagatctca   300
gactcacagc tgggggacac tgcgatgtat ttctgcgcct cggcgagggg cgccagactc   360
```

```
atgtttggag atggaactca gctggtggtg aagccc                               396
```

<210> SEQ ID NO 79
<211> LENGTH: 426
<212> TYPE: DNA
<213> ORGANISM: Artificial Sequence
<220> FEATURE:
<223> OTHER INFORMATION: Synthetic sequence 17804.1b alpha chain
      constant domain (Native NA)

<400> SEQUENCE: 79

```
gatatccaga accctgaccc tgccgtgtac cagctgagag actctaaatc cagtgacaag    60
tctgtctgcc tattcaccga ttttgattct caaacaaatg tgtcacaaag taaggattct   120
gatgtgtata tcacagacaa atgtgtgcta gacatgaggt ctatggactt caagagcaac   180
agtgctgtgg cctggagcaa caaatctgac tttgcatgtg caaacgcctt caacaacagc   240
attattccag aagacacctt cttccccagc ccagaaagtt cctgtgatgt caagctggtc   300
gagaaaagct tgaaacaga tacgaaccta aactttcaaa acctgtcagt gattgggttc   360
cgaatcctcc tcctgaaagt ggccgggttt aatctgctca tgacgctgcg gctgtggtcc   420
agctga                                                              426
```

<210> SEQ ID NO 80
<211> LENGTH: 387
<212> TYPE: DNA
<213> ORGANISM: Artificial Sequence
<220> FEATURE:
<223> OTHER INFORMATION: Synthetic sequence 17804.1b beta chain variable
      domain (Codon-optimized NA)

<400> SEQUENCE: 80

```
atgctgtgtt ctctgctggc cctgctgctg ggcaccttct ttggagtgcg gagccagacc    60
atccaccagt ggcctgctac actggtgcag cctgtgggca gccctctgag cctggaatgt   120
accgtggaag gcaccagcaa ccccaacctg tactggtaca gacaggccgc tggcagaggc   180
ctgcagctgc tgttttacag cgtgggcatc ggccagatca gcagcgaggt gccccagaat   240
ctgagcgcca gcagacccca ggaccggcag tttatcctga gcagcaagaa gctgctgctg   300
agcgacagcg gcttctacct gtgcgcttgg agcgtggccg tgaacaccga ggcattcttt   360
ggcagggca cccggctgac cgtggtg                                        387
```

<210> SEQ ID NO 81
<211> LENGTH: 531
<212> TYPE: DNA
<213> ORGANISM: Artificial Sequence
<220> FEATURE:
<223> OTHER INFORMATION: Synthetic sequence 17804.1b beta chain constant
      domain (Codon-optimized NA)

<400> SEQUENCE: 81

```
gaagatctga caaggtgtt ccccccagag gtggccgtgt cgagccttc tgaggccgag      60
atcagccaca cccagaaagc caccctcgtg tgcctggcca ccggcttttt ccccgaccac   120
gtggaactgt cttggtgggt caacggcaaa gaggtgcact ccggcgtgtg caccgatccc   180
cagcctctga agaacagcc cgccctgaac gacagccggg actgcctgtc agcagactg    240
agagtgtccg ccaccttctg gcagaacccc cggaaccact tcagatgcca ggtgcagttc   300
tacgccctga gcgagaacga cgagtggacc caggacagag ccaagcccgt gacccagatc   360
gtgtctgccg aagcctgggg cagagccgat tgcggcttta ccagcgtgtc ctatcagcag   420
```

```
ggcgtgctgt ctgccaccat cctgtacgag atcctgctgg aaaggccac cctgtacgcc      480 gtgctggtgt ctgccctggt gctgatggcc atggtcaagc ggaaggactt c              531
```

<210> SEQ ID NO 82
<211> LENGTH: 396
<212> TYPE: DNA
<213> ORGANISM: Artificial Sequence
<220> FEATURE:
<223> OTHER INFORMATION: Synthetic sequence 17804.1b alpha chain
      variable domain (Codon-optimized NA)

<400> SEQUENCE: 82

```
atgaccagag tgtctctgct gtgggctgtg gtggtgtcca cctgtctgga aagcggcatg       60
gcccagaccg tgacacagtc ccagcctgag atgagcgtgc aggaagccga cagtgacc        120 ctgagctgca cctacgacac cagcgagaac aactactacc tgttttggta caagcagccc     180
cccagccggc agatgatcct cgtgatcaga caggaagcct ataagcagca gaacgccacc     240
gagaacagat tcagcgtgaa cttccagaag gccgccaaga gcttcagcct gaagatcagc     300
gacagccagc tgggcgacac cgccatgtac ttttgcgcct ttggcgaggg cgccagactg     360
atgtttggcg acggaaccca gctggtcgtg aagccc                              396
```

<210> SEQ ID NO 83
<211> LENGTH: 426
<212> TYPE: DNA
<213> ORGANISM: Artificial Sequence
<220> FEATURE:
<223> OTHER INFORMATION: Synthetic sequence 17804.1b alpha chain
      constant domain (Codon-optimized NA)

<400> SEQUENCE: 83

```
gacatccaga accccgaccc tgcagtgtac cagctgcggg acagcaagag cagcgacaag       60
agcgtgtgcc tgttcaccga cttcgacagc cagaccaacg tgtcccagag caaggacagc     120
gacgtgtaca tcaccgataa gtgcgtgctg gacatgcgga gcatggactt caagagcaac     180
agcgccgtgg cctggtccaa caagagcgac ttcgcctgcg ccaacgcctt caacaacagc     240
attatccccg aggacacatt cttcccaagc cccgagagca gctgcgacgt gaagctggtg     300
gaaaagagct tcgagacaga caccaacctg aacttccaga acctcagcgt gatcggcttc     360
cggatcctgc tgctgaaggt ggccggcttc aacctgctga tgaccctgcg gctgtggtcc     420
agctga                                                                426
```

<210> SEQ ID NO 84
<211> LENGTH: 387
<212> TYPE: DNA
<213> ORGANISM: Artificial Sequence
<220> FEATURE:
<223> OTHER INFORMATION: Synthetic sequence 17804.2  beta chain variable
      domain (Native NA)

<400> SEQUENCE: 84

```
atgctctgct ctctccttgc ccttctcctg ggcactttct ttggggtcag atctcagact       60
attcatcaat ggccagcgac cctggtgcag cctgtgggca gcccgctctc tctggagtgc     120
actgtggagg gaacatcaaa ccccaaccta tactggtacc gacaggctgc aggcaggggc     180
ctccagctgc tcttctactc cattggtatt gaccagatca gctctgaggt gccccagaat     240
ctctcagcct ccagacccca ggaccggcag ttcattctga gttctaagaa gctcctcctc     300
agtgactctg gcttctatct ctgtgcctgg agtgtaacca ggcacaatga gcagttcttc     360
```
gggccaggga cacggctcac cgtgcta                                        387

<210> SEQ ID NO 85
<211> LENGTH: 537
<212> TYPE: DNA
<213> ORGANISM: Artificial Sequence
<220> FEATURE:
<223> OTHER INFORMATION: Synthetic sequence 17804.2 beta chain constant
      domain (Native NA)

<400> SEQUENCE: 85
gacctgaaaa acgtgttccc acccgaggtc gctgtgtttg agccatcaga agcagagatc    60
tcccacaccc aaaaggccac actggtgtgc ctggccacag gcttctaccc cgaccacgtg   120
gagctgagct ggtgggtgaa tgggaaggag gtgcacagtg gggtctgcac agacccgcag   180
cccctcaagg agcagcccgc cctcaatgac tccagatact gcctgagcag ccgcctgagg   240
gtctcggcca ccttctggca gaaccccgc aaccacttcc gctgtcaagt ccagttctac    300
gggctctcgg agaatgacga gtggaccag gatagggcca aacctgtcac ccagatcgtc    360
agcgccgagg cctggggtag agcagactgt ggcttcacct ccgagtctta ccagcaaggg   420
gtcctgtctg ccaccatcct ctatgagatc ttgctaggga aggccacctt gtatgccgtg   480
ctggtcagtg ccctcgtgct gatggccatg gtcaagagaa aggattccag aggctag      537

<210> SEQ ID NO 86
<211> LENGTH: 405
<212> TYPE: DNA
<213> ORGANISM: Artificial Sequence
<220> FEATURE:
<223> OTHER INFORMATION: Synthetic sequence 17804.2 alpha chain variable
      domain (Native NA)

<400> SEQUENCE: 86
atgctgtgca gcctgctggc cctgctgctg ggcaccttct tcgagcccag aaccagccaa    60
gaactggagc agagtcctca gtccttgatc gtccaagagg gaagaatct caccataaac    120 tgcacgtcat caaagacgtt atatggctta tactggtata gcaaaagta tggtgaaggt    180 cttatcttct tgatgatgct acagaaaggt ggggaagaga aagtcatga aaagataact    240 gccaagttgg atgagaaaaa gcagcaaagt tccctgcata tcacagcctc ccagcccagc    300
catgcaggca tctacctctg tggagcagcc cctacatact cgaattatgg aggaagccaa    360
ggaaatctca tctttggaaa aggcactaaa ctctctgtta aacca                    405

<210> SEQ ID NO 87
<211> LENGTH: 426
<212> TYPE: DNA
<213> ORGANISM: Artificial Sequence
<220> FEATURE:
<223> OTHER INFORMATION: Synthetic sequence 17804.2 alpha chain constant
      domain (Native NA)

<400> SEQUENCE: 87
gatatccaga accctgaccc tgccgtgtac cagctgagag actctaaatc cagtgacaag    60
tctgtctgcc tattcaccga ttttgattct caaacaaatg tgtcacaaag taaggattct   120
gatgtgtata tcagacaa atgtgtgcta gacatgaggt ctatggactt caagagcaac    180
agtgctgtgg cctggagcaa caaatctgac tttgcatgtg caaacgcctt caacaacagc   240
attattccag aagacacctt cttccccagc ccagaaagtt cctgtgatgt caagctggtc   300
gagaaaagct ttgaaacaga tacgaaccta actttcaaa acctgtcagt gattgggttc   360
cgaatcctcc tcctgaaagt ggccgggttt aatctgctca tgacgctgcg gctgtggtcc    420
agctga                                                               426

<210> SEQ ID NO 88
<211> LENGTH: 387
<212> TYPE: DNA
<213> ORGANISM: Artificial Sequence
<220> FEATURE:
<223> OTHER INFORMATION: Synthetic sequence 17804.2 beta chain variable
      domain(Codon-optimized NA)

<400> SEQUENCE: 88
atgctgtgtt ctctgctggc tctgctgctg ggcaccttct ttggagtgcg gagccagacc     60
atccaccagt ggcctgctac actggtgcag cctgtgggca gccctctgag cctggaatgt    120
accgtggaag gcaccagcaa ccccaacctg tactggtaca acaggccgc tggcagaggc    180 ctgcagctgc tgttttacag catcggcatc gaccagatca gcagcgaggt gccccagaac    240
ctgagcgcca gcagacccca ggaccggcag tttatcctga gcagcaagaa gctgctgctg    300
agcgacagcg gcttctacct gtgcgcttgg agcgtgaccc ggcacaacga gcagttcttt    360
ggccctggca cccggctgac cgtgctg                                         387

<210> SEQ ID NO 89
<211> LENGTH: 534
<212> TYPE: DNA
<213> ORGANISM: Artificial Sequence
<220> FEATURE:
<223> OTHER INFORMATION: Synthetic sequence 17804.2 beta chain constant
      domain (Codon-optimized NA)

<400> SEQUENCE: 89
gacctgaaga acgtgttccc cccagaggtg gccgtgttcg agccttctga ggccgagatc     60
agccacaccc agaaagccac cctcgtgtgt ctggccaccg cttttaccc cgaccacgtg    120 gaactgtctt ggtgggtcaa cggcaaagag gtgcactccg gcgtgtgcac cgatccccag    180
cctctgaaag aacagcccgc cctgaacgac agccggtact gcctgtccag cagactgaga    240
gtgtccgcca ccttctggca gaaccccggg aaccacttca gatgccaggt gcagttctac    300
ggcctgagcg agaacgacga gtggacccag gacagagcca gcccgtgac ccagatcgtg    360 tctgccgaag cctggggcag agccgattgc ggctttacca gcgagagcta ccagcagggc    420
gtgctgtctg ccaccatcct gtacgagatc ctgctgggaa aggccaccct gtacgccgtg    480
ctggtgtctg ccctggtgct gatggccatg gtcaagcgga aggacagcag aggc          534

<210> SEQ ID NO 90
<211> LENGTH: 405
<212> TYPE: DNA
<213> ORGANISM: Artificial Sequence
<220> FEATURE:
<223> OTHER INFORMATION: Synthetic sequence 17804.2 alpha chain variable
      domain (Codon-optimized NA)

<400> SEQUENCE: 90
atgctgtgca gcctgctggc cctgctgctg ggaacatttt tcgagccccg gaccagccag     60
gaactggaac agagcccaca gagcctgatc gtgcaggaag caagaacct gaccatcaac    120 tgcaccagct ccaagacact gtacggcctg tattggtata gcagaagta cggcgagggc    180 ctgatcttcc tgatgatgct gcagaagggc ggcgaggaaa gagccacga gaagatcacc    240 gccaagctgg acgagaagaa gcagcagtcc agcctgcaca tcaccgcctc ccagccttct    300

```
cacgccggca tctatctgtg tggcgccgct cccacctaca gcaactatgg cggcagccag    360
ggcaatctga tcttcggcaa gggcaccaag ctgagcgtga agccc                    405
```

<210> SEQ ID NO 91
<211> LENGTH: 426
<212> TYPE: DNA
<213> ORGANISM: Artificial Sequence
<220> FEATURE:
<223> OTHER INFORMATION: Synthetic sequence 17804.2 alpha chain constant
      domain (Codon-optimized NA)

<400> SEQUENCE: 91

```
gacatccaga accccgaccc tgcagtgtac cagctgcggg acagcaagag cagcgacaag     60
agcgtgtgcc tgttcaccga cttcgacagc cagaccaacg tgtcccagag caaggacagc    120
gacgtgtaca tcaccgataa gtgcgtgctg gacatgcgga gcatggactt caagagcaac    180
agcgccgtgg cctggtccaa caagagcgac ttcgcctgcg ccaacgcctt caacaacagc    240
attatccccg aggacacatt cttcccaagc cccgagagca gctgcgacgt gaagctggtg    300
gaaaagagct cgagacagag accaacctg aacttccaga acctcagcgt gatcggcttc    360
cggatcctgc tgctgaaggt ggccggcttc aacctgctga tgaccctgcg gctgtggtcc    420
agctga                                                              426
```

<210> SEQ ID NO 92
<211> LENGTH: 15
<212> TYPE: DNA
<213> ORGANISM: Artificial Sequence
<220> FEATURE:
<223> OTHER INFORMATION: Synthetic sequence 1388.1 beta chain CDR1
      domain (Codon-optimized NA)

<400> SEQUENCE: 92

```
atggaccacg agaat                                                     15
```

<210> SEQ ID NO 93
<211> LENGTH: 18
<212> TYPE: DNA
<213> ORGANISM: Artificial Sequence
<220> FEATURE:
<223> OTHER INFORMATION: Synthetic sequence 1388.1 beta chain CDR2
      domain (Codon-optimized NA)

<400> SEQUENCE: 93

```
agctacgacg tgaagatg                                                  18
```

<210> SEQ ID NO 94
<211> LENGTH: 45
<212> TYPE: DNA
<213> ORGANISM: Artificial Sequence
<220> FEATURE:
<223> OTHER INFORMATION: Synthetic sequence 1388.1 beta chain CDR3
      domain (Codon-optimized NA)

<400> SEQUENCE: 94

```
tgcgcctcca acaaccggga cagctacaac agcccctgc acttc                     45
```

<210> SEQ ID NO 95
<211> LENGTH: 18
<212> TYPE: DNA
<213> ORGANISM: Artificial Sequence
<220> FEATURE:
<223> OTHER INFORMATION: Synthetic sequence 1388.1 alpha chain CDR1
      domain (Codon-optimized NA)

```
<400> SEQUENCE: 95
tacagcggca gccccgag                                                      18

<210> SEQ ID NO 96
<211> LENGTH: 12
<212> TYPE: DNA
<213> ORGANISM: Artificial Sequence
<220> FEATURE:
<223> OTHER INFORMATION: Synthetic sequence 1388.1 alpha chain CDR2
      domain (Codon-optimized NA)

<400> SEQUENCE: 96
cacatcagca ga                                                            12

<210> SEQ ID NO 97
<211> LENGTH: 39
<212> TYPE: DNA
<213> ORGANISM: Artificial Sequence
<220> FEATURE:
<223> OTHER INFORMATION: Synthetic sequence 1388.1 alpha chain CDR3
      domain (Codon-optimized NA)

<400> SEQUENCE: 97
tgcgccctga gatccggcgg ctaccagaaa gtgacattt                               39

<210> SEQ ID NO 98
<211> LENGTH: 15
<212> TYPE: DNA
<213> ORGANISM: Artificial Sequence
<220> FEATURE:
<223> OTHER INFORMATION: Synthetic sequence 1388.2b beta chain CDR1
      domain (Codon-optimized NA)

<400> SEQUENCE: 98
agcggcgacc tgagc                                                         15

<210> SEQ ID NO 99
<211> LENGTH: 18
<212> TYPE: DNA
<213> ORGANISM: Artificial Sequence
<220> FEATURE:
<223> OTHER INFORMATION: synthetic sequence 1388.2b  beta chain CDR2
      domain (Codon-optimized NA)

<400> SEQUENCE: 99
tactacaacg gcgaggaa                                                      18

<210> SEQ ID NO 100
<211> LENGTH: 18
<212> TYPE: DNA
<213> ORGANISM: Artificial Sequence
<220> FEATURE:
<223> OTHER INFORMATION: Synthetic sequence 1388.2b  beta chain CDR3
      domain (Codon-optimized NA)

<400> SEQUENCE: 100
tactacaacg gcgaggaa                                                      18

<210> SEQ ID NO 101
<211> LENGTH: 18
<212> TYPE: DNA
<213> ORGANISM: Artificial Sequence
<220> FEATURE:
<223> OTHER INFORMATION: Synthetic sequence 1388.2b  alpha chain CDR1
      domain (Codon-optimized NA)

<400> SEQUENCE: 101
```

```
gacagcagca gcacctac                                                 18
```

<210> SEQ ID NO 102
<211> LENGTH: 21
<212> TYPE: DNA
<213> ORGANISM: Artificial Sequence
<220> FEATURE:
<223> OTHER INFORMATION: Synthetic sequence 1388.2b  alpha chain CDR2
      domain (Codon-optimized NA)

<400> SEQUENCE: 102

```
atcttcagca acatggacat g                                             21
```

<210> SEQ ID NO 103
<211> LENGTH: 33
<212> TYPE: DNA
<213> ORGANISM: Artificial Sequence
<220> FEATURE:
<223> OTHER INFORMATION: Synthetic sequence 1388.2b  alpha chain CDR3
      domain (Codon-optimized NA)

<400> SEQUENCE: 103

```
tgcgccgaga gcatcgacgc ccggctgatg ttt                                33
```

<210> SEQ ID NO 104
<211> LENGTH: 18
<212> TYPE: DNA
<213> ORGANISM: Artificial Sequence
<220> FEATURE:
<223> OTHER INFORMATION: Synthetic sequence 1388.3 beta chain CDR1
      domain (Codon-optimized NA)

<400> SEQUENCE: 104

```
ggcaccagca accccaac                                                 18
```

<210> SEQ ID NO 105
<211> LENGTH: 15
<212> TYPE: DNA
<213> ORGANISM: Artificial Sequence
<220> FEATURE:
<223> OTHER INFORMATION: Synthetic sequence 1388.3 beta chain CDR2
      domain (Codon-optimized NA)

<400> SEQUENCE: 105

```
agcgtgggca tcggc                                                    15
```

<210> SEQ ID NO 106
<211> LENGTH: 33
<212> TYPE: DNA
<213> ORGANISM: Artificial Sequence
<220> FEATURE:
<223> OTHER INFORMATION: Synthetic sequence 1388.3  beta chain CDR3
      domain (Codon-optimized NA)

<400> SEQUENCE: 106

```
tgtgccctga gcaccagcta cgagcagtac ttc                                33
```

<210> SEQ ID NO 107
<211> LENGTH: 21
<212> TYPE: DNA
<213> ORGANISM: Artificial Sequence
<220> FEATURE:
<223> OTHER INFORMATION: Synthetic sequence 1388.3  alpha chain CDR1
      domain (Codon-optimized NA)

<400> SEQUENCE: 107
acctccgaga acaactacta c                                         21

<210> SEQ ID NO 108
<211> LENGTH: 24
<212> TYPE: DNA
<213> ORGANISM: Artificial Sequence
<220> FEATURE:
<223> OTHER INFORMATION: Synthetic sequence 1388.3  alpha chain CDR2
      domain (Codon-optimized NA)

<400> SEQUENCE: 108
caggaagcct ataagcagca gaac                                      24

<210> SEQ ID NO 109
<211> LENGTH: 39
<212> TYPE: DNA
<213> ORGANISM: Artificial Sequence
<220> FEATURE:
<223> OTHER INFORMATION: Synthetic sequence 1388.3 alpha chain CDR3
      domain (Codon-optimized NA)

<400> SEQUENCE: 109 tgcgcctttta tgaagtccca cagcggctac atcttcggc                     39

<210> SEQ ID NO 110
<211> LENGTH: 18
<212> TYPE: DNA
<213> ORGANISM: Artificial Sequence
<220> FEATURE:
<223> OTHER INFORMATION: Synthetic sequence 17084.1b beta chain CDR1
      domain (Codon-optimized NA)

<400> SEQUENCE: 110
ggcaccagca accccaac                                             18

<210> SEQ ID NO 111
<211> LENGTH: 15
<212> TYPE: DNA
<213> ORGANISM: Artificial Sequence
<220> FEATURE:
<223> OTHER INFORMATION: Synthetic sequence 17084.1b beta chain CDR2
      domain (Codon-optimized NA)

<400> SEQUENCE: 111
agcgtgggca tcggc                                                15

<210> SEQ ID NO 112
<211> LENGTH: 39
<212> TYPE: DNA
<213> ORGANISM: Artificial Sequence
<220> FEATURE:
<223> OTHER INFORMATION: Synthetic sequence 17084.1b beta chain CDR3
      domain (Codon-optimized NA)

<400> SEQUENCE: 112
tgcgcttgga gcgtggccgt gaacaccgag gcattcttt                      39

<210> SEQ ID NO 113
<211> LENGTH: 21
<212> TYPE: DNA
<213> ORGANISM: Artificial Sequence
<220> FEATURE:
<223> OTHER INFORMATION: Synthetic sequence 17084.1b alpha chain CDR1
      domain (Codon-optimized NA)

<400> SEQUENCE: 113
accagcgaga acaactacta c                                         21

<210> SEQ ID NO 114
<211> LENGTH: 24
<212> TYPE: DNA
<213> ORGANISM: Artificial Sequence
<220> FEATURE:
<223> OTHER INFORMATION: Synthetic sequence 17084.1b alpha chain CDR2
      domain (Codon-optimized NA)

<400> SEQUENCE: 114
caggaagcct ataagcagca gaac                                              24

<210> SEQ ID NO 115
<211> LENGTH: 33
<212> TYPE: DNA
<213> ORGANISM: Artificial Sequence
<220> FEATURE:
<223> OTHER INFORMATION: Synthetic sequence 17084.1b alpha chain CDR3
      domain (Codon-optimized NA)

<400> SEQUENCE: 115
tgcgcctttg gcgagggcgc cagactgatg ttt                                    33

<210> SEQ ID NO 116
<211> LENGTH: 18
<212> TYPE: DNA
<213> ORGANISM: Artificial Sequence
<220> FEATURE:
<223> OTHER INFORMATION: Synthetic sequence 17084.2 beta chain CDR1
      domain (Codon-optimized NA)

<400> SEQUENCE: 116
ggcaccagca accccaac                                                     18

<210> SEQ ID NO 117
<211> LENGTH: 15
<212> TYPE: DNA
<213> ORGANISM: Artificial Sequence
<220> FEATURE:
<223> OTHER INFORMATION: Synthetic sequence 17084.2 beta chain CDR2
      domain (Codon-optimized NA)

<400> SEQUENCE: 117
agcatcggca tcgac                                                        15

<210> SEQ ID NO 118
<211> LENGTH: 39
<212> TYPE: DNA
<213> ORGANISM: Artificial Sequence
<220> FEATURE:
<223> OTHER INFORMATION: Synthetic sequence 17084.2  beta chain CDR3
      domain (Codon-optimized NA)

<400> SEQUENCE: 118
tgcgcttgga gcgtgacccg gcacaacgag cagttcttt                              39

<210> SEQ ID NO 119
<211> LENGTH: 15
<212> TYPE: DNA
<213> ORGANISM: Artificial Sequence
<220> FEATURE:
<223> OTHER INFORMATION: Synthetic sequence 17084.2  alpha chain CDR1
      domain (Codon-optimized NA)

<400> SEQUENCE: 119
aagacactgt acggc                                                        15

<210> SEQ ID NO 120
<211> LENGTH: 21
<212> TYPE: DNA
<213> ORGANISM: Artificial Sequence
<220> FEATURE:
<223> OTHER INFORMATION: Synthetic sequence 17084.2 alpha chain CDR2 domain (Codon-optimized NA)

<400> SEQUENCE: 120
ctgcagaagg gcggcgagga a                                              21

<210> SEQ ID NO 121
<211> LENGTH: 57
<212> TYPE: DNA
<213> ORGANISM: Artificial Sequence
<220> FEATURE:
<223> OTHER INFORMATION: Synthetic sequence 17084.2 alpha chain CDR3 domain (Codon-optimized NA)

<400> SEQUENCE: 121
tgtggcgccg ctcccaccta cagcaactat ggcggcagcc agggcaatct gatcttc       57

<210> SEQ ID NO 122
<211> LENGTH: 309
<212> TYPE: PRT
<213> ORGANISM: Artificial Sequence
<220> FEATURE:
<223> OTHER INFORMATION: Synthetic sequence Human MAGE-A1 (amino acid)

<400> SEQUENCE: 122

Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
    130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr

```
                225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
                260                 265                 270

Glu Thr Ser Tyr Val Lys Val Leu Glu Tyr Val Ile Lys Val Ser Ala
                275                 280                 285

Arg Val Arg Phe Phe Phe Pro Ser Leu Arg Glu Ala Ala Leu Arg Glu
                290                 295                 300

Glu Glu Glu Gly Val
305

<210> SEQ ID NO 123
<211> LENGTH: 9
<212> TYPE: PRT
<213> ORGANISM: Artificial Sequence
<220> FEATURE:
<223> OTHER INFORMATION: Synthetic sequence Human MAGE-A1 278-286

<400> SEQUENCE: 123

Lys Val Leu Glu Tyr Val Ile Lys Val
1               5

<210> SEQ ID NO 124
<211> LENGTH: 22
<212> TYPE: PRT
<213> ORGANISM: Artificial Sequence
<220> FEATURE:
<223> OTHER INFORMATION: Synthetic sequence Porcine teschovirus-1 2A
      (P2A) peptide

<400> SEQUENCE: 124

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 125
<211> LENGTH: 25
<212> TYPE: PRT
<213> ORGANISM: Artificial Sequence
<220> FEATURE:
<223> OTHER INFORMATION: Synthetic sequence Foot-and-Mouth disease virus
      2A (F2A) peptide

<400> SEQUENCE: 125

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 126
<211> LENGTH: 20
<212> TYPE: PRT
<213> ORGANISM: Artificial Sequence
<220> FEATURE:
<223> OTHER INFORMATION: Synthetic sequence Equine rhinitis A virus
      (ERAV) 2A (E2A) peptide

<400> SEQUENCE: 126

Gln Cys Thr Asn Tyr Ala Leu Leu Lys Leu Ala Gly Asp Val Glu Ser
1               5                   10                  15

Asn Pro Gly Pro
```

```
                     20

<210> SEQ ID NO 127
<211> LENGTH: 24
<212> TYPE: PRT
<213> ORGANISM: Artificial Sequence
<220> FEATURE:
<223> OTHER INFORMATION: Synthetic sequence Thoseaasigna virus 2A (T2A)
      peptide

<400> SEQUENCE: 127

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 128
<211> LENGTH: 66
<212> TYPE: DNA
<213> ORGANISM: Artificial Sequence
<220> FEATURE:
<223> OTHER INFORMATION: Synthetic sequence Porcine teschovirus-1 2A
      (P2A) peptide  (NA)

<400> SEQUENCE: 128
ggaagcggag ctactaactt cagcctgctg aagcaggctg agacgtgga ggagaaccct    60 ggacct                                                              66

<210> SEQ ID NO 129
<211> LENGTH: 66
<212> TYPE: DNA
<213> ORGANISM: Artificial Sequence
<220> FEATURE:
<223> OTHER INFORMATION: Synthetic sequence Porcine teschovirus-1 2A
      (P2A) peptide  (CO-NA)

<400> SEQUENCE: 129
ggttccggag ccacgaactt ctctctgtta aagcaagcag gagacgtgga agaaaacccc    60
ggtccc                                                               66

<210> SEQ ID NO 130
<211> LENGTH: 75
<212> TYPE: DNA
<213> ORGANISM: Artificial Sequence
<220> FEATURE:
<223> OTHER INFORMATION: Synthetic sequence Foot-and-Mouth disease virus
      2A (F2A) peptide (NA)

<400> SEQUENCE: 130
ggaagcggag tgaaacagac tttgaatttt gaccttctca agttggcggg agacgtggag    60
tccaaccctg gacct                                                     75

<210> SEQ ID NO 131
<211> LENGTH: 69
<212> TYPE: DNA
<213> ORGANISM: Artificial Sequence
<220> FEATURE:
<223> OTHER INFORMATION: Synthetic sequence Equine rhinitis A virus
      (ERAV) 2A (E2A) peptide (NA)

<400> SEQUENCE: 131
ggaagcggac agtgtactaa ttatgctctc ttgaaattgg ctggagatgt tgagagcaac    60
cctggacct                                                            69
```

```
<210> SEQ ID NO 132
<211> LENGTH: 63
<212> TYPE: DNA
<213> ORGANISM: Artificial Sequence
<220> FEATURE:
<223> OTHER INFORMATION: Synthetic sequence Thoseaasigna virus 2A (T2A)
      peptide (NA)

<400> SEQUENCE: 132
ggaagcggag agggcagagg aagtctgcta acatgcggtg acgtcgagga gaatcctgga      60
cct                                                                   63

<210> SEQ ID NO 133
<211> LENGTH: 15
<212> TYPE: PRT
<213> ORGANISM: Artificial Sequence
<220> FEATURE:
<223> OTHER INFORMATION: Synthetic sequence Glycine-serine linker

<400> SEQUENCE: 133

Gly Gly Gly Gly Ser Gly Gly Gly Gly Ser Gly Gly Gly Gly Ser
1               5                   10                  15

<210> SEQ ID NO 134
<211> LENGTH: 18
<212> TYPE: PRT
<213> ORGANISM: Artificial Sequence
<220> FEATURE:
<223> OTHER INFORMATION: Synthetic sequence Glycine-serine linker

<400> SEQUENCE: 134

Gly Ser Thr Ser Gly Gly Gly Ser Gly Gly Gly Ser Gly Gly Gly Gly
1               5                   10                  15

Ser Ser

<210> SEQ ID NO 135
<211> LENGTH: 25
<212> TYPE: DNA
<213> ORGANISM: Artificial Sequence
<220> FEATURE:
<223> OTHER INFORMATION: Synthetic sequence sgRNA Forward Oligo:
      TRAC_sgRNA_pLenti_F1

<400> SEQUENCE: 135
caccggagaa tcaaaatcgg tgaat                                           25

<210> SEQ ID NO 136
<211> LENGTH: 25
<212> TYPE: DNA
<213> ORGANISM: Artificial Sequence
<220> FEATURE:
<223> OTHER INFORMATION: Synthetic sequence sgRNA Reverse Oligo:
      TRAC_sgRNA_pLenti_R1

<400> SEQUENCE: 136
aaacattcac cgattttgat tctcc                                           25

<210> SEQ ID NO 137
<211> LENGTH: 24
<212> TYPE: DNA
<213> ORGANISM: Artificial Sequence
<220> FEATURE:
<223> OTHER INFORMATION: Synthetic sequence sgRNA Forward Oligo:
      PD1_sgRNA_F1

<400> SEQUENCE: 137
```
caccgcagtt gtgtgacacg gaag                                         24

<210> SEQ ID NO 138
<211> LENGTH: 24
<212> TYPE: DNA
<213> ORGANISM: Artificial Sequence
<220> FEATURE:
<223> OTHER INFORMATION: Synthetic sequence sgRNA Reverse Oligo:
      PD1_sgRNA_R1

<400> SEQUENCE: 138
aaaccttccg tgtcacacaa ctgc                                         24

<210> SEQ ID NO 139
<211> LENGTH: 25
<212> TYPE: DNA
<213> ORGANISM: Artificial Sequence
<220> FEATURE:
<223> OTHER INFORMATION: Synthetic sequence sgRNA Forward Oligo:
      CTLA4_sgRNA_F1

<400> SEQUENCE: 139
caccggcaaa ggtgagtgag acttt                                        25

<210> SEQ ID NO 140
<211> LENGTH: 25
<212> TYPE: DNA
<213> ORGANISM: Artificial Sequence
<220> FEATURE:
<223> OTHER INFORMATION: Synthetic sequence sgRNA Reverse Oligo:
      CTLA4_sgRNA_R1

<400> SEQUENCE: 140
aaacaaagtc tcactcacct ttgcc                                        25

<210> SEQ ID NO 141
<211> LENGTH: 25
<212> TYPE: DNA
<213> ORGANISM: Artificial Sequence
<220> FEATURE:
<223> OTHER INFORMATION: Synthetic sequence sgRNA Forward Oligo:
      LAG3_sgRNA_F1

<400> SEQUENCE: 141
caccggtttc tgcagccgct ttggg                                        25

<210> SEQ ID NO 142
<211> LENGTH: 25
<212> TYPE: DNA
<213> ORGANISM: Artificial Sequence
<220> FEATURE:
<223> OTHER INFORMATION: Synthetic sequence sgRNA Reverse Oligo:
      LAG3_sgRNA_R2

<400> SEQUENCE: 142 aaacccaaa gcggctgcag aaacc                                         25

<210> SEQ ID NO 143
<211> LENGTH: 214
<212> TYPE: PRT
<213> ORGANISM: Artificial Sequence
<220> FEATURE:
<223> OTHER INFORMATION: Synthetic sequence CD8 co-receptor alpha chain

<400> SEQUENCE: 143

Ser Gln Phe Arg Val Ser Pro Leu Asp Arg Thr Trp Asn Leu Gly Glu

```
  1               5                   10                  15
Thr Val Glu Leu Lys Cys Gln Val Leu Leu Ser Asn Pro Thr Ser Gly
                20                  25                  30

Cys Ser Trp Leu Phe Gln Pro Arg Gly Ala Ala Ala Ser Pro Thr Phe
                35                  40                  45

Leu Leu Tyr Leu Ser Gln Asn Lys Pro Lys Ala Ala Glu Gly Leu Asp
                50                  55                  60

Thr Gln Arg Phe Ser Gly Lys Arg Leu Gly Asp Thr Phe Val Leu Thr
 65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
               100                 105                 110

Pro Ala Lys Pro Thr Thr Thr Pro Ala Pro Arg Pro Pro Thr Pro Ala
               115                 120                 125

Pro Thr Ile Ala Ser Gln Pro Leu Ser Leu Arg Pro Glu Ala Cys Arg
               130                 135                 140

Pro Ala Ala Gly Gly Ala Val His Thr Arg Gly Leu Asp Phe Ala Cys
145                 150                 155                 160

Asp Ile Tyr Ile Trp Ala Pro Leu Ala Gly Thr Cys Gly Val Leu Leu
                165                 170                 175

Leu Ser Leu Val Ile Thr Leu Tyr Cys Asn His Arg Asn Arg Arg
                180                 185                 190

Val Cys Lys Cys Pro Arg Pro Val Val Lys Ser Gly Asp Lys Pro Ser
                195                 200                 205

Leu Ser Ala Arg Tyr Val
                210

<210> SEQ ID NO 144
<211> LENGTH: 189
<212> TYPE: PRT
<213> ORGANISM: Artificial Sequence
<220> FEATURE:
<223> OTHER INFORMATION: Synthetic sequence "CD8 co-receptor beta chain
      isoform 1

<400> SEQUENCE: 144

Leu Gln Gln Thr Pro Ala Tyr Ile Lys Val Gln Thr Asn Lys Met Val
 1               5                  10                  15

Met Leu Ser Cys Glu Ala Lys Ile Ser Leu Ser Asn Met Arg Ile Tyr
                20                  25                  30

Trp Leu Arg Gln Arg Gln Ala Pro Ser Ser Asp Ser His His Glu Phe
                35                  40                  45

Leu Ala Leu Trp Asp Ser Ala Lys Gly Thr Ile His Gly Glu Glu Val
                50                  55                  60

Glu Gln Glu Lys Ile Ala Val Phe Arg Asp Ala Ser Arg Phe Ile Leu
 65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
               100                 105                 110

Val Val Asp Phe Leu Pro Thr Thr Ala Gln Pro Thr Lys Lys Ser Thr
               115                 120                 125

Leu Lys Lys Arg Val Cys Arg Leu Pro Arg Pro Glu Thr Gln Lys Gly
               130                 135                 140
```

```
Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Phe Tyr Lys
            180                 185
```

<210> SEQ ID NO 145
<211> LENGTH: 200
<212> TYPE: PRT
<213> ORGANISM: Artificial Sequence
<220> FEATURE:
<223> OTHER INFORMATION: Synthetic sequence CD8 co-receptor beta chain isoform 2

<400> SEQUENCE: 145

```
Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Leu Arg Leu His Pro Leu
            180                 185                 190

Glu Lys Cys Ser Arg Met Asp Tyr
            195                 200
```

<210> SEQ ID NO 146
<211> LENGTH: 225
<212> TYPE: PRT
<213> ORGANISM: Artificial Sequence
<220> FEATURE:
<223> OTHER INFORMATION: Synthetic sequence CD8 co-receptor beta chain isoform 3

<400> SEQUENCE: 146

```
Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45
```

```
Leu Ala Leu Trp Asp Ser Ala Lys Gly Thr Ile His Gly Glu Val
 50                  55                  60

Glu Gln Glu Lys Ile Ala Val Phe Arg Asp Ala Ser Arg Phe Ile Leu
 65                  70                  75                  80

Asn Leu Thr Ser Val Lys Pro Glu Asp Ser Gly Ile Tyr Phe Cys Met
                     85                  90                  95

Ile Val Gly Ser Pro Glu Leu Thr Phe Gly Lys Gly Thr Gln Leu Ser
                100                 105                 110

Val Val Asp Phe Leu Pro Thr Thr Ala Gln Pro Thr Lys Lys Ser Thr
                115                 120                 125

Leu Lys Lys Arg Val Cys Arg Leu Pro Arg Pro Glu Thr Gln Lys Gly
130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Lys Phe Asn Ile Val Cys
                180                 185                 190

Leu Lys Ile Ser Gly Phe Thr Thr Cys Cys Cys Phe Gln Ile Leu Gln
                195                 200                 205

Ile Ser Arg Glu Tyr Gly Phe Gly Val Leu Leu Gln Lys Asp Ile Gly
                210                 215                 220

Gln
225

<210> SEQ ID NO 147
<211> LENGTH: 225
<212> TYPE: PRT
<213> ORGANISM: Artificial Sequence
<220> FEATURE:
<223> OTHER INFORMATION: Synthetic sequence CD8 co-receptor beta chain
      isoform 4

<400> SEQUENCE: 147

Leu Gln Gln Thr Pro Ala Tyr Ile Lys Val Gln Thr Asn Lys Met Val
 1                   5                  10                  15

Met Leu Ser Cys Glu Ala Lys Ile Ser Leu Ser Asn Met Arg Ile Tyr
                 20                  25                  30

Trp Leu Arg Gln Arg Gln Ala Pro Ser Ser Asp Ser His His Glu Phe
             35                  40                  45

Leu Ala Leu Trp Asp Ser Ala Lys Gly Thr Ile His Gly Glu Val
 50                  55                  60

Glu Gln Glu Lys Ile Ala Val Phe Arg Asp Ala Ser Arg Phe Ile Leu
 65                  70                  75                  80

Asn Leu Thr Ser Val Lys Pro Glu Asp Ser Gly Ile Tyr Phe Cys Met
                     85                  90                  95

Ile Val Gly Ser Pro Glu Leu Thr Phe Gly Lys Gly Thr Gln Leu Ser
                100                 105                 110

Val Val Asp Phe Leu Pro Thr Thr Ala Gln Pro Thr Lys Lys Ser Thr
                115                 120                 125

Leu Lys Lys Arg Val Cys Arg Leu Pro Arg Pro Glu Thr Gln Lys Gly
130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175
```

```
Arg Arg Ala Arg Leu Arg Phe Met Lys Gln Lys Phe Asn Ile Val Cys
            180                 185                 190

Leu Lys Ile Ser Gly Phe Thr Thr Cys Cys Cys Phe Gln Ile Leu Gln
            195                 200                 205

Ile Ser Arg Glu Tyr Gly Phe Gly Val Leu Leu Gln Lys Asp Ile Gly
            210                 215                 220

Gln
225

<210> SEQ ID NO 148
<211> LENGTH: 222
<212> TYPE: PRT
<213> ORGANISM: Artificial Sequence
<220> FEATURE:
<223> OTHER INFORMATION: Synthetic sequence CD8 co-receptor beta chain
      isoform 5

<400> SEQUENCE: 148

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
            35                  40                  45

Leu Ala Leu Trp Asp Ser Ala Lys Gly Thr Ile His Gly Glu Glu Val
        50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
            115                 120                 125

Leu Lys Lys Arg Val Cys Arg Leu Pro Arg Pro Glu Thr Gln Lys Gly
130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Pro Gln Gly Glu Gly Ile
            180                 185                 190

Ser Gly Thr Phe Val Pro Gln Cys Leu His Gly Tyr Tyr Ser Asn Thr
            195                 200                 205

Thr Thr Ser Gln Lys Leu Leu Asn Pro Trp Ile Leu Lys Thr
210                 215                 220
```